United States Patent
Erickson et al.

(10) Patent No.: US 7,037,916 B2
(45) Date of Patent: May 2, 2006

(54) PYRIMIDINE DERIVATIVES AS IL-8 RECEPTOR ANTAGONISTS

(75) Inventors: Shawn David Erickson, Leonia, NJ (US); John J. Baldwin, Gwynedd Valley, PA (US); Roland Ellwood Dolle, III, King of Prussia, PA (US); James Inglese, Lansdale, PA (US); Michael H. J. Ohlmeyer, Plainsboro, NJ (US); Koc-Kan Ho, Monmouth Junction, NJ (US); Adolph C Bohnstedt, Burlington, NJ (US); Steven G. Kultgen, Dayton, NJ (US); Paolo Giovanni Martino Conti, Heesch (NL); Dirk Leysen, Lommel (BE); Jaap van der Louw, Oss (NL)

(73) Assignee: Pharmacopeia Drug Discovery, Inc., Princeton, NJ (US)

( * ) Notice: Subject to any disclaimer, the term of this patent is extended or adjusted under 35 U.S.C. 154(b) by 326 days.

(21) Appl. No.: 10/340,398

(22) Filed: Jan. 10, 2003

(65) Prior Publication Data

US 2004/0087601 A1    May 6, 2004

Related U.S. Application Data

(63) Continuation-in-part of application No. 10/167,232, filed on Jun. 11, 2002, now abandoned, which is a continuation of application No. 09/616,496, filed on Jul. 14, 2000, now abandoned.

(60) Provisional application No. 60/144,160, filed on Jul. 15, 1999.

(51) Int. Cl.
*A61K 31/52* (2006.01)
*C07D 413/00* (2006.01)
*C07D 239/02* (2006.01)
*C70D 473/00* (2006.01)

(52) U.S. Cl. ............... 514/262; 514/266; 514/269; 514/235.8; 544/320; 544/319; 544/270; 544/122; 544/123; 544/114; 544/115

(58) Field of Classification Search .......... 514/262, 514/235.8, 269, 266; 544/320, 319, 122, 544/123, 114, 115, 270

See application file for complete search history.

(56) References Cited

U.S. PATENT DOCUMENTS 5,780,483 A * 7/1998 Widdowson et al. ....... 514/311
5,972,946 A   10/1999 Murata et al.
6,458,798 B1  10/2002 Fujita et al.

2002/0065270 A1  5/2002  Moriarty et al. ............ 514/218
2003/0097004 A1  5/2003  Taveras et al. ............. 548/152
2003/0139435 A1  7/2003  Ahmed et al. .............. 514/275

FOREIGN PATENT DOCUMENTS

| EP | 0257850 | 3/1988 |
| EP | 0 640 599 A1 | 5/1995 |
| GB | 2139623 | 11/1984 |
| JP | 4-1192 | 1/1992 |
| JP | 10 130150 | 5/1998 |
| WO | WO 97/25324 | 7/1997 |

(Continued)

OTHER PUBLICATIONS

Corona et al. "Synthesis and in vitro study of platelet antiaggregant activity . . ." Eur.J. Med. Chem. 26, 729-733 (1991).

(Continued)

*Primary Examiner*—James O. Wilson
*Assistant Examiner*—Ganapathy Krishnan
(74) *Attorney, Agent, or Firm*—Heslin Rothenberg Farley & Mesiti, P.C.; Philip E. Hansen

(57) ABSTRACT

Compounds containing the pyrimidine nucleus and their use to treat diseases and conditions related to inappropriate Interleukin-8 receptor activity are disclosed. The compounds are of the formula I

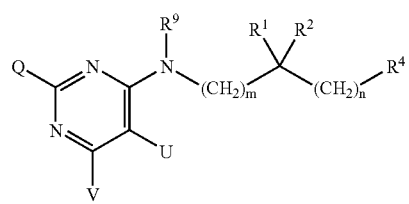

In these compounds, Q is preferably unsubstituted and substituted heterocyclyl; U is usually hydrogen or fluorine; and V is preferably hydrogen, halogen, alkyl, —O—alkyl or —S-alkyl. A representative example is:

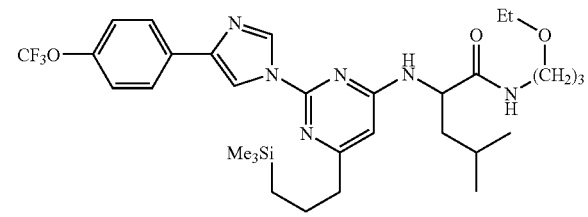

33 Claims, No Drawings

FOREIGN PATENT DOCUMENTS

| | | | |
|---|---|---|---|
| WO | WO 97/37079 | * | 8/1998 |
| WO | WO 98/37079 | | 8/1998 |
| WO | WO 99/59980 | | 11/1999 |
| WO | WO 01/05783 | | 1/2001 |
| WO | WO 03/077656 A1 | | 9/2003 |
| WO | WO 2004/018435 A1 | | 3/2004 |
| WO | WO 2004/063192 A1 | | 7/2004 |
| WO | WO 2004/069829 A1 | | 8/2004 |

OTHER PUBLICATIONS

E. F. Elslager et al.: "Synthesis and Antimalarial Effects of 1-(3,4-Dichlorophenyl)-3-'4-')1-ethyl-3-plperidyl)amlno!-6-methyl-2-pyrimidinyl!guan idine and Related Substances", J. Med. Chem., vol. 17, No. 1, 1974, pp. 75-100, XP002297230, Table 1.

* cited by examiner

PYRIMIDINE DERIVATIVES AS IL-8 RECEPTOR ANTAGONISTS

CROSS REFERENCE TO RELATED APPLICATIONS

This application is a continuation-in-part of U.S. application Ser. No. 10/167,232, filed Jun. 11, 2002, now abandoned which was a continuation of U.S. application Ser. No. 09/616,496, filed Jul. 14, 2000, now abandoned which claimed priority from U.S. provisional application 60/144,160, filed Jul. 15, 1999. The entire disclosures of all are incorporated herein by reference.

FIELD OF THE INVENTION

The invention relates to chemical compounds containing the pyrimidine nucleus and their use to treat diseases and conditions related to inappropriate Interleukin-8 receptor activity.

BACKGROUND OF THE INVENTION

Interleukin-1 (IL-1), Interleukin-6 (IL-6), Interleukin-8 (IL-8) and Tumor Necrosis Factor (TNF) are cytokines which are involved in immunoregulation and other physiological conditions, such as inflammation. IL-1, IL-8, IL-6 and TNF affect a wide variety of cells and tissues, and these cytokines, as well as other leukocyte-derived cytokines, are inflammatory mediators of a wide variety of disease states and conditions.

Cytokine mediated diseases are diseases or conditions in which excessive or unregulated production of one or more cytokines occurs. Among diseases in which cytokines are implicated are rheumatoid arthritis, osteoarthritis, endotoxemia, toxic shock syndrome, other acute or chronic inflammatory diseases, such as the inflammatory reaction induced by endotoxin or inflammatory bowel disease; tuberculosis, atherosclerosis, muscle degeneration, cachexia, psoriatic arthritis, Reiter's syndrome, rheumatoid arthritis, gout, traumatic arthritis, rubella arthritis and acute synovitis.

Excessive or unregulated cytokine production has been implicated in mediating or exacerbating rheumatoid arthritis, rheumatoid spondylitis, osteoarthritis, gouty arthritis, and other arthritic conditions; sepsis, septic shock, endotoxic shock, gram negative sepsis, toxic shock syndrome, adult respiratory distress syndrome, cerebral malaria, chronic pulmonary inflammatory disease, silicosis, pulmonary sarcosis, bone resorption diseases, reperfusion injury, graft v. host rejection, allograft rejection, fever and myalgia due to infection, such as influeniza, cacliexia secondary to infection or malignancy, cachexia secondary to acquired immune deficiency syndrome (AIDS), AIDS related complex (ARC), keloid formation, scar tissue formation, Crohn's disease, ulcerative colitis and pyresis.

Interleukin-8 (IL-8) is a chemotactic factor first identified and characterized in 1987. Many different names have been applied to IL-8, such as neutrophil attractant/activation protein-1 (NAP-1), monocyte derived neutrophil chemotactic factor (MDNCF), neutrophil activating factor (NAF), and T-cell lymphocyte chemotactic factor. Like IL-1, IL-8 is produced by several cell types, including mononuclear cells, keratinocytes, macrophages, fibroblasts, endothelial and epithelial cells exposed to TNF, Il-1α, IL-1β or LPS, and by neutrophils themselves when exposed to LPS or chemotactic factors such as FMLP. Its production is induced by IL-1, TNF and by lipopolysaccharide (LPS). IL-8 stimulates a number of cellular functions in vitro. It is a chemoattractant for neutrophils, T-lymphocytes and basophils. It induces histamine release from basophils, causes lysozomal enzyme release and respiratory burst from neutrophils, and has been shown to increase the surface expression of Mac-1 (CD11b/CD 18) on neutrophils without de novo protein synthesis. This may contribute to increased adhesion of the neutrophils to vascular endothelial cells.

Two high affinity human IL-8 receptors (77% homology) have been characterized: IL-8Rα, which binds only IL-8 with high affinity, and IL-8Rβ, which has high affinity for IL-8 as well as for GROα, GROβ, GROγ and NAP-2.

There remains a need for treatment of conditions associated with an increase in IL-8 production (which is responsible for chemotaxis of neutrophil and T-cells subsets into the inflammatory site), utilizing compounds which are inhibitors of IL-8 receptor binding.

SUMMARY OF THE INVENTION

This invention provides for a method of treating a chemokine mediated disease in a mammal, wherein the chemokine is one which binds to an IL-8α or β receptor. According to the invention, compounds of the formula I antagonize cytokine activity, such that it is regulated down to treat, ameliorate or prevent the disease state. The method comprises administering to a mammal an effective amount of a compound of formula I:

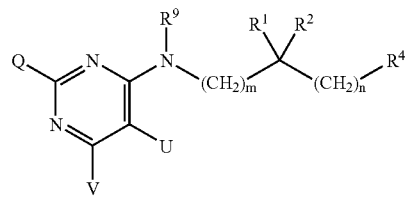

wherein

Q is chosen from hydroxyalkyl, unsubstituted and substituted aryl, unsubstituted and substituted heterocyclyl, $R^{12}OC(O)-(CH_2)_p-$, $R^{11}R^{12}NC(O)-$, $R^{11}C(O)NR^{12}-$, $R^{11}C(NH)NR^{12}-$, $R^{12}C(O)-$, $R^{11}OC(O)NR^{12}-$, $R^{11}NHC(O)NR^{12}-$ and HetB-Y-HetA-;

U is chosen from hydrogen, halogen, $(C_1-C_{20})$hydrocarbon and substituted $(C_1-C_{20})$alkyl;

V is chosen from hydrogen, halogen, $-R^3$, $-OR^3$, and $-SR^3$;

HetA is aryl or heterocyclyl;

Y is $-CH_2-$, a direct bond or $-O-$;

HetB is aryl or heterocyclyl, with the proviso that when HetA is imidazole, Y is a direct bond and $V^a$ is hydrogen, $(C_1-C_6)$alkyl or $(C_1-C_6)$alkoxy, HetB cannot be benzofuran, indole, benzothiophene or substituted benzofuran, indole or benzothiophene;

$R^1$ is chosen from alkyl, cycloalkyl, aryl, heterocyclyl, $-(C_1-C_4)$alkylaryl, and $-(C_1-C_4)$-alkylheterocyclyl;

$R^2$ is H or $(C_1-C_4)$alkyl;

$R^3$ is chosen from $(C_1-C_{20})$hydrocarbon, substituted $(C_1-C_{20})$alkyl, and $[(C_1-C_{20})$alkyl$]R^7$;

$R^4$ is $A^1$ or $A^2$;

$A^1$ is chosen from —C(O)NR$^5$R$^6$, —C(O)OR$^5$, and

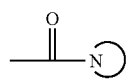

$A^2$ is chosen from R$^8$C(O)NH—, R$^5$R$^6$N—, and R$^5$O—, with the proviso that, when m and n are both zero, R$^4$ cannot be A$^2$;

is a 5-, 6- or 7-membered nitrogen heterocycle attached to the carbonyl of A$^1$ via nitrogen;

R$^5$ is chosen from aryl, heterocyclyl, -(heterocyclyl)-R$^{10}$, —CH$_2$C(O)NHalkyl, —[(C$_2$–C$_{10}$)hydrocarbon]-R$^{10}$ and -[monosubstituted (C$_2$–C$_{10}$-alkyl)]-R$^{10}$;

R$^6$ is H or C$_1$–C$_6$-alkyl; or

R$^1$ and R$^6$ taken together form a 5-, 6- or 7-membered nitrogen heterocycle;

R$^7$ is chosen from aryl, substituted aryl, aryloxy, substituted aryloxy, arylthio, substituted arylthio, heteroaryloxy, substituted heteroaryloxy, heteroarylthio, substituted heteroarylthio, heterocyclyl, and substituted heterocyclyl;

R$^8$ is chosen from alkyl, aryl, substituted alkyl, —(C$_1$–C$_4$)alkylaryl, and —(C$_1$–C$_4$)-alkylheterocyclyl;

R$^9$ is chosen from H, C$_1$–C$_6$-alkyl and aryl;

R$^{10}$ is chosen from H, F, alkyl, fluoroalkyl, —O-alkyl, —O-(substituted)alkyl, oxaalkyl, —S-alkyl, —SO-alkyl, —SO$_2$-alkyl, —CH$_2$O-alkyl, —CH$_2$S-alkyl, —CH$_2$SO-alkyl, —CH$_2$SO$_2$-alkyl, —N(loweralkyl)O-loweralkyl, aryl, and heterocyclyl;

R$^{11}$ is chosen from H, C$_1$–C$_6$-alkyl, cycloalkyl, aryl and substituted-C$_1$–C$_6$-alkyl;

R$^{12}$ is H or C$_1$–C$_6$-alkyl;

m is zero or one;

n is zero or one; and p is zero or 1–6.

The compounds of formula I can be used in the manufacture of a medicament for the prophylactic or therapeutic treatment of disease states in mammals, which are exacerbated or caused by excessive or unregulated cytokine production, more specifically IL-1, IL-8 or TNF production, by cells of the mammal, such as, but not limited to, monocytes and/or macrophages. Chemokine mediated diseases treatable with compounds of the invention include: septic shock, endotoxic shock, gram negative sepsis or toxic shock syndrome; bone resorption disease, graft versus host reaction, atherosclerosis, arthritis, osteoarthritis, rheumatoid arthritis, gout, psoriasis, atopic dermatitis or a topical inflammatory disease state; adult respiratory distress syndrome, asthma or chronic obstructive pulmonary disease; cardiac or renal reperfusion injury, thrombosis or glomerulonephritis; Crohn's disease, ulcerative colitis or inflammatory bowel disease; cachexia and viral infections. The compounds may also be used to treat inflammations, stroke and Alzheimer's disease.

In another aspect, the invention relates to novel compounds falling within the genus of formula I.

In another aspect, the invention relates to pharmaceutical compositions comprising pharmaceutically acceptable carriers and compounds falling within the genus of formula I.

DETAILED DESCRIPTION OF THE INVENTION

As stated above, compounds of the formula I are useful in treating cytokine mediated diseases. The generic concept of the invention is encompassed by three overlapping subgenera of compounds, which are themselves novel. The first of these is the subgenus II:

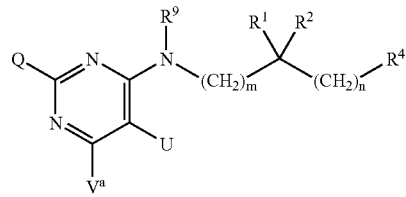

II in which $V^a$ is chosen from —R$^3$, —OR$^3$ and —SR$^3$. In this, and in all subsequent formulae, the variables are defined when they are introduced, and they retain that definition throughout the specification. The second subgenus of novel compounds is represented by formula III:

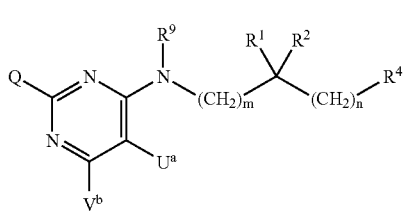

III in which $U^a$ is chosen from halogen, (C$_1$–C$_{20}$)hydrocarbon and substituted (C$_1$–C$_{20}$)alkyl and $V^b$ is chosen from hydrogen and halogen. The third subgenus of novel compounds is represented by formula IV:

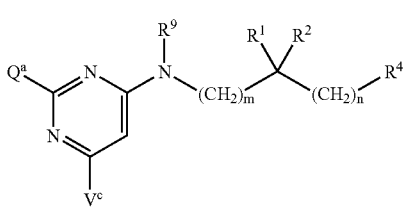

IV in which $Q^a$ is chosen from hydroxyalkyl, unsubstituted and substituted aryl, unsubstituted heterocyclyl other than unsubstituted imidazole and unsubstituted triazole, substituted heterocyclyl, R$^{12}$OC(O)—(CH$_2$)$_p$—, R$^{11}$R$^{12}$NC(O)—, R$^{11}$C(O)NR$^{12}$, R$^{11}$C(NH)NR$^{12}$—, R$^{12}$C(O)—, R$^{11}$OC(O)NR$^{12}$—, R$^{11}$NHC(O)NR$^{12}$— and HetB-Y-HetA-; $V^c$ is chosen from hydrogen, halogen and R$^{3a}$; and R$^{3a}$ is (C$_1$–C$_8$) alkyl.

The method aspect of the invention envisions the use of any and all compounds falling within the genus of formula I. However, due to the peculiarities of patent law, and having nothing whatever to do with the scope of the inventors' conception of the invention, certain compounds appear from a preliminary search of the literature ineligible to be claimed per se. Thus, for example, N-[3-(methylsulfonyl)propyl]-α-[[6-chloro-2-(1H-imidazol-1-yl)pyrimidin-4-yl]amino]benzenepropanamide, while it would be part of the inventive concept, has been excluded from the claims to compounds. It may be found upon examination that certain members of the excluded genera are patentable to the inventors in this application or that additional species and genera not presently excluded are not patentable to the inventors in this application. In either case, the exclusion of species and genera in applicants' claims are to be considered artifacts of patent prosecution and not reflective of the inventors' concept or description of their invention, which encompasses all compounds falling within the genus of formula I that are not already in the possession of the public.

One preferred subgenus of compounds is that in which Q is HetB-Y-HetA-. Among these compounds, HetA is preferably chosen from the group consisting of phenyl, piperazine, imidazole, pyridine, furan, and substituted phenyl, piperazine, imidazole, pyridine and furan. HetB is preferably chosen from the group consisting of aryl and heteroaryl, particularly phenyl, furan thiophene, benzodioxole, benzodioxane, benzofuran, dihydrobenzofuran, benzoxazole, benzimidazole, benzothiazole, benzothiophene and substituted phenyl, furan, thiophene, benzodioxole, benzodioxane, benzofuran, dihydrobenzofuran, benzoxazole, benzimidazole, benzothiazole and benzothiophene. In preferred embodiments, the substituent at the 6-position (which is generically V and in specific embodiments is $V^a$, $V^b$ or $V^c$) is hydrogen, $R^3$ or $OR^3$ and $R^3$ is ($C_1$ to $C_6$)hydrocarbon or substituted ($C_1$ to $C_6$)alkyl; HetA is chosen from the group consisting of phenyl, imidazole, methylimidazole, pyridine, furan, hexahydrodiazepine, piperidine, methylpiperazine and piperazine; and HetB is chosen from the group consisting of phenyl, benzodioxane, benzodioxole, dihydrobenzofuran, benzofuran, benzothiazole, pyridine, furan, thiophene, benzothiophene, chroman, dihydrochroman and substituted phenyl, benzodioxole, pyridine and furan. Another preferred embodiment is that in which $V^a$ or $V^b$ is hydrogen or $R^3$; and U or $U^a$ is halogen.

Another preferred subgenus is that in which Q or $Q^a$ is chosen from substituted benzimidazole, substituted pyridine, substituted phenyl, naphthylene, benzodioxole, benzooxadiazole, quinoline, substituted quinoline, benzofuran, substituted benzofuran, chroman, dihydrochroman, and tetrahydropyrazino [1,2-a]indole. As in the preceding subgenus, preferred embodiments are those in which the substituent at the 6-position (which is generically V and in specific embodiments is $V^a$, $V^b$ or $V^c$) is hydrogen, $R^3$ or $OR^3$ and $R^3$ is ($C_1$ to $C_6$)hydrocarbon or substituted ($C_1$ to $C_6$)alkyl. Another preferred embodiment is that in which $V^a$ or $V^b$ is hydrogen or $R^3$; and U or $U^a$ is halogen.

Another major subgenus includes compounds of formula V:

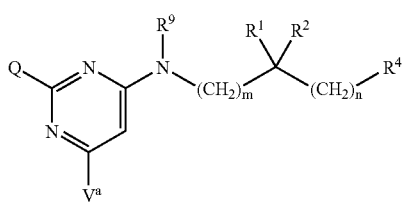

V (which is formula II in which U=hydrogen) wherein Q is chosen from hydroxyalkyl, aryl, heterocyclyl, substituted heterocyclyl, $R^{12}OC(O)—(CH_2)_p—$, $R^{11}R^{12}NC(O)—$, $R^{11}C(O)NR^{12}—$, $R^{11}C(NH)NR^{12}—$, $R^{12}C(O)—$, $R^{11}OC(O)NR^{12}—$ and $R^{11}NHC(O)NR^{12}$; $R^3$ is chosen from ($C_1$–$C_{20}$)hydrocarbon, substituted ($C_1$–$C_{20}$)alkyl, —[($C_1$–$C_{20}$)alkyl]substituted aryl, —[($C_1$–$C_{20}$)alkyl]substituted aryloxy, —[($C_1$–$C_{20}$)alkyl] substituted arylthio, —[($C_1$–$C_{20}$)alkyl] substituted heteroaryloxy, —[($C_1$–$C_{20}$) alkyl] substituted heteroarylthio, and —[($C_1$–$C_{20}$)alkyl]heterocyclyl; and $R^{10}$ is chosen from H, alkyl, —O-alkyl, —S-alkyl, —SO-alkyl, —$SO_2$-alkyl, —$CH_2$O-alkyl, —$CH_2$S-alkyl, —$CH_2$SO-alkyl, —$CH_2SO_2$-alkyl, aryl, and heterocyclyl.

In preferred embodiments of this subgenus, $A^1$ is chosen from —C(O)$NR^{5a}R^6$, —C(O)$OR^{5a}$, and

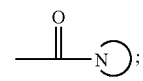

$R^{5a}$ is chosen from saturated heterocyclyl, -(heterocyclyl)-$R^{10}$, —$CH_2C(O)$NHalkyl, —($C_2$–$C_{10}$-hydrocarbon)-$R^{10a}$, -(monosubstituted $C_2$–$C_{10}$-alkyl)-$R^{10a}$ and —($C_4$–$C_8$-hydrocarbon)-$R^{13}$; $R^{8a}$ is chosen from alkyl, —($C_4$)alkylaryl, —($C_1$–$C_4$)-alkylheterocyclyl and substituted alkyl other than —($C_1$–$C_3$)-alkyl substituted with aryl; $R^{10a}$ is chosen from —)-alkyl, —S-alkyl, —SO-alkyl, —$SO_2$-alkyl, —$CH_2$O-alkyl, —$CH_2$S-alkyl, —$CH_2$SO-alkyl, —$CH_2SO_2$-alkyl; and $R^{13}$ is chosen from H, alkyl, aryl, and heterocyclyl.

Other preferred embodiments of subgenus V include compounds in which Q is chosen from hydroxyalkyl, aryl, substituted heterocyclyl, $R^{12}OC(O)—(CH_2)_p—$, $R^{11}R^{12}NC(O)—$, $R^{11}C(O)NR^{12}—$, $R^{11}C(NH)NR^{12}—$, $R^{12}C(O)—$, $R^{11}OC(O)NR^{12}—$, $R^{11}NHC(O)NR^{12}—$ and heterocyclyl other than 1-imidazolyl and 1-triazolyl. Other embodiments of formula V are those in which Q is heteroaryl, particularly 1-imidazolyl, 4-substituted-1-imidazolyl, and 1-benzimidazolyl and $V^a$ is $R^3$, $OR^3$ or $SR^3$, in which $R^3$ is preferably ($C_1$–$C_{20}$)hydrocarbon, substituted ($C_1$–$C_{20}$)alkyl or substituted aryl[($C_1$–$C_{20}$)alkyl]; more preferably $V^a$ is $R^3$. $R^9$ is preferably hydrogen or methyl; m and n are zero; $R^2$ is H; and $R^4$ is —C(O)$NHR^5$. In these compounds $R^5$ is —($C_2$–$C_{10}$-hydrocarbon)-$R^{10}$ or -(heterocyclyl)-$R^{10}$ and $R^{10}$ is —S-loweralkyl or —O-loweralkyl; alternatively $R^5$ is

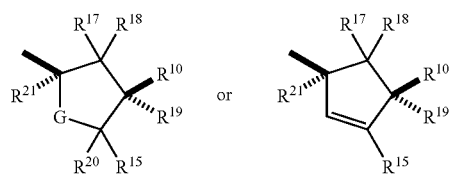

and G is chosen from —$CH_2$—, and —$C(R^{22}R^{23})$—, and $R^{15}$, $R^{17}$, $R^{18}$, $R^{19}$, $R^{20}$, $R^{21}$, $R^{22}$, and $R^{23}$ are independently chosen from hydrogen and lower alkyl.

Other preferred embodiments of formula V are those in which Q is chosen from 1-imidazolyl, 4-substituted-1-imidazolyl, 1-benzimidazolyl, 3-quinolinyl, 3-pyridinyl, and 5-(or 6-)methyl-1-benzimidazolyl; $R^9$ is hydrogen or methyl; m and n are zero; $R^1$ is chosen from n-propyl, isopropyl, n-butyl, isobutyl, isopentyl, cyclohexyl and cyclohexylmethyl; $R^2$ is H; $R^3$ is chosen from ($C_4$–$C_{14}$) hydrocarbon, ω-phenoxy($C_2$–$C_4$)alkyl, ω-phenylthio ($C_2$–$C_4$)alkyl and substituted phenoxy[($C_2$–$C_4$)alkyl]; $R^4$ is —C(O)NHR$^5$; $R^5$ is —($C_2$–$C_7$-hydrocarbon)-$R^{10}$; and $R^{10}$ is —S-loweralkyl or —O-loweralkyl. Among these compounds, preferred embodiments are those wherein the stereogenic center to which $R^1$ and $R^2$ are attached is of the S absolute configuration.

Compounds in which Q is 4-substituted-1-imidazolyl are generally preferred, as are those in which $V^a$ is $R^3$. Preferred substituents at 4 ($V^a$) include lower alkyl and perfluoro lower alkyl. $R^3$ is preferably chosen from ($C_1$–$C_{20}$)hydrocarbon, substituted ($C_1$–$C_{20}$)alkyl and [($C_1$–$C_{20}$)alkyl] substituted aryl. A preferred subgenus includes all compounds in which the substituent at 6 (V, $V^a$, $V^b$ or $V^c$) is ($C_1$ to $C_6$)hydrocarbon or substituted ($C_1$ to $C_6$)alkyl (in the case of V, $V^a$ and $V^b$).

Exemplary cyclic $R^5$'s from the subgenus in which $R^5$ is

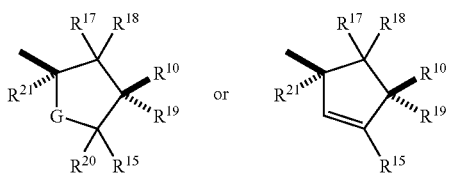

include:

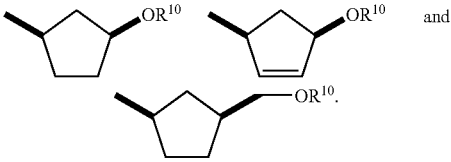

Most preferred are those in which $R^5$ is

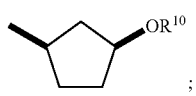

;

V is $R^3$ and Q is heterocyclyl or substituted heterocyclyl. As indicated above, when $R^5$ is cyclic, the cis diastereomer is preferred, and within that pair of isomers, it will usually be advantageous to employ a single enantiomer.

Most of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers are prepared as described below using chiral synthons or chiral reagents, or resolved using conventional techniques. When a specific chirality is intended, it is indicated by the conventional wedge and dash notation; a simple single bond emanating from a chiral center implies no particular stereochemistry. The graphic representations of racemic, ambiscalemic and scalemic or enantiomerically pure compounds used herein are taken from Maehr *J. Chem. Ed.* 62, 114–120 (1985): solid and broken wedges are used to denote the absolute configuration of a chiral element; wavy lines indicate disavowal of any stereochemical implication which the bond it represents could generate, solid and broken bold lines are geometric descriptors indicating the relative configuration shown but denoting racemic character; and wedge outlines and dotted or broken lines denote enantiomerically pure compounds of indeterminate absolute configuration. Usually compositions of the invention will be primarily single enantiomers at the point of attachment of $R^1$ and $R^2$. When the compounds described herein contain olefinic double bonds or other centers of geometric asymmetry, and unless specified otherwise, it is intended that the compounds include both E and Z geometric isomers. Likewise, all tautomeric forms are also intended to be included.

Compounds of formula I inhibit proinflammatory cytokines, such as IL-1, IL-8 and TNF and are therefore useful for treating inflammation diseases such as rheumatoid arthritis, rheumatoid spondylitis, osteoarthritis, gouty arthritis and other arthritic conditions. The compounds of formulae I-V may be used to treat other disease states mediated by excessive or unregulated TNF production. Such diseases include, but are not limited to sepsis, septic shock, endotoxic shock, gram negative sepsis, toxic shock syndrome, adult respiratory distress syndrome, cerebral malaria, chronic pulmonary inflammatory disease, silicosis, pulmonary sarcoidosis, bone resorption diseases, such as osteoporosis, reperfusion injury, graft vs. host rejection, allograft rejections, fever and myalgias due to infection, such as influenza, cachexia secondary to infection or malignancy, cachexia, secondary to acquired immune deficiency syndrome (AIDS), AIDS, ARC (AID's related complex), keloid formation, scar tissue formation, Crohn's disease, ulcerative colitis, pyresis, inflammatory bowel disease; tuberculosis, atherosclerosis, muscle degeneration, psoriatic arthritis, Reiter's syndrome, AIDS and other viral infections, such as cytomegalia virus (CMV), influenza virus, and the herpes family of viruses such as Herpes Zoster or Simplex I and II, adult respiratory distress syndrome, thrombosis and glomerulonephritis. Recent evidence also links IL-1 activity to diabetes.

The compounds of formulae I-V may also be used topically in the treatment of inflammations such as for the treatment of eczema, psoriasis, sunburn and other inflammatory skin conditions; inflammatory eye conditions including conjunctivitis; and pain associated with inflammation.

Definitions

"Alkyl" is intended to include linear, cyclic or branched hydrocarbon structures and combinations thereof; hydrocarbons of 20 or fewer carbons are generally preferred. "Lower alkyl" means alkyl groups of from 1 to 6 carbon atoms. Examples of lower alkyl groups include methyl, ethyl, propyl, isopropyl, butyl, s-and t-butyl, pentyl, hexyl, and the like.

"Cycloalkyl" is a subset of alkyl and includes cycloalkyl groups of from 3 to 12 carbon atoms; the term is not restricted to single ring structures; it includes monocyclic, polycyclic and fused residues. Examples of "cycloalkyl" groups include c-propyl, c-butyl, c-pentyl, c-hexyl, 2-methylcyclopropyl, cyclopropylmethyl, cyclopentylmethyl, norbornyl, adamantyl, myrtanyl and the like.

"Oxaalkyl" refers to alkyl residues in which one or more carbons has been replaced by oxygen. Examples include methoxypropoxy, 3,6,9-trioxadecyl and the like.

"Alkenyl" refers to a $C_2$ to $C_{20}$ hydrocarbon of a linear, branched, or cyclic ($C_5$–$C_6$) configuration, and combinations thereof, having one or two degrees of unsaturation. $C_2$–$C_8$ Alkenes are preferred. Examples of alkenyl groups include vinyl, allyl, isopropenyl, pentenyl, hexenyl, c-hexenyl, 1-propenyl, 2-butenyl, 2-methyl-2-butenyl, 2,4-hexadienyl and the like.

"Alkynyl" is $C_2$–$C_8$ alkynyl of a linear or branched configuration and combinations thereof. Examples of alkynyl groups include ethyne, propyne, butyne, pentyne, 3-methyl-1-butyne, 3,3-dimethyl-1-butyne, and the like.

$C_1$ to $C_{20}$ Hydrocarbon includes alkyl, cycloalkyl, alkenyl, alkynyl aryl and combinations thereof. Examples include phenethyl, cyclohexylmethyl and naphthylethyl.

"Alkoxy" means alkoxy groups of from 1 to 6 carbon atoms of a straight, branched, cyclic configuration and combinations thereof. Examples of alkoxy groups include methoxy, ethoxy, propoxy, isopropoxy, cyclopropyloxy, cyclohexyloxy, and the like.

Acyl refers to groups of from 1 to 8 carbon atoms of a straight, branched, cyclic configuration, saturated, unsaturated and aromatic and combinations thereof, attached to the parent structure through an carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Halogen includes F, Cl, Br, and I, with F and Cl as the preferred groups. "Halophenyl" means phenyl substituted by 1–5 halogen atoms. Halophenyl includes pentachlorophenyl, pentafluorophenyl, and 2,4,6-trichlorophenyl. "Fluoroalkyl" refers to an alkyl residue in which one or more hydrogen atoms are replaced with F, for example: trifluoromethyl, difluoromethyl, pentafluoroethyl and 2,2,2-trifluoroethyl.

"Aryl" and "heteroaryl" mean a 5- or 6-membered aromatic or heteroaromatic ring containing 0–3 heteroatoms selected from O, N, and S; a bicyclic 9- or 10-membered aromatic or heteroaromatic ring system containing 0–3 heteroatoms selected from O, N, and S; or tricyclic 13- or 14-membered aromatic or heteroaromatic ring system containing 0–3 heteroatoms selected from O, N, and S; each of which rings is optionally substituted with up to three substituents chosen independently from lower alkyl, =O, nitro, halogen, hydroxy, alkoxy, alkylsulfonyl; methylenedioxy, alkoxyethoxy, cyano, amino, alkylamino, dialkylamino, acylamino, aminosulfonyl, $C_1$–$C_6$-alkoxycarbonyl, carboxy, methylsulfonamido, perfluoroalkyl, phenyl, benzyl, trityl, and phenoxy. Six to fourteen-membered aryl residues include, for example, benzene and naphthalene, and the 5- to 10-membered heteroaryl residues include, for example, imidazole, pyridine, indole, oxazole, thiophene, benzopyranone, benzodioxan, benzodioxole, benzofuran, benzothiophene, chroman, benzothiazole, oxadiazole, benzooxadiazole, thiazole, furan, benzimidazole, quinoline, isoquinoline, quinoxaline, pyrimidine, pyrimidinone, pyridazine, tetrazole, and pyrazole.

"Arylalkyl" and "alkylaryl" denote an aryl residue attached to the parent structure through an alkyl residue. The alkyl need not be straight chain. Examples include benzyl, phenethyl, 2-phenylpropyl, 4-chlorobenzyl, and the like. The alkyl may even be a fused cycloalkyl such as indan (e.g. indan-2-yl), tetralin, and fluorene (e.g fluoren-9-yl). "Heteroarylalkyl" denotes a residue comprising an alkyl attached to a heteroaryl ring such as pyridinylmethyl, pyrimidinylethyl, and the like.

"Heterocyclyl" means a cycloalkyl where one to three carbon atoms is replaced with a heteroatom, such as O, NR (R=H, alkyl), N→O, S, SO, $SO_2$ and the like. As before, the term is not restricted to single ring structures; it includes monocyclic, polycyclic and fused residues in which one or more rings is optionally substituted with up to three substituents chosen independently from lower alkyl, =O, halogen, hydroxy, alkoxy, amino, alkylamino, alkylthio, dialkylamino, acylamino, aminosulfonyl, $C_1$–$C_6$-alkoxycarbonyl, carboxy, methylsulfonamido, fluoroalkyl, phenyl, benzyl, trityl, and phenoxy. When two heteroatoms are separated by a single carbon in a saturated hetereocycle, the resulting heterocycloalkyls tend to be unstable in aqueous solutions and are therefore not preferred. Heterocyclyl includes heteroaryl, which is a subset of heterocyclyl. Examples of heterocycloalkyls include: pyrrolidine, morpholine, tetrahydrofuran, tetrahydropyran, piperidine, piperazine, pyridine-N-oxide, 2-methyl-1,3-dithiane, dioxane, hexahydrodiazepine, tetrahydropyrazino[1,2-a]indole and the like.

"Substituted" alkyl, alkenyl, cycloalkyl, aryl, heteroaryl or heterocycloalkyl means alkyl, alkenyl, cycloalkyl, aryl, heteroaryl or heterocycloalkyl, wherein hydrogen atoms are replaced by halogen, hydroxy, carboxy, carboalkoxy, carboxamido, cyano, alkylcarbonyl (acyl), nitro, alkoxy, methylenedioxy, alkoxymethyl, alkoxyethoxy, amino, alkylamino, dialkylamino, acylamino, aminosulfonyl, $C_1$–$C_6$-alkoxycarbonyl, $C_1$–$C_6$-alkylaminocarbonyl, trialkylsilyl, methylsulfonamido, methylsulfonyl, alkylthio, fluoroalkyl, phenyl, benzyl, trityl, phenoxy, alkylphenoxy, amidino, guanidino, ureido, and benzyloxy. When a carbon of an alkyl, alkenyl, cycloalkyl, aryl, heteroaryl or heterocycloalkyl bears two hydrogen atoms, the two hydrogens may be replaced by =O, =S or =NH.

The generic description of the invention is intended to encompass all of the examples set forth herein. If any ambiguity is asserted as to whether a generic or descriptive term used in the application should be construed so as to encompass a specific example, the putative ambiguity should be resolved in favor of the genus including the actual example.

Abbreviations

The following abbreviations and terms have the indicated meanings throughout:

Ac=acetyl
BNB=4-bromomethyl-3-nitrobenzoic acid
Boc=t-butyloxy carbonyl
Bu=butyl
c-=cyclo
DBU=diazabicyclo[5.4.0]undec-7-ene
DCM=dichloromethane=methylene chloride=$CH_2Cl_2$
DEAD=diethyl azodicarboxylate
DIC=diisopropylcarbodiimide
DIEA=N,N-diisopropylethyl amine
DMAP=4-N,N-dimethylaininopyridine
DMF=N,N-dimethylformamide
DMSO=dimethyl sulfoxide
DVB=1,4-divinylbenzene
EEDQ=2-ethoxy-1-ethoxycarbonyl-1,2-dihydroquinoline
Fmoc=9-fluorenylmethoxycarbonyl
GC=gas chromatography
HATU=O-(7-Azabenzotriazol-1-yl)-1,1,3,3-tetramethyluronium hexafluorophosphate
HOAc=acetic acid
HOBt=hydroxybenzotriazole
Me=methyl
mesyl=methanesulfonyl
MTBE=methyl t-butyl ether
NMO=N-methylmorpholine oxide
PEG=polyethylene glycol
Ph=phenyl PhOH=phenol
PfP=pentafluorophenol
PPTS=pyridinium p-toluenesulfonate
PyBroP=bromo-tris-pyrrolidino-phosphonium hexafluorophosphate
rt or RT=room temperature
sat'd or sat.=saturated
s-=secondary t-=tertiary
TBDMS=t-butyldimethylsilyl
TFA=trifluoroacetic acid
THF=tetrahydrofuran
TMOF=trimethyl orthoformate
TMS=trimethylsilyl
tosyl=p-toluenesulfonyl
Trt=triphenylmethyl

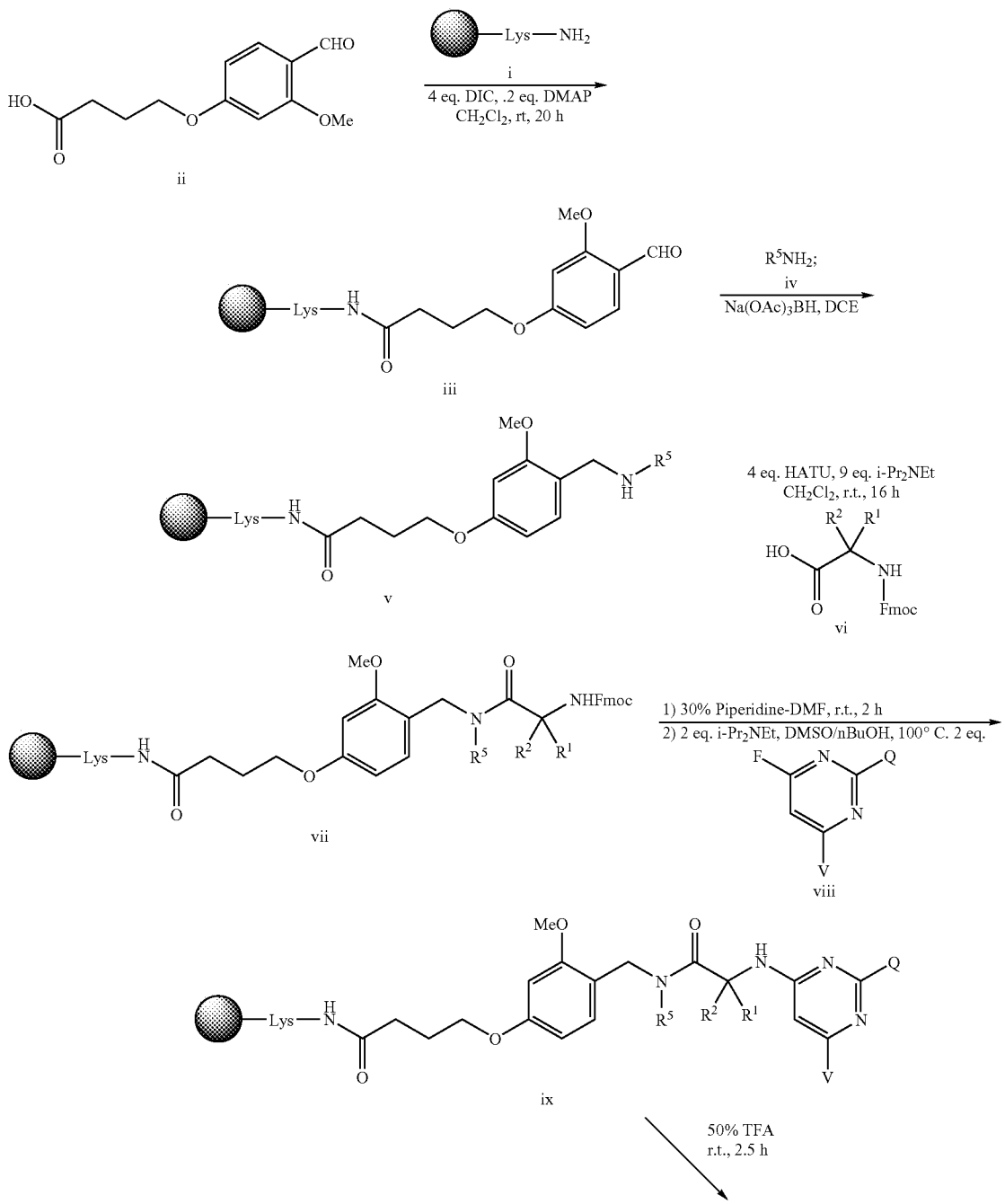

Scheme 1
Generic Solid Phase Synthesis

-continued

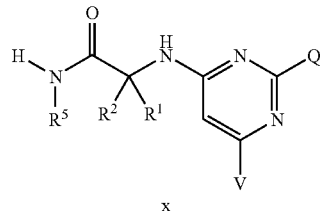

x

Scheme 1 depicts a generic synthesis of compounds of the invention. Amino flnctionalized TENTAGEL™ resin i (10 g 5.2 mmole) was suspended in 50 mL of $CH_2Cl_2$ and treated with 3.73 g of linker acid ii (15.6 mmole), 3.25 mL of DIC (20.8 mmole), and 63 mg of DMAP (0.52 mmole). After 48 h at room temperature, 3.77 g of linker acid ii, 3.25 mL of DIC and 2.1 g HOBt were added. The mixture was shaken at room temperature for 17 h and then washed with DMF twice, $CH_2Cl_2$ ten times to give resin iii. The resin iii is treated with amine $R^5NH_2$ iv and $Na(OAc)_3BH$ in dichloroethane at room temperature for 36 h then washed with methanol 5 times and methylene chloride 5 times to give resin-bound amine v. The amine is coupled with an N-Fmoc amino acid (vi) by treatment with HATU and i-$Pr_2NEt$ in methylene chloride at room temperature for 48 h to provide resin vii. Fmoc on resin vii is removed by treatment with 30% piperidine in DMF and the resulting resin-bound amine is reacted with fluoropyrimidine viii, i-$Pr_2NEt$ in DMSO: nBuOH (1:1) at 100° C. for 18 h and then washed with methanol, $CH_2Cl_2$ to give resin bound product ix. The final product is cleaved off resin by treatment with TFA for 3 h to give product x.

The fluoropyrimidine viii is prepared by stirring together 1 equivalent of the appropriate 2-heteroaryl-4,6-difluoropyrimidine (e.g. 2-imidazolyl-4,6-difluoropyrimidine) and 1 equivalent of an alkali metal salt of the alkylmercaptan corresponding to V in an inert solvent such as DMF at elevated temperature (e.g. 50–80° C.) for a suitable period of time, then cooling to room temperature. The reaction is diluted with ethyl acetate and washed with saturated $NH_4Cl$, $H_2O$, brine, dried over $MgSO_4$ and concentrated. The crude product is purified by flash chromatography eluted with EtOAc:hexanes:MeOH.

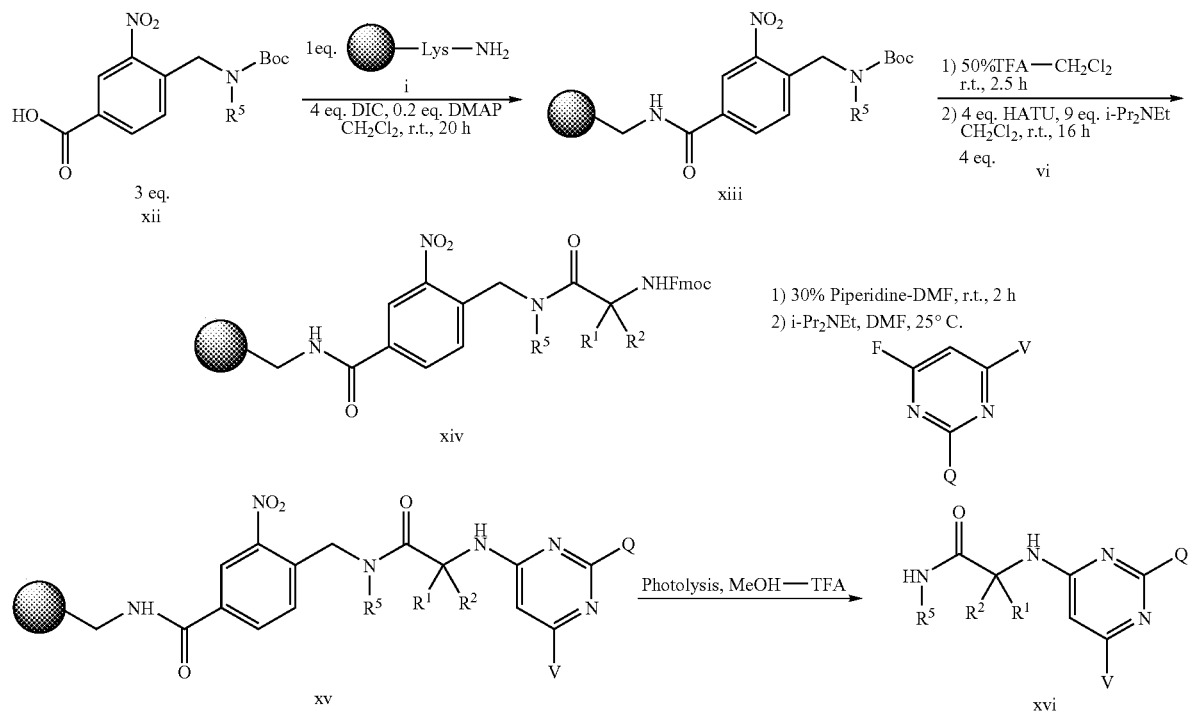

Scheme 2

Scheme 2 depicts a similar synthesis to that of Scheme 1, except the linker is photolytically cleavable instead of acid cleavable. As shown in Scheme 2, 2.5 g of amino functionalized TENTAGEL™ resin i (0.70 mmole) was suspended in 10 mL of $CH_2Cl_2$ and treated with linker acid xii (2.1 mmole), 0.44 mL of DIC (2.8 mmole), and 17 mg of DMAP (0.14 mmole). The mixture was shaken at room temperature for 17 h and then washed with $CH_2Cl_2$ ten times to give resin xiii.

Resin xiii is treated with 50% TFA-CH$_2$Cl$_2$ at room temperature for 1.5 h and then washed with CH$_2$Cl$_2$ ten times, 15% Et$_3$N—CH$_2$Cl$_2$ for 10 min, and CH$_2$Cl$_2$ for 5 times. The deprotected resin is suspended in 12 mL of CH$_2$Cl$_2$ and treated with 4 equivalents of N-Fmoc-amino acid vi, 4 equivalents of HATU and 9 equivalents of i-Pr$_2$NEt. The mixture is shaken for 19 h at ambient temperature and then washed 5 times to give resin xiv. The protecting Fmoc on resin xiv is removed by treatment with 30% piperidine in DMF and the resulting resin-bound amine is reacted with 2 equivalents of the appropriate 2-Q-4-V-6-fluoropyrimidine, 6 equivalents of i-Pr$_2$NEt in DMF at 23° C. for 17 h and then washed with DMF, CH$_2$Cl$_2$ to give resin xv. The final product x is cleaved from the resin by photolysis in MeOH for 17 hours. The product may be purified as above by flash chromatography eluting with EtOAc:hexanes:MeOH.

A specific embodiment of a solution phase synthesis is shown in Scheme 3 below as applied to a 6-chloro-2-(4-methyl-1-imidazolyl)-4-pyrimidinamine that incorporates the residue of L-norleucine butylamide:

Scheme 3

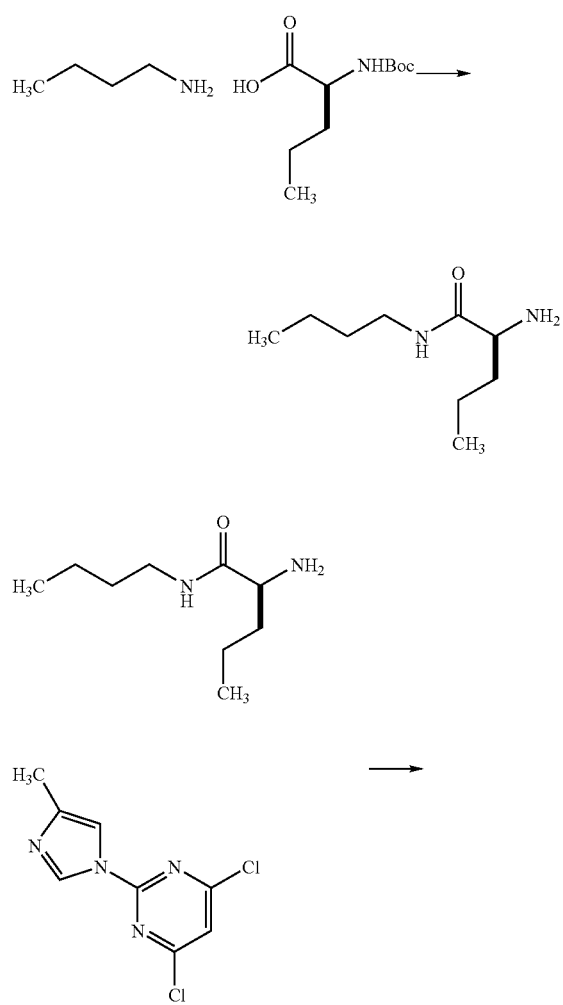

-continued

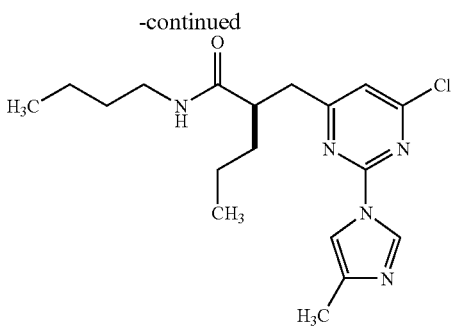

One equivalent of isobutylchloroformate is added to a solution of N-Boc-L-norleucine and one equivalent of a base such as N-methylmorpholine in THF at 0°C. After two minutes, one equivalent of butylamine is added and the mixture allowed to warm to room temperature. After thirty minutes, the reaction mixture is passed through a bed of Celite and all volatiles are removed under reduced pressure to yield N-Boc-L-norleucine butylamide.

The N-Boc-L-norleucine butylamide in methanol is treated with acetyl chloride. After 45 minutes, all volatiles are removed under reduced pressure to yield L-norleucine butylamide hydrochloride.

4-Methylimidazole (11.45 g, 140 mmol) was added in one portion to a solution of trichloropyrimidine in (2.47 g, 135 mmol) and triethylamine (30 mL, 216 mmol) in THF (500 mL). After 16 hrs, the reaction mixture was poured into saturated, aqueous ammonium chloride and extracted three times with ethyl acetate. The combined organic layers were washed with brine and dried over MgSO$_4$. The reaction mixture was filtered and all volatiles were removed under reduced pressure. 2-(4-methylimidazolyl)-4,6-dichloropyrimidine was isolated by flash chromatography (15% ethyl acetate in hexane) as an off-white solid.

Two equivalents of L-norleucine butylamiide hydrochloride are added to a solution of one equivalent of 2-(4-methylimidazolyl)-4,6-dichloropyrimidine and three equivalents of triethylamine in THF. After the reaction is complete, all volatiles are removed under reduced pressure and the product is isolate by flash chromatography (ethyl acetate).

Another specific example of the synthesis, applied to a compound of formula I in which R$^9$ is —CH$_3$ and R$^4$ is —C(O)NHR$^5$, is provided: Isobutyl chloroformate (226 mL, 1.73 mmol) was added to a solution of N-Boc sarcosine (1.73 mmol) and N-methyl morpholine (192 mL, 1.73 mmol) in THF. After two minutes, piperonylamine (216 mL, 1.73 mmol) was added and the mixture allowed to warm to room temperature. After thirty minutes, the reaction mixture was passed through a bed of Celite and all volatiles were removed under reduced pressure to yield N-Boc sarcosine piperonyl amide (531 mg, 95%) as a white solid. [$^1$H NMR: (CDCl$_3$) δ 2.41, 3H, s; 3.28, 2H, s; 4.39, 2H, d; 5.95, 2H, s; 6.80, 3H, m; 7.43, 1H, bs; 9.04, 1H, bs.]

N-Boc sarcosine piperonylamide (500 mg, 1.54 mmol) in methanol (10 mL) was treated with acetyl chloride (1 mL). After 45 minutes, all volatiles were removed under reduced pressure to yield sarcosine piperonyl amide hydrochloride (395 mg, quant.) as a sticky solid.

Sarcosine piperonyl amide hydrochloride (50 mg, 0.19 mmol) was added to a solution of 2-imidazolyl-4,6-dichloropyrimidine (II) (20 mg, 0.093 mmol) and Hünig's base (50 mL, 0.29 mmol) in THF (1 mL). After 16 hrs, all volatiles were removed and the product was isolated as a waxy solid (29 mg, 78%). [$^1$H NMR (CDCl$_3$) δ 3.2, 3H, s;4.25, 2H, s; 4.38, 2H, s;5.88, 2H, s; 6.30, 1H, bs; 6.42, 2H, bs; 6.65, 3H, m; 7.05, 1H, s; 8.40, 1H, s.]

The 6-chloro substituent may be replaced with the appropriate substituent V by reaction with the anion of V, e.g. R$^3$—, R$^3$S—, or R$^3$O—.

A specific embodiment of an alternative synthesis is shown in Scheme 4 below as applied to a 6-chloro-2-(4-pyridyl)-4-pyrimidinamine that incorporates the residue of L-leucine 3-methoxypropylamide:

Isobutyl chloroformate (520 μL, 4.0 mmol) was added to a solution of N-Boc leucine monohydrate (1.0 g, 4.0 mmol) and N-methyl morpholine (440 μL, 1.73 mmol) in THF at 0° C. After two minutes, 3-methoxypropylamine (410 μL, 4.0 mmol) was added and the mixture was allowed to warm to rt. After thirty minutes, the reaction mixture was filtered through a bed of celite and all volatiles were removed under reduced pressure to yield N-Boc-L-leucine-3-methoxypropyl amide (1.10 g, 92%) as a white solid. $^1$H NMR: (CDCl$_3$) δ 0.93, 6H, d; 1.42, 9H, s; 3.35, 3H, s; 3.38, 2H, d; 3.43 m 2H, t; 4.03m 1H, m; 4.39, s, 1H; 4.91, 1H, m; 6.60, 1H, m,

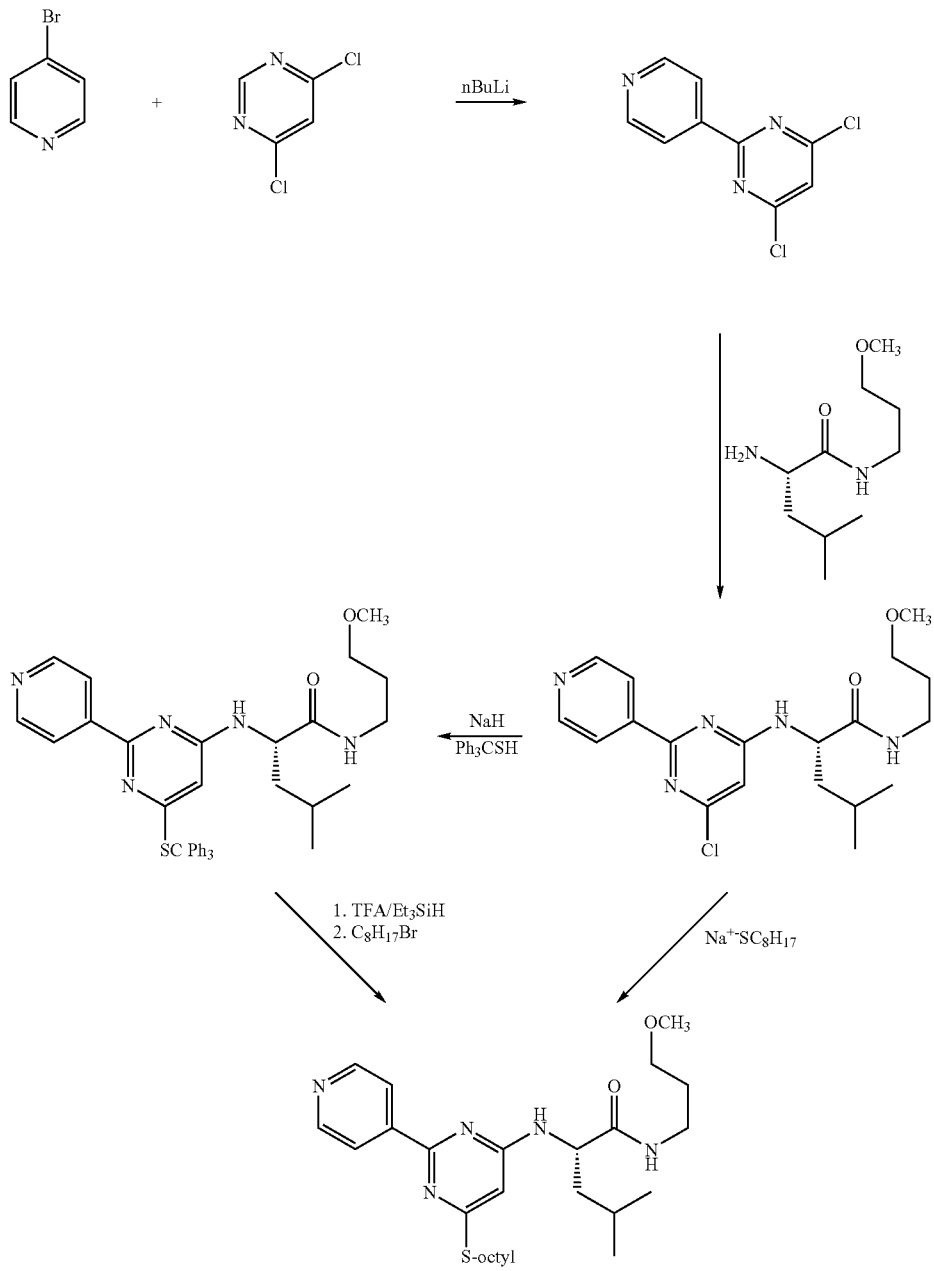

N-Boc-L-leucine 3-methoxypropyl amide (463 mg, 1.54 mmol) was in CH$_3$OH (10 mL) was treated with acetyl chloride (1 mL). After 45 minutes, all volatiles were removed under reduced pressure to yield L-leucine 3-methoxypropyl amide hydrochloride (310 mg, quant.) as a sticky solid.

nButyllithium (1.5 M in hexanes/1.53 mL, 2.3 mmol) was added dropwise to a solution of 4-bromopyridine (200 μL, 2.08 mmol) and in diethyl ether (20 mL)–78° C. After 30 minutes, the reaction mixture was warmed to –30° C. and 4,6-dichloropyrimidine (283 mg, 1.9 mmol) was added. The reaction mixture was allowed to warm to 0° C. over 60 min after which water (2 mmol) and acetic acid (4 mmol) were added followed by DDQ (431 mg, 1.9 mmol). After 30 minutes, the reaction mixture was diluted with diethyl ether (30 mL) and washed three times with aqueous 3M NaOH. the organic layer was dried over MgSO$_4$. Filtration and removal of volatiles under reduced pressure yielded a brown gummy solid which was purified by flash chromatography to afford 2-pyridyl-4,6-dichloropyrimidine as a white solid (0.261 mg, 61%). $^1$H NMR: (CDCl$_3$) δ 7.40, 1H, s; 8.23, 2H, d; 8.80, 2H, d.

A solution of L-leucine-3-methoxypropyl amide hydrochloride (220 mg, 1.1 mmol), 2-(4-pyridyl)-4,6-dichloropyrimidine (200 mg, 0.88 mmol) and Et$_3$N (692 μL, 5 mmol) in THF (5 mL) was heated to reflux. After 3 hours, the reaction mixture was cooled and filtered through a pad of celite. All volatiles were removed in vacuo to yield the disubstituted chloropyrimidine as a waxy solid.

Sodium hydride (80 mg, 2 mmol) was added to a solution of octanethiol (346 μL, 2 mmol in DMF (5 mL) at 0° C. After stirring for 30 min, the 2-(4-pyridyl)-4-(3-methoxypropylamido L-leucine)-6-chloropyrimidine was added in 500 μL of DMF and the reaction mixture was heated to 80° C. for 2 h. The mixture was cooled to rt and poured into satd aqueous NH$_4$Cl. The aqueous phase was extracted three times with ethyl acetate, the organic layers were washed twice with water and once with brine. The combined organic layers were dried over MgSO$_4$. Filtration followed by removal of volatiles in vacuo gave the crude product as a waxy solid. Purification by flash chromatography afforded the oxy (ether) analog of compound 68 as waxy solid (355 mg, 81%) $^1$H NMR: (CDCl$_3$) δ 0.88, 3H, t; 0.92, 3H, d; 1.00, 3H, d; 1.2–1.4, xH, m; 1.47, 3H, m; 1.80, 3H, m; 3.35, 2H, m; 3.38, 3H, s; 3.48, 2H, m; 4.05, 1H, m; 4.90, 1H, m; 6.22, 1H, s; 6.6; 1H, m; 8.20m 2H, d; 8.75, 2H, d.

An alternative to the displacement by alkylmercaptan is sulfur alkylation. Sodium hydride (80 mg, 2 mmol) was added to a solution of trityl mercaptan (346 μL, 2 mmol) in THF (5 mL) at –40° C. After stirring for 30 min, the 6-chloro-4-(3-methoxypropylamido-L-leucine)-2-(4-pyridyl)pyrimidine was added in 500 μL of THF and the reaction mixture was stirred for 1 h. The mixture was warmed to rt and poured into satd aqueous NH$_4$Cl. The aqueous phase was extracted three times with ethyl acetate, the organic layers were washed twice with water and once with brine. The combined organic layers were dried over MgSO$_4$. Filtration and removal of volatiles in vacuo followed by flash chromatography gave the 6-tritylthio compound as a waxy solid (355 mg, 81%)

The 6-tritylthiopyrimidine in CH$_2$Cl$_2$ was added dropwise to a solution of trifluoroacetic acid (500 μL) and triethylsilane (500 μL) in CH$_2$Cl$_2$ (10 mL). After 30 min all volatiles were removed in vacuo. The residue was dissolved in 5% Et$_3$N in DMF (5 mL) and bromooctane (163 μL, 1 mmol) was added to the solution. After 30 minutes, the reaction mixture was poured into satd aqueous NH$_4$Cl. The aqueous phase was extracted three timers with ethyl acetate, the organic layers were washed twice with water and once with brine. The combined organic layers were dried over MgSO$_4$. Filtration followed by removal of volatiles in vacuo gave the same crude product as a waxy solid. Purification by flash chromatography afforded the same oxy (ether) analog of compound 68 as a waxy solid (355 mg, 81%) $^1$HNMR: (CDCl$_3$) δ 0.88, 3H, t; 0.92, 3H, d; 1.00, 3H, d; 1.2–1.4 m xH, m; 1.47, 3H, m; 1.80, 3H, m; 3.35, 2H, m; 3.38, 3H, s; 3.48, 2H, m; 4.05, 1H, m; 4.90m 1H, m, 6.22, 1H, s; 6.6; 1H, m; 8.20m H, d; 8.75, 2H, d.

The synthesis of compounds in which Q is attached via carbon [e.g. Q=R$^{12}$OC(O)—(CH$_2$)$_p$—] is as follows:

Scheme 5

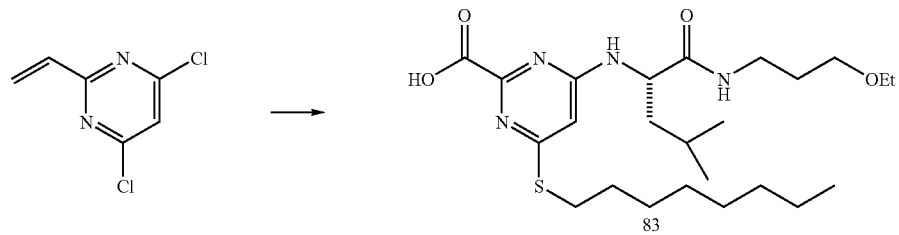

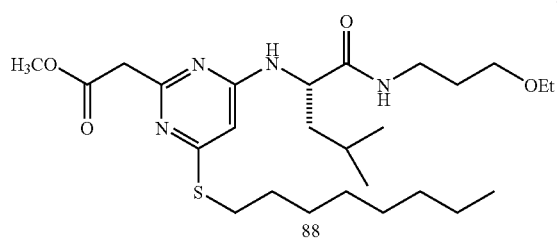
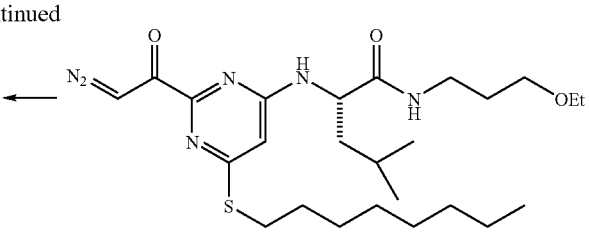

Vinyl lithium (10 mmol; generated from the reaction of nBuLi with tetravinyltin in diethyl ether) was added to a solution of 4,6-dichloropyrimidine (1.49 g, 10 mmol) in diethyl ether (70 mL) under an argon atmosphere at −30° C. The reaction mixture was quenched with acetic acid (600 mL) and water (200 mL) after stirring for 60 min. DDQ (2.27 g, 10 mmol) was added and the reaction mixture was warmed to 0° C. and stirred for 2 hr. The brownish slurry was then washed three times with 1M NaOH, once with brine and dried over MgSO$_4$. Filtration followed by removal of volatiles under reduced pressure afforded a dark brown tar from which 2-vinyl-4,6-dichloropyrimidine was isolated by flash chromatography (10% ethyl acetate in hexane).

Ozone gas generated by passing oxygen over an electrode was bubbled into a solution of 2-vinyl-4,6-dichloropyrimidine (1.40 g, 8 mmol) in methanol (100 mL) at −78° C. After a persistent blue color was observed dimethyl sulfide was added dropwise until the blue color disappeared. All volatiles were removed under reduced pressure and the product 2-formyl-4,6-dichloropyrimidine was purified by flash chromatography (30% ethyl acetate in hexane). $^1$H NMR: (CDCl$_3$) δ 9.97, 1H, s; 7.60, 1H, s.

Potassium permanganate (50 mg, 0.32 mmol) was added to a solution of 2-formyl-4,6-dichloropyrimidine (65 mg., 0.37 mmol) in acetone/water (4:1; 5 mL). After refluxing for 45 minutes the reaction mixture was poured into 0.5M KHSO$_4$ and extracted three times with ethyl acetate. The combined organic layers were washed three times with water, once with brine and dried over MgSO$_4$. Filtration followed by removal of volatiles under reduced pressure afforded the crude carboxylic acid as a white solid. $^1$H NMR: (CDCl$_3$) δ 8.02, 1H, s. The carboxylic acid proton is not observed.

4-6-Dichloropyrimidine-2-carboxylic acid can be functionalized in the same manner as other 2-substituted dichloro- or difluoropyrimidines. For example, 4-6-dichloropyrimidine-2-carboxylic acid was reacted first with N-(3-ethoxy)propyl-L-leucinamide in DMF in the presence of excess potassium carbonate and then with sodium octanethiolate to form the pyrimidine 83.

Isobutyl chloroformate (2.85 µL, 0.022 mmol) was added to a solution of pyrimidine-2-carboxylic acid 83 (9 mg, 0.019 mmol) and N-methyl morpholine (2.5 µL, 0.022 mmol) in THF (1 mL) at 0° C. After 10 min, freshly prepared diazomethane in ether was added. After stirring for 3 hr at rt, excess diazomethane was destroyed by the addition of acetic acid (5 mL). The reaction mixture was then poured into saturated NH$_4$Cl and extracted three times with diethyl ether. The combined organic layers were washed with brine and dried over MgSO$_4$. Filtration and removal of volatiles under reduced pressure gave the diazoketone as a pale yellow solid.

A solution of silver benzoate (20 mg, 0.087 mmol) in triethylamine (200 µL) was added dropwise to a solution of the diazoketone in THF/CH$_3$OH (3:1; 2 mL). The mixture was heated to reflux in the absence of light for 2 hours. After cooling to room temperature, the reaction mixture was poured into saturated NaHCO$_3$ and extracted three times with ethyl acetate. The combined organic layers were washed with brine and dried over MgSO$_4$. Filtration and removal of volatiles under reduced pressure gave the acetic acid 88, which was purified by flash chromatography (1:1 hexane:ethyl acetate). M/Z=511; $^1$H NMR: (CDCl$_3$) δ 0.8–1.0, 9H, m; 1.20, 3H, t; 1.2–1.5, 12H, m; 1.6–1.9, 8H, m; 3.05, 2H, t; 3.3–3.55, 6H, m; 3.77, 3H, s; 5.03, 2H, d; 6.02, 1H, s; 6.80, 1H, dd.

Scheme 6 shows a general method for the preparation of several compounds of the invention. Step 1 shows that various 2,4-dichloropyrimidines substituted at the 6-position were coupled with various imidazoles (DIEA, DMF, room temperature, 16 h) to give the corresponding 2-imidazolyl-4-chloropyrimidines. Step 2 shows that these compounds were then reacted with various amino amides (DIEA, DMSO, 80° C., 24 h) to give the final products. Details of the synthesis of these compounds are described below.

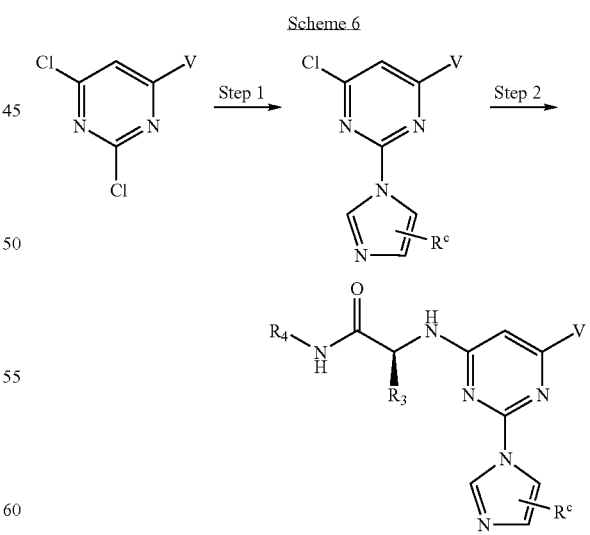

Several 2,4-dichloropyrimidines used in Scheme 6 were synthesized by methods analogous to the one shown in Scheme 7. Scheme 7 and the experimentals below show a specific example in which V=C$_6$H$_5$CH$_2$CH$_2$.

Scheme 7

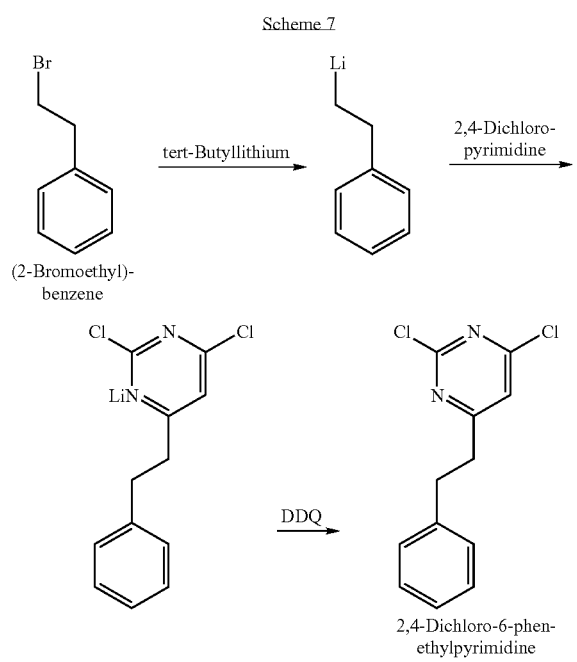

To a solution of 4.6 mL of (2-bromoethyl)benzene in 70 mL ethyl ether at −70° C. was added 41.5 mL of tert-butyllithium. The mixture was slowly allowed to warm to −30° C. over 2 h, then cooled to −60° C. and treated with 5.0 g of 2,4-dichloropyrimidine The reaction was again slowly allowed to warm to −30° C. over 2 h, then quenched by the addition of 1.94 mL of acetic acid and 0.30 mL of water in 5 mL tetrahydrofuran. The mixture was treated with 7.6 g of 2,3-dichloro-5,6-dicyano-1,4-benzoquinone (DDQ) in 25 mL THF and warmed to room temperature. The reaction was cooled to 0° C. and 13.4 mL of ice-cold 3 M NaOH was added to the mixture. After 5 minutes, the organic layer was separated and dried over sodium sulfate. The solvent was evaporated and the crude residue was chromatographed (2% to 10% EtOAc in hexanes) to give 4.0 g of 2,4-dichloro-6-phenethylpyrimidine.

The method shown in Scheme 7 was used in the synthesis of compounds 308, 309, 310, 312–319, 321, 323–330, 336–343, 346, 348, 350 and 351.

Several 2,4-dichloropyrimidines used in Scheme 6 were synthesized by methods analogous to the one shown in Scheme 8. Scheme 8 and the experimental descriptions below show a specific example where $R^1$=(4-Cl)$C_6H_4CH_2CH_2$.

Scheme 8

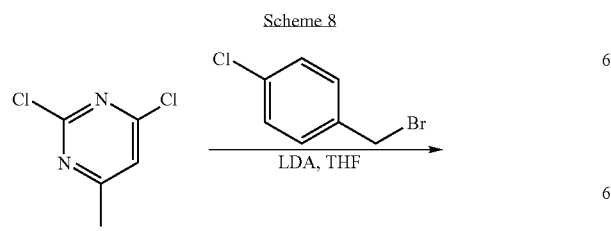

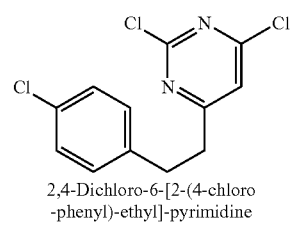

2,4-Dichloro-6-[2-(4-chloro-phenyl)-ethyl]-pyrimidine

Lithium diisopropylamide (11 mL, 2 M solution in heptane/tetrahydrofuran/ethylbenzene) was added dropwise over 5 min to a solution of 2,4-dichloro-6-methylpyrimidine (3.0 g) in tetrahydrofuran (20 mL) at −78° C. under nitrogen. The reaction was stirred at −78° C. for 30 minutes. 4-Chlorobenzylbromide (4.4 g) was dissolved in tetrahydrofuran (5 mL) and added dropwise over 5 minutes. The reaction was stirred at −78° C. for 30 min, allowed to warm to rt and stirred at rt for 16 h. Solvent was removed under vacuum. The residue was purified by column chromatography (5% ethyl acetate in hexanes) to afford 2,4-dichloro-6-[2-(4-chlorophenyl)ethyl]pyrimidine, (2.8 g).

The method shown in Scheme 8 was used in the synthesis of compounds 311, 322 and 331–335.

In some cases, the 2-imidazole-4-chloropyrimidines of Scheme 6 were replaced by 4-chloropyrimidines with other aryl substituents at the 2-position. These 4-chloropyrimidines were synthesized by methods analogous to the one shown in Scheme 9.

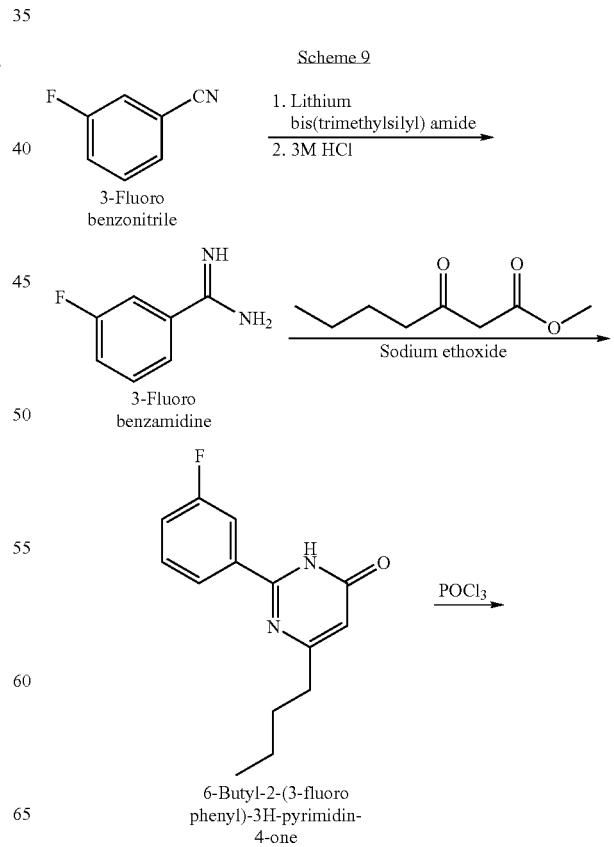

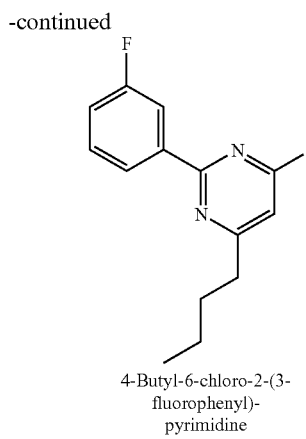

4-Butyl-6-chloro-2-(3-
fluorophenyl)-
pyrimidine

To a solution of lithium bis(trimethylsilyl)amide (1.0 M in tetrahydrofuran) was added a solution of 3-fluorobenzonitrile (2.5 g, Aldrich, USA) in 10 mL of anhydrous ether. After standing at room temperature for 2 h, the solution was cooled to 0° C. in an ice bath, and 28 mL of 3 M hydrochloric acid was added slowly. After stirring for 30 min, 100 mL of water was added and the ether layer was discarded. The aqueous layer was made basic with 2 M sodium hydroxide and extracted three times with chloroform. The chloroform layers were combined, dried over magnesium sulfate and concentrated in vacuo to yield 3-fluorobenzamidine (1.27 g) as a clear oil.

To a solution of 3-fluorobenzamidine (1.14 g) and 3-oxo-heptanoic acid methyl ester (1.0 g, Fluka, USA) in 15 mL of ethanol was added 3.15 mL of a 3 M solution of sodium ethoxide in ethanol. The mixture was heated to reflux for 48 h, allowed to cool to room temperature, and the volatiles were removed in vacuo. The residue was dissolved in chloroform and washed with water three times. The aqueous extractions were combined, acidified to pH=6, and washed three times with ethyl acetate. All organic layers were combined, dried over magnesium sulfate, and concentrated in vacuo. The product was purified by column chromatography using 60% ethyl acetate in hexanes as the mobile phase to yield 6-butyl-2-(3-fluorophenyl)-3H-pyrimidin-4-one (0.9 g).

A solution of N, N-dimethylaniline (0.31 mL) and 6-butyl-2-(3-fluoro-phenyl)-3H-pyrimidin-4-one (0.3 g) in 6 mL phosphorus oxychloride was heated in a sealed tube for 2.5 h at 125° C. The solution was allowed to cool and the phosphorous oxychloride were removed in vacuo. The remaining residue was washed four times with diethyl ether and the combined ether portions were washed with 0.5 M hydrochloric acid, dried over magnesium sulfate, and concentrated in vacuo to yield 4-butyl-6-chloro-2-(3-fluorophenyl)-pyrimidine (0.20 g).

The method shown in Scheme 9 was used in the synthesis of compounds 334 and 336.

In some cases, the amino amide used in Scheme 6 (Step 2) was a derivative of cis-3-ethoxycyclopentylamine. The racemic synthesis of this amine is shown in Scheme 10.

Scheme 10

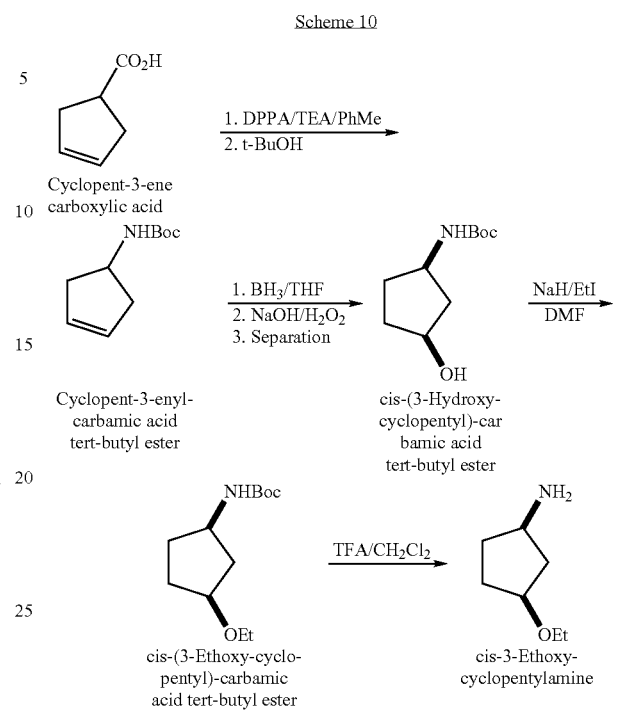

A solution of cyclopent-3-enecarboxylic acid (2.25 g), diphenylphosphoryl azide (4.7 mL), and triethylamine (2.8 mL) in 25 mL toluene was refluxed for 7 h. The mixture was cooled to rt and treated with 10 mL of tert-butanol. The resulting mixture was refluxed for an additional 16 h. The solvents were evaporated and the crude residue was chromatographed with silica gel (1:10 ethyl acetate:hexanes) to give Cyclopent-3-enylcarbamic acid tert-butyl ester (racemic): (2.37 g). Borane-tetrahydrofuran (1.5 M in THF, 20 mL) was added dropwise to a solution of cyclopent-3-enylcarbamic acid tert-butyl ester (1.83 g) in tetrahydrofuran (30 mL) at 0° C. The solution was gradually warmed to rt and stirred for 16 h. The reaction solution was cooled to 0° C. and sodium hydroxide (1 N, 33 mL) was slowly added followed by 30% hydrogen peroxide (33 mL). The resulting mixture was stirred at rt for an additional 5 h and diluted with ethyl acetate (70 mL). The aqueous layer was separated and extracted with ethyl acetate (30 mL×3). The combined organic layers were washed with water and brine, dried over Na$_2$SO$_4$, and concentrated via rotary evaporator. Silica gel chromatography (1:1 ethyl acetate:hexanes) provided 0.25 g of cis-(3-hydroxycyclopentyl)carbamic acid tert-butyl ester (racemic) followed by 1.07 g of the trans isomer. A solution of cis-(3-hydroxycyclopentyl)-carbamic acid tert-butyl ester (201 mg) in dimethylformamide (3 mL) was treated with sodium hydride (60% in mineral oil, 95 mg) at 0° C. After gas evolution had ceased, the mixture was stirred for 30 min at rt. Iodoethane (88 µL) was added to the mixture and the reaction was stirred at rt for 16 h. The excess sodium hydride was destroyed at 0° C. by the careful addition of aqueous ammonium chloride. The resulting mixture was partitioned between ethyl acetate and ammonium chloride and the organic layer was separated and washed with brine. The organic layer was dried over Na$_2$SO$_4$ and concentrated via rotary evaporator. Silica gel chromatography (1:4 ethyl acetate:hexanes) provided cis-(3-ethoxycyclopentyl)carbamic acid tert-butyl ester (racemic) (102 mg). Cis-(3-ethoxycyclopentyl)carbamic acid tert-butyl ester was stirred in 1:1 trifluoroacetic acid:dichloromethane for 0.5 h. The solvent was removed by evaporation to provide cis-3-ethoxycyclopentylamine (racemic).

The cis-3-ethoxycyclopentylamine obtained in Scheme 10 was coupled to Boc-protected leucine using a standard carbodiimide method [1-(3-dimethylaminopropyl)-3-ethyl-carbodiimide hydrochloride, 1-hydroxybenzotriazole, and triethylamine]. The resulting amide was deprotected using a standard protocol (trifluoroacetic acid and dichloromethane) to give one of the amino amides used in Scheme 6. This amino amide was used in the synthesis of compounds 308, 309 and 310 listed in Table 2A. Compounds 308, 309 and 310 were prepared from the racemic cis-3-ethoxycyclopentylamine and L-leucine to give a diastereomeric mixture. The diastereomers could be separated by a HPLC system equipped with a chiralcel AD column.

Compound 348 required the synthesis of 4-(trifluoromethyl)imidazole. The synthesis of this compound has been described previously: *J. Med. Chem.* 1975, 18, 895–900.

Reaction of imidazole with 1,4-dichloropyrimidine produced a mixture of 2-imidazolyl-, 4-imidazolyl- and 2,4-diimidazolyl-pyramidines which can then be separated by column chromatography:

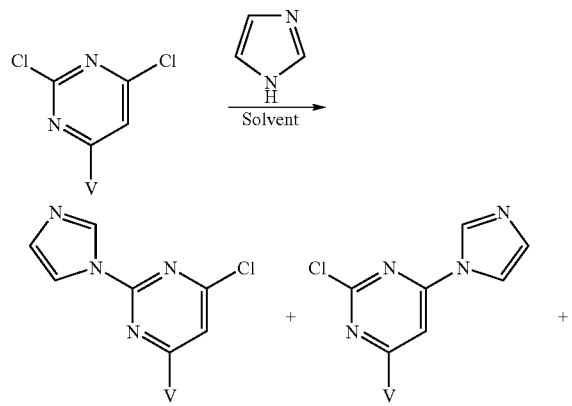

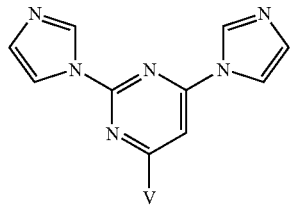

An alternative procedure was developed to circumvent the non-selective displacement of chlorides at the 2- and 4-positions of the pyrimidine ring. The method involves the incorporation of a methylthio-group into the chloro-pyrimidine. Since the chloride is a better leaving group than the methylthio-group, nucleophilic substitution occurs exclusively at the chloro-position. The resulting compound which contains a methylthio-group can then be oxidized to a methylsulfone and displaced by a second nucleophile. These procedures allow the preparation of regioselective product.

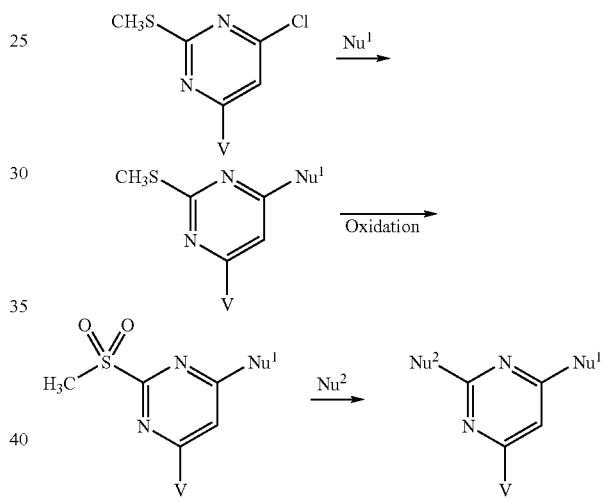

A specific example of this process is shown in Scheme 11 below.

Scheme 11

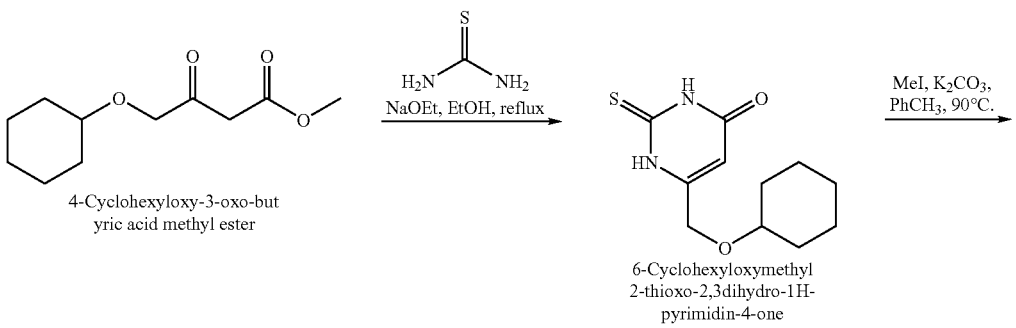

-continued
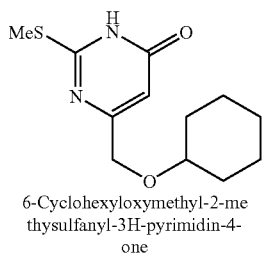 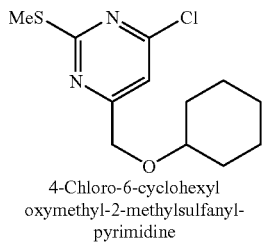
6-Cyclohexyloxymethyl-2-methylsulfanyl-3H-pyrimidin-4-one → SOCl₂, CH₂Cl₂, cat DMF, reflux → 4-Chloro-6-cyclohexyloxymethyl-2-methylsulfanyl-pyrimidine → 2-Amino-4-methylpentanoic acid(3-ethoxypropyl)amide, DMSO, DIEA, 90 C
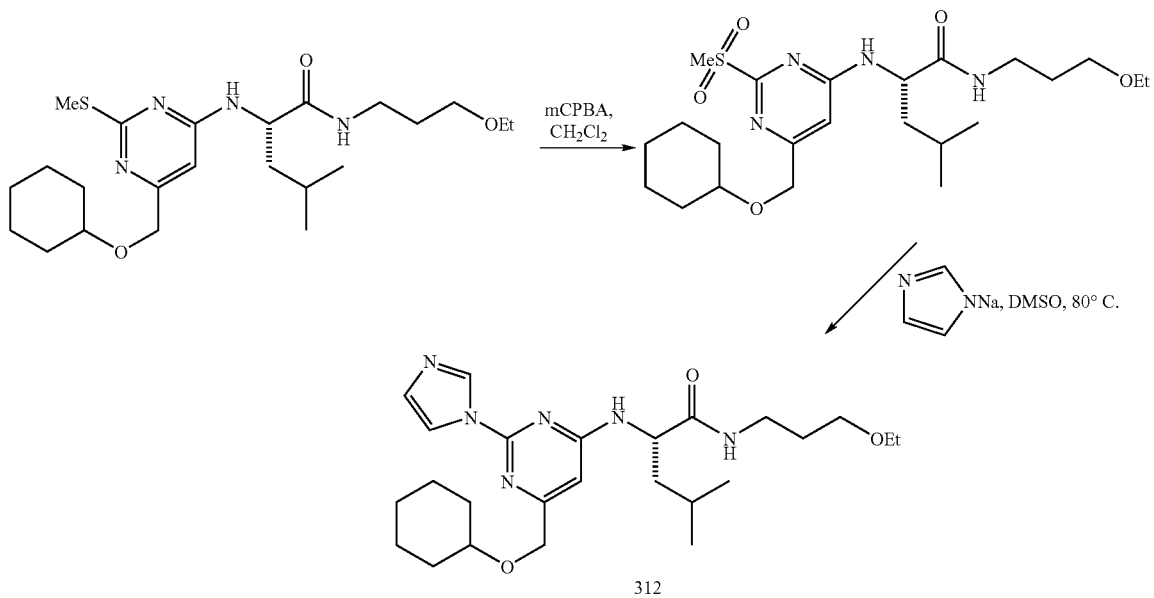
312
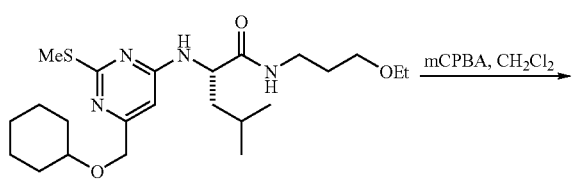
mCPBA, CH₂Cl₂
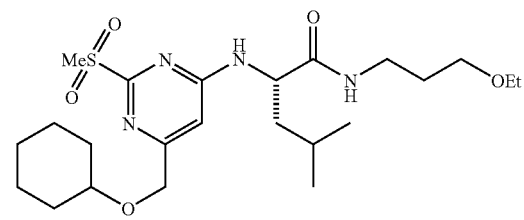
NNa, DMSO, 80° C.
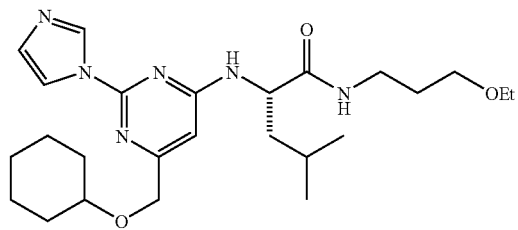
312

4-Cyclohexyloxy-3-oxo-butyric acid methyl ester (8.0 g) was added to a mixture of thiourea (34.7 g), sodium ethoxide (180 mL of 3 M ethanol solution) and ethanol (70 mL). The reaction was heated at reflux under nitrogen for 16 h. The ethanol was removed under vacuum. Residue was dissolved in water (400 mL) and the solution was cooled in an ice-bath. The solution was acidified with conc. hydrochloric acid to pH~1 and stood at rt for 16 h. The solid that formed was collected by filtration to afford 6-cyclohexyloxymethyl-2-thioxo-2,3-dihydro-1H-pyrimidin-4-one (7.6 g).

A mixture of 6-cyclohexyloxymethyl-2-thioxo-2,3-dihydro-1H-pyrimidin-4-one (0.2 g), toluene (5.5 mL), iodomethane (0.48 g) and potassium carbonate (0.57 g) was heated at 90° C. in a sealed tube for 16 h. The mixture was partitioned in water and ethyl acetate. The ethyl acetate layer was dried over magnesium sulfate, filtered, and evaporated. The residue was purified by column chromatography (40% ethyl acetate in hexanes) to afford 6-cyclohexyloxymethyl-2-methylsulfanyl-3H-pyrimidin-4-one (90 mg).

To a mixture of 6-cyclohexyloxymethyl-2-methylsulfanyl-3H-pyrimidin-4-one (20 mg) in dichloromethane (2 mL) and dimethylformamide (catalytic amount) was added thionyl chloride (47 mg). The mixture was heated at reflux for 1.5 h. The solvent was removed under vacuum to give 4-chloro-6-cyclohexyloxymethyl-2-methylsulfanylpyrimidine, which was used in the next reaction without further purification.

A mixture of 4-chloro-6-cyclohexyloxymethyl-2-methylsulfanyl-pyrimidine, the hydrochloride salt of 2-amino-4-methylpentanoic acid (3-ethoxypropyl)amide (60 mg), and diisopropylethylamine (61 mg) in dimethylsulfoxide (0.5 mL) was heated at 95° C. for 16 h. The mixture was partitioned in water and ethyl acetate. The ethyl acetate layer was dried over sodium sulfate, filtered and evaporated. The residue was purified by column chromatography (30% ethyl acetate in hexanes) to give 2-(6-cyclohexyloxymethyl-2-methylsulfanyl-pyrimidin-4-ylamino)-4-methyl-pentanoic acid (3-ethoxy-propyl)-amide (12 mg).

To a mixture of the previously described thiopyrimidine (12 mg) in dichloromethane (1 mL) was added 3-chloroperoxybenzoic acid (14 mg). After the mixture was stirred at rt for 2.5 h, it was diluted with dichloromethane. The mixture was washed with saturated sodium bicarbonate, dried over magnesium sulfate, filtered and evaporated to give 2-(6-cyclohexyloxymethyl-2-methanesulfonyl-pyrimidin-4-ylamino)-4-methyl-pentanoic acid (3-ethoxy-propyl)-amide, which was used without further purification.

A mixture of the previously described sulfonopyrimidine, imidazole (sodium salt, 7.3 mg) and dimethylsulfoxide (0.5 mL) was heated at 80° C. for 16 h. The mixture was partitioned in water and ethyl acetate. The ethyl acetate was dried over sodium sulfate, filtered and evaporated. The crude product was purified by semi-preparative HPLC to afford 2-(6-Cyclohexyloxymethyl-2-imidazol-1-yl-pyrimidin-4-ylamino)-4-methyl-pentanoic acid (3-ethoxy-propyl)-amide (312) (2 mg): MS m/z 473.3 (M+H).

The synthesis of analogs with the Q group (e.g. arylimidazolyl, benzimidazolyl and furanylimidazolyl) linked to the pyrimidine ring via a N—C bond, can be performed using the method outlined in Scheme 12. For example, an arylimidazole was reacted with 2,4-dichloropyrimidine and the resulting regioisomers were separated. Subsequence reaction of the 4-chloropyrimidine isomer with an amine affords the final product. Other nitrogen containing nucleophiles such as benzimidazoles can be used to replace the arylimidazole in these procedures to obtain the corresponding analogs.

Scheme 12

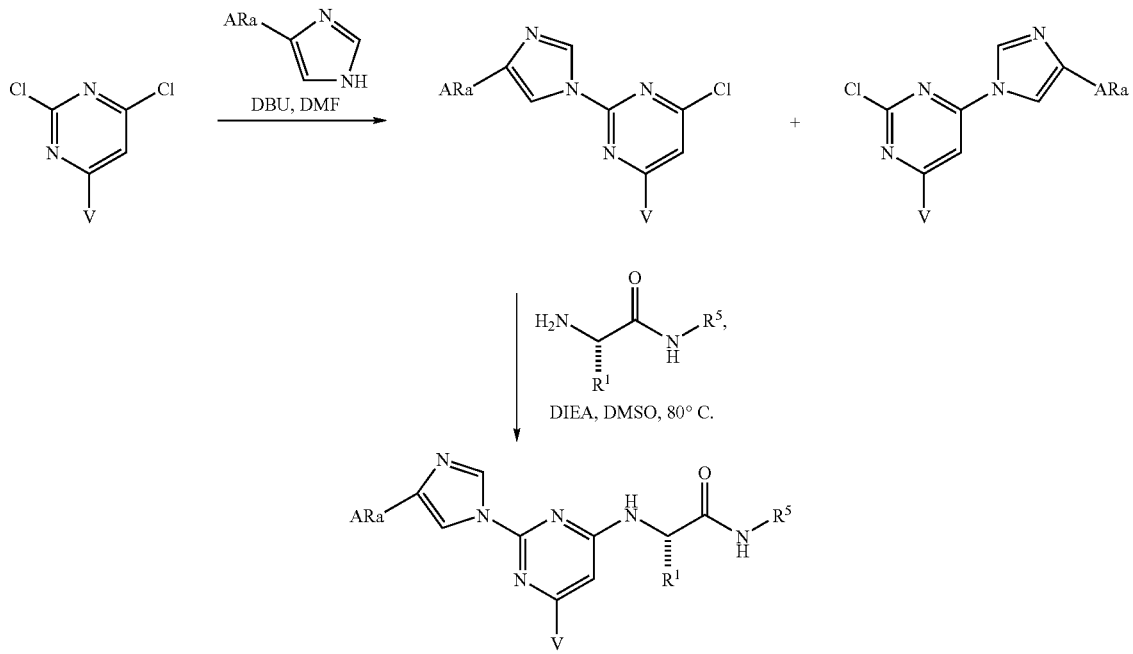

The synthetic methods for some reagents incorporated as the Q groups (Formula I) are outlined in Schemes 13 to 17.

Several arylimidazoles used in the invention were synthesized from the reaction of aryl aldehydes (Scheme 13) with p-tolylsulfonyl isocyanide (TosMIC) followed by heating in methanolic ammonia (*Heterocycles*, 1994, 39, 139).

Scheme 13

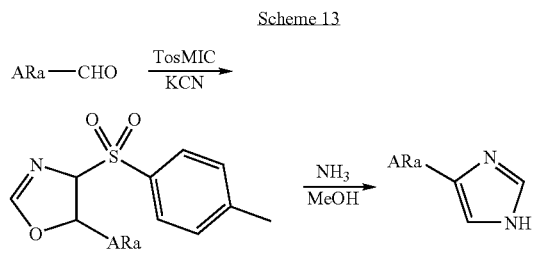

Alternatively, several imidazoles were synthesized from the reaction of 2-bromomethylketones with formamide (Scheme 14). This synthetic procedure is known from the literature (*J. Am. Chem. Soc.*, 1994, 116, 11030). In some cases, the bromomethylketones used in Scheme 14 were obtained from the corresponding ketones via a known bromination procedure (*Aust. J. Chem.*, 1989, 42, 1735).

Scheme 14

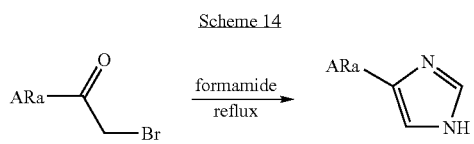

Several benzimidazoles used in the invention were obtained by the reaction of 2-aminoanilines with formic acid and aqueous HCl (Scheme 15) using a literature procedure (*Org. Syn.*, 1943, Coll Vol 2, 65). Alternatively, these compounds were obtained from refluxing 2-aminoanilines with ethoxymethylenemalononitrile in isopropyl alcohol (Scheme 16) following literature precedent (*Tetrahedron Lett.*, 1993, 34, 1897).

Scheme 15

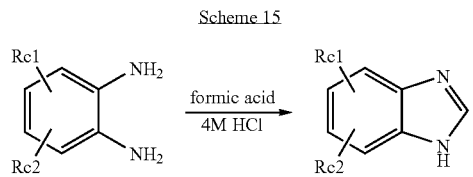

Scheme 16

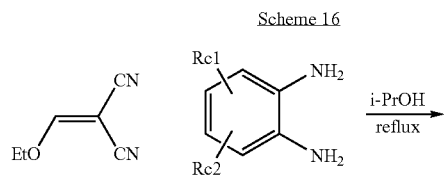

-continued

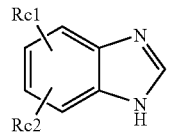

Furanyl-imidazoles were prepared by the TosMIC reaction from aldehydes, which can be obtained either by reduction of acids, esters or amides; or by oxidation of primary alcohols. These procedures are well known in the literature. For example, ethyl 2-trifluoromethyl-furan-3-carboxylate (Scheme 17) prepared from literature procedures (U.S. Pat. No. 5,405,865, Apr. 11, 1995) was converted to an aldehyde by reduction of a Weinreb amide. The aldehyde was then reacted with the TosMIC and methanolic ammonia to yield 4-(2-trifluoromethyl-furan-3-yl)-imidazole.

Scheme 17

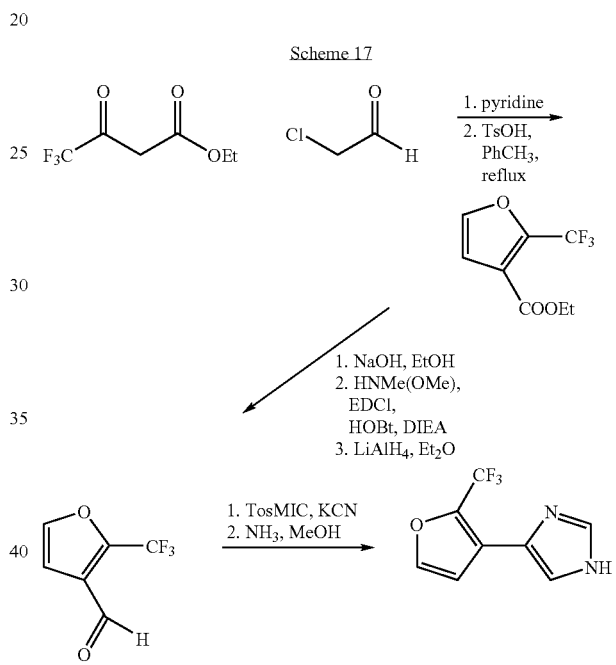

Representative procedures for reactions shown in Schemes 12 to 17 are as follows:

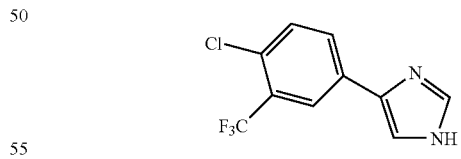

To a round-bottom flask containing 4-chloro-3-(trifluoromethyl)benzaldehyde (1.83 g, 8.8 mmol, 1.1 eq) and tosylmethyl isocyanide (1.56 g, 8.0 mmol, 1.0 eq) was added EtOH (15 mL, absolute) and cat. KCN (48 mg, 0.80 mmol, 10 mol %). The mixture was stirred at room temperature (rt) for 3 h and the resulting suspension was filtered. The solid residue was washed with cold EtOH and dried in vacuo. The tosyloxazoline intermediate was added to a glass pressure vessel containing $NH_3$ in methanol (50 ml of a 7.0 N solution). The vessel was capped and heated to 100° C. for 14 h. The contents were carefully cooled to 0° C. and the vessel was opened. Upon warming slowly to rt, most of the ammonia had dissipated. The mixture was transferred to a round-bottom flask and concentrated in vacuo. 2-(6-Cyclohexyloxymethyl-2-imidazol-1-yl-pyrimidin-4-ylamino)-4-methyl-pentanoic acid (3-ethoxy-propyl)-amide (312) (0.334 g, 17%) was isolated from the crude mixture by flash chromatography (dichloromethane/methanol 10/1). ESI-MS (m/z) 247 [M+H]⁺.

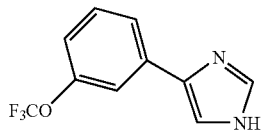

Bromine (0.76 mL) was added dropwise to a 0° C. solution of 3'-(trifluoromethoxy)acetophenone (3.0 g) and hydrobromic acid (48% aqueous, 1 mL) in acetic acid (15 mL). The solution was allowed to stir at rt for 45 minutes, then heated to 40° C. for 90 minutes. The volatiles were removed in vacuo to give a mixture of 2-bromo-1-[3-(trifluoromethoxy)phenyl]-ethan-1-one and 2,2-dibromo-1-[3-(trifluoromethoxy)phenyl]-ethan-1-one.

The above mixture (2.6 g) and formamide (35 mL) were heated to reflux for 2.5 hours. The resulting solution was allowed to cool to rt, basified to pH=10 with 10% potassium carbonate, and extracted three times with chloroform. The chloroform extracts were combined, washed with brine, dried over sodium sulfate, filtered, and the volatiles were removed in vacuo. The resulting residue was purified on silica gel using ethyl acetate as the mobile phase to yield 4-(3-trifluoromethoxyphenyl)imidazole (0.3 g). ESI-MS (m/z) 229 [M+H]⁺.

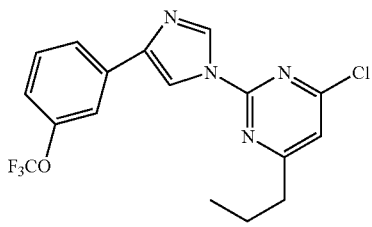

To a solution of 2,4-dichloro-6-propyl-pyrimidine (0.15 g) and 4-(3-trifluoromethoxy-phenyl)-1H-imidazole (0.2 g) in N,N-dimethylformamide (10 mL) was added 1,8-diazabicyclo[5.4.0]undec-7-ene (0.18 mL). After stirring at room temperature overnight, the solution was taken up in water and extracted three times with ethyl acetate. The ethyl acetate layers were combined washed twice with brine, dried over magnesium sulfate, and the volatiles were removed in vacuo. The resulting oil was purified on silica gel using 20% ethyl acetate/hexanes as the mobile phase to yield 4-chloro-6-propyl-2-[4-(3-trifluoromethoxyphenyl)-imidazol-1-yl]-pyrimidine (72.5 mg, first eluting regioisomer, ESI-MS (m/z) 383.3/385.2 [M+H]⁺, and 2-chloro-4-propyl-6-[4-(3-trifluoromethoxyphenyl)-imidazol-1-yl]-pyrimidine (88.4 mg, second eluting regioisomer).

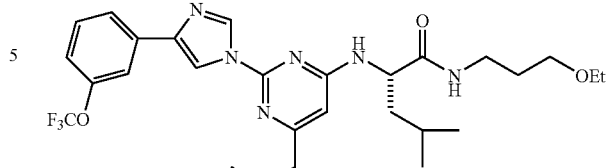

A solution of 4-chloro-6-propyl-2-[4-(3-trifluoromethoxyphenyl)-imidazol-1-yl] pyrimidine (25.8 mg), L-leucine-3-ethoxypropylamide (30 mg), N,N-diisopropylethylamine (23 µL) in dimethylsulfoxide (2.0 mL) was heated to 80° C. for 5 hours. The solution was cooled to room temperature, taken up in water, and extracted three times with ethyl acetate. The ethyl acetate layers were combined, washed twice with brine, dried over magnesium sulfate, filtered, and the solvents were removed in vacuo. After purification by semi-preparative HPLC, the trifluoroacetate salt of 4-methyl-2-{6-propyl-2-[4-(3-trifluoromethoxyphenyl) imidazol-1-yl]-pyrimidin-4-ylamino}-pentanoic acid (3-ethoxypropyl) amide (27.9 mg) was obtained. ESI-MS (m/z) 563 [M+H]⁺.

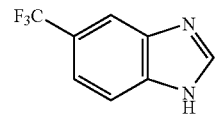

A mixture of 4-(trifluoromethyl)-1,2-phenylenediamine (3.0 g), formic acid (1.3 mL), and hydrochloric acid (4 M, 17 mL) was heated to reflux for 45 minutes. The mixture was allowed to cool to room temperature and neutralized with concentrated ammonium hydroxide. The aqueous layer was decanted off to give 5-trifluoromethyl-1H-benzimidazole (2.56 g) as a black solid. ESI-MS (m/z) 187 [M+H]⁺.

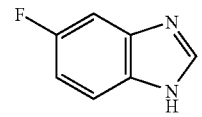

A solution of 4-fluoro-1,2-phenylenediamine (2.0 g) and ethoxymethylenemalononitrile (2.9 g) in isopropanol (80 mL) was heated to reflux overnight. The volatiles were removed in vacuo to yield 5-fluoro-1H-benzimidazole (1.8 g). ESI-MS (m/z) 137 [M+H]⁺.

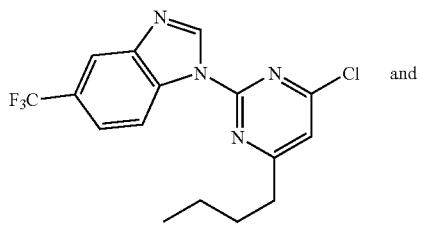

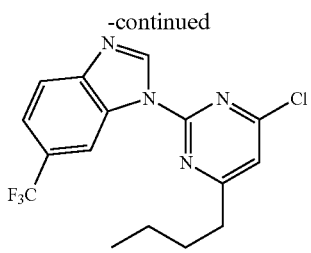

To a solution of 2,4-dichloro-6-butylpyrimidine (0.60 g) and 5-trifluoromethyl-1H-benzimidazole (0.71 g) in N,N-dimethylformamide (25 mL) was added 1,8-diazabicyclo[5.4.0]undec-7-ene (0.66 mL). After stirring at room temperature overnight, the solution was taken up in water and extracted three times with ethyl acetate. The ethyl acetate layers were combined, washed twice with brine, dried over magnesium sulfate, and the volatiles were removed in vacuo. The resulting oil was purified on silica gel using 30% ethyl acetate/hexanes as the mobile phase. The first two eluting regioisomers were 1-(6-butyl-4-chloropyrimidin-2-yl)-5-trifluoromethyl-1H-benzimidazole and 1-(6-butyl-4-chloropyrimidin-2-yl)-6-trifluoromethyl-1H-benzimidazole (80 mg of each). ESI-MS (m/z) 355 [M+H]$^+$.

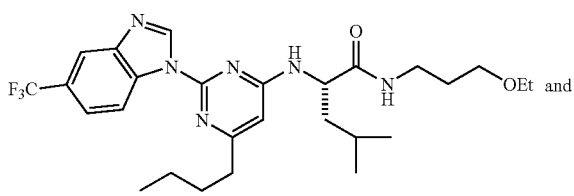

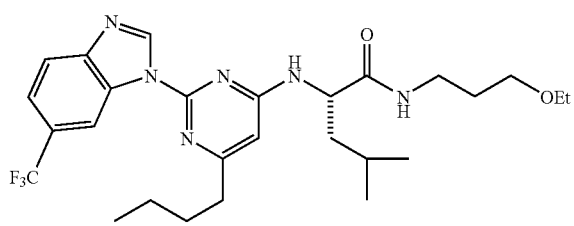

The first eluting isomer from above (16 mg) was reacted with L-leucine-3-ethoxypropylamide hydrochloride (35 mg), N,N-diisopropylethylamine (120 µL) in dimethylsulfoxide (1.5 mL) at 90° C. overnight. The solution was cooled to room temperature, taken up in water, and extracted three times with ethyl acetate. The ethyl acetate layers were combined, washed twice with brine, dried over magnesium sulfate, filtered, and the solvents were removed in vacuo. After purification by semi-preparative HPLC, 14.3 mg of 2-[6-Butyl-2-(5-trifluoromethylbenzoimidazol-1-yl)-pyrimidin-4-ylamino]-4-methylpentanoic acid (3-ethoxypropyl)amide and was obtained. ESI-MS (m/z) 535 [M+H]$^+$. The second eluting isomer was reacted in the same manner, using the same quantities to yield 14.2 mg. 2-[6-Butyl-2-(6-trifluoromethylbenzoimidazol-1-yl)-pyrimidin-4-ylamino]-4-methylpentanoic acid (3-ethoxypropyl)amide. ESI-MS (m/z) 535 [M+H]$^+$.

Numerous arylpiperazines used in the invention were synthesized via a palladium mediated coupling of an arylbromide with piperazine (*Tetrahedron Lett.*, 1998, 39, 617), shown in Scheme 18. The arylpiperazine was then reacted with a chloropyrimidine derivative to obtain the desire product. Similarly, arylpiperidines and substituted 1,2,3,4-tetrahydro-pyrazino[1,2-a]indoles can be used to replace the arylpiperazine in Scheme 18.

Scheme 18

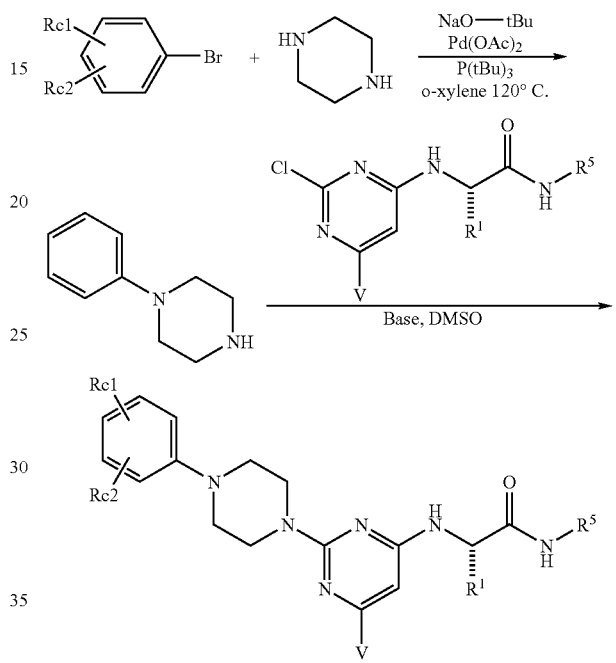

The synthesis shown in Scheme 18 can be carried out as follows:

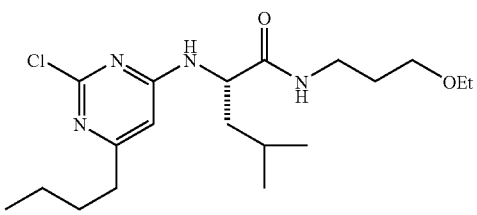

6-Butyl-2,4-dichloropyrimidine (1.0 g), L-leucine-3-ethoxypropylamide hydrochloride (17 mL of a 0.32 M solution in DMSO), and N,N-diisopropylethylamine (3.0 mL) were stirred for 24 h in 20 mL methyl sulfoxide at 60 C. The solution was cooled to room temperature and diluted with ethyl acetate (100 mL), then washed 4 times with 100 mL aliquots of a saturated aqueous solution of sodium chloride. Silica gel chromatography (gradient: 20–40–50–100% ethyl acetate in hexanes) followed by semi-preparative HPLC purification of mixed fractions provided 1.24 g of 2-(6-butyl-2-chloropyrimidin-4-ylamino)-4-methypentanoic acid (3-ethoxypropyl)amide as a colorless oil.

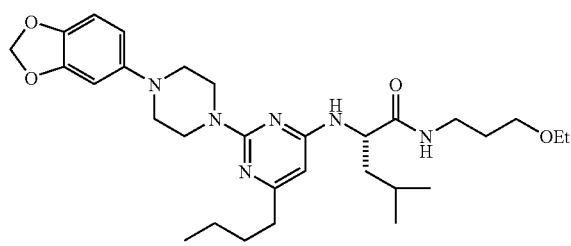

2-(6-Butyl-2-chloro-pyrimidin-4-ylamino)-4-methylpentanoic acid (3-ethoxypropyl)amide (10 mg), 1-benzo[1,3]dioxol-5-yl-piperazine dihydrochloride (25 mg), and N,N-diisopropylethylamine (50 μL) were stirred for 24 h in 1 mL methyl sulfoxide at 100° C. The solution was cooled to room temperature and diluted with ethyl acetate (30 mL), then washed 4 times with 30 mL aliquots of a saturated aqueous solution of sodium chloride. Semi-preparative HPLC followed by silica gel chromatography (gradient: 2–4% methyl alcohol in methylene chloride) provided 2.2 mg of 2-[2-(4-benzo[1,3]dioxol-5-yl-piperazin-1-yl)-6-butylpyrimidin-4-ylamino]-4-methylpentanoic acid (3-ethoxypropyl) amide. ESI-MS (m/z) 555 [M+H]$^+$.

The synthesis of analogs with the Q group linked to the pyrimidine ring via a C—C bond, can be performed using the method outlined in Scheme 19. For example, arylnitrile was converted to an amidine which was then condensed with a ketoester to form a pyrimidone. The pyrimidone was reacted with phosphorous oxychloride to give a chloropyrimidine, which was then reacted with an amine to yield the desired product.

Scheme 19

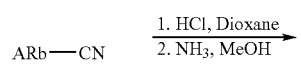

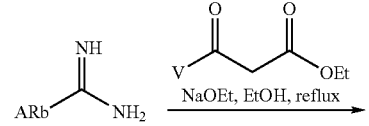

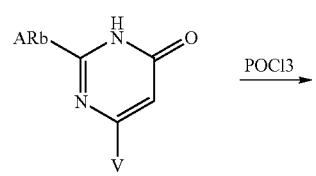

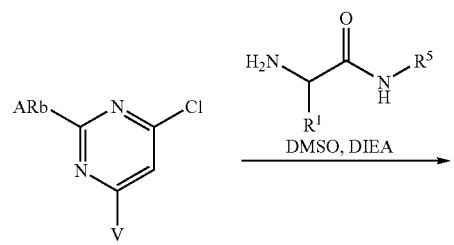

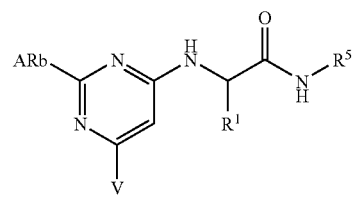

When chloro- or-bromo pyridylnitrile was used (Scheme 20), the analogs could be further derivatized by a Suzuki or Stille coupling reaction using aryl boronic acids or aryl trialkyltin reagents, respectively.

Scheme 20

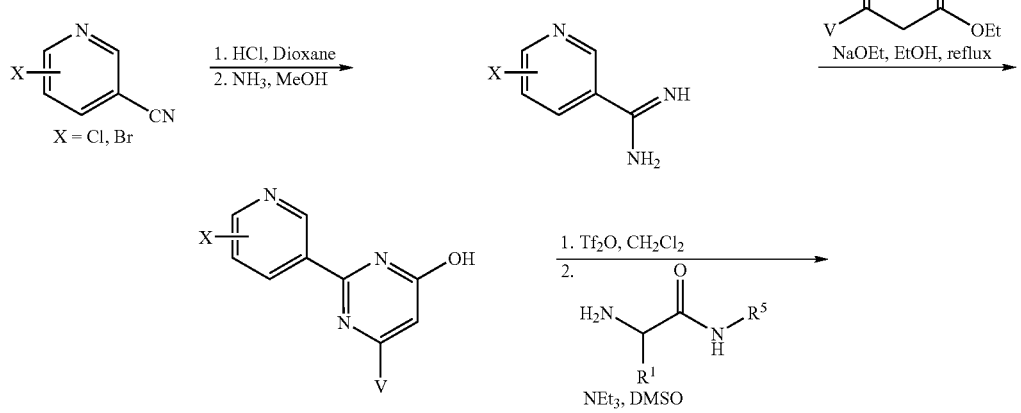

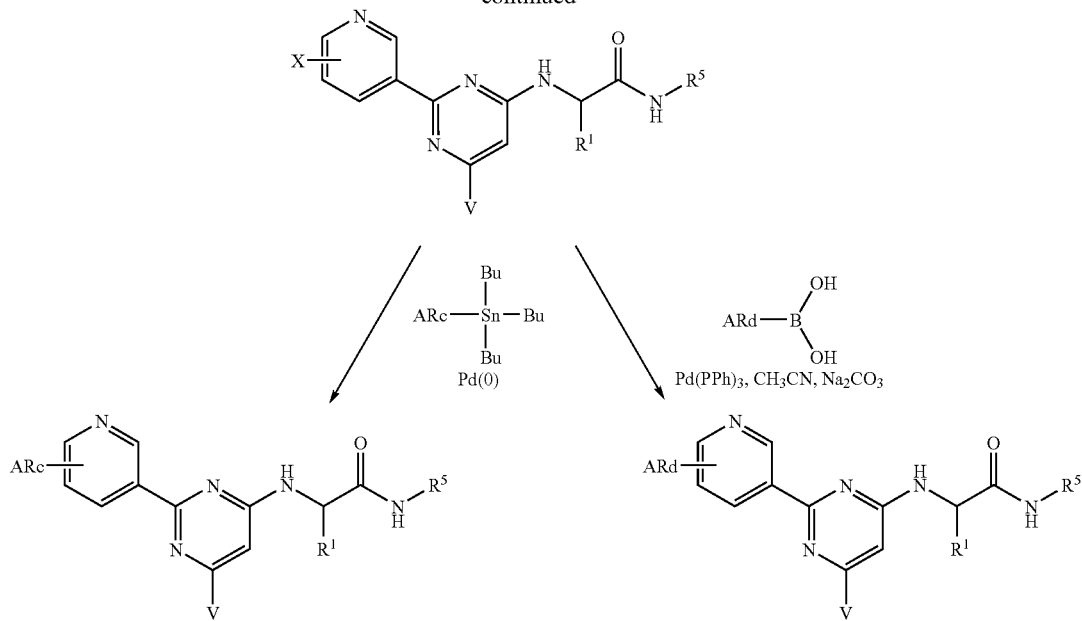
Furthermore, an aryl group can be introduced directly to the pyrimidine ring via a Suzuki or Stille coupling reaction (Scheme 21). For example, 4-trifluoromethoxyphenylboronic acid or tributyl-(5,6-dichloro-benzofuran-3-yl)-stannane was coupled with a 2-chloropyrimidine derivative to yield desired products.
Scheme 21
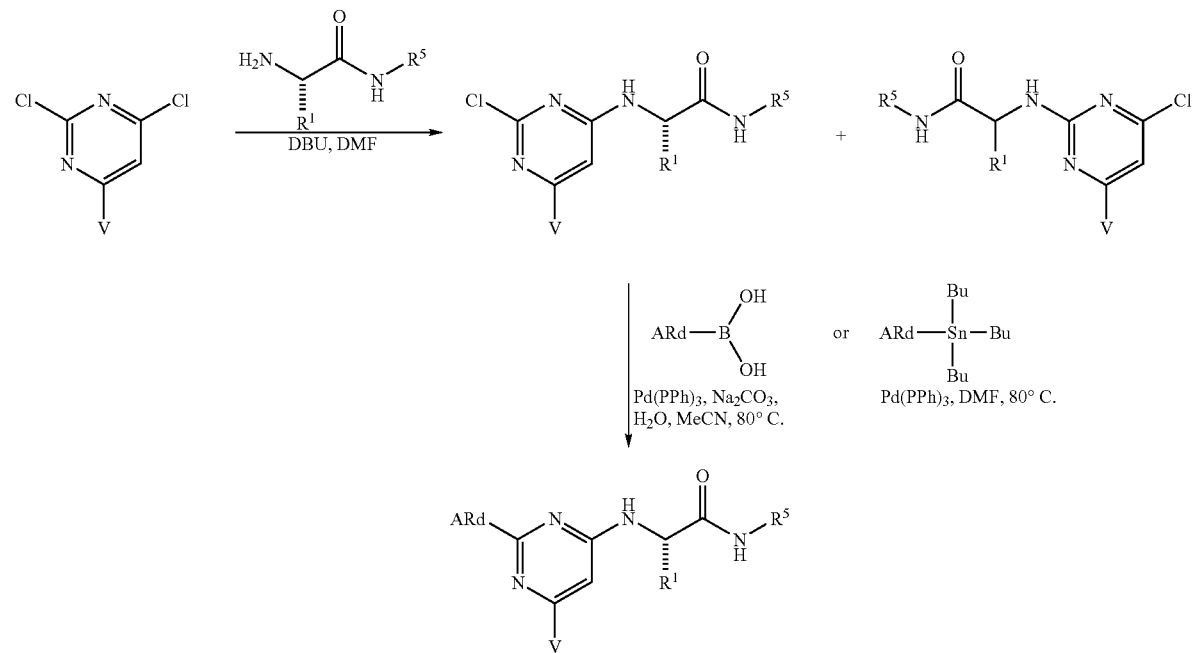

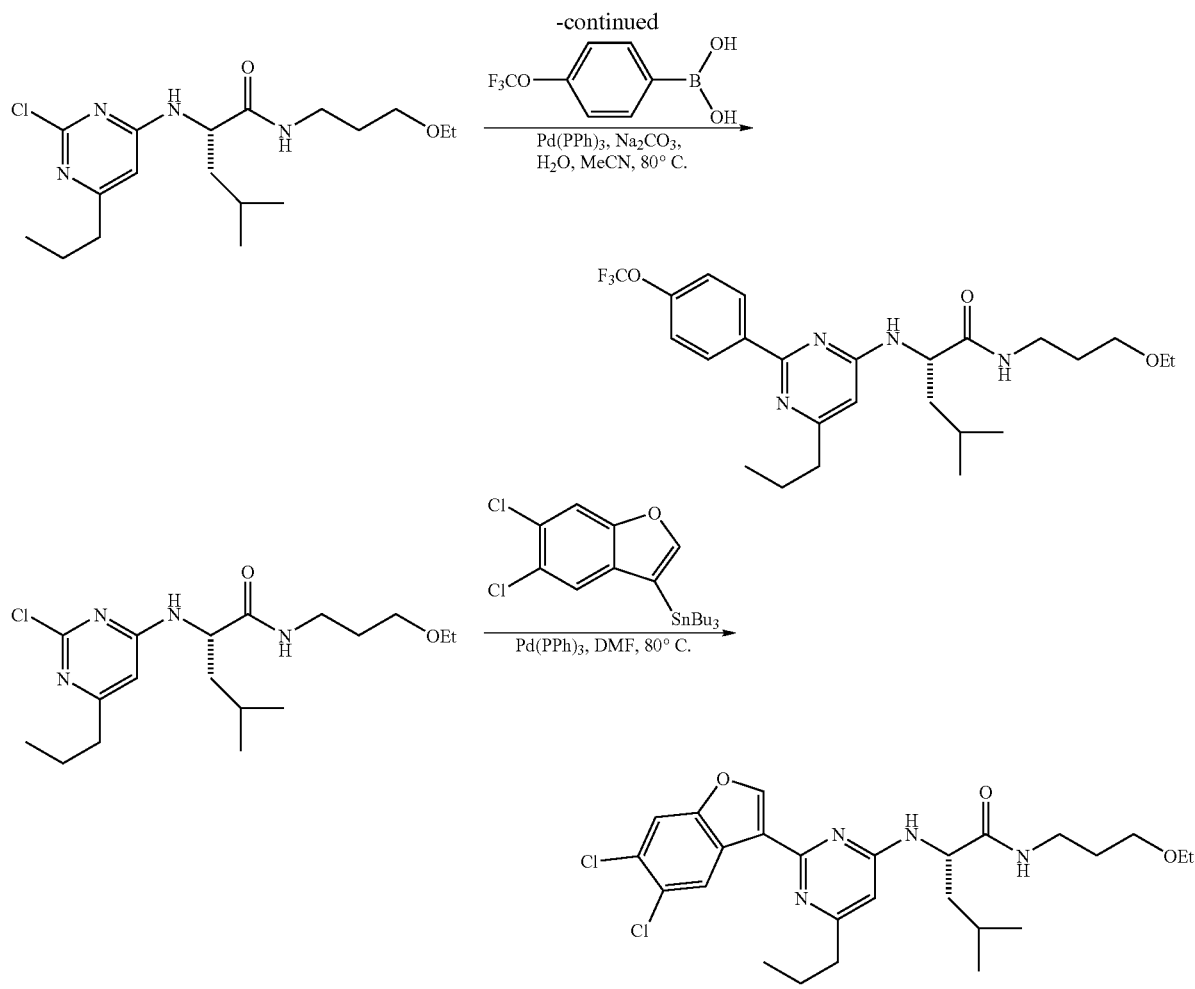

The aryl boronic acids and aryl tin reagents are either commercially available or prepared by methods known in the literature. In general, reaction of an aryl lithium with trialkylborate, followed by aqueous work up gave the aryl boronic acid for the Suzuki reaction. Reaction of an aryl lithium with trialkyltin chloride afforded the aryl tin reagents for the Stille coupling reaction. A specific example for the preparation of a trialkyltin reagent is shown in Scheme 22.

Scheme 22

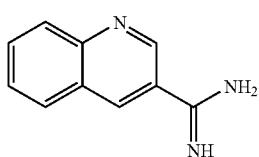

Representative procedures for carrying out syntheses shown in Schemes 19 to 22 are as follows:

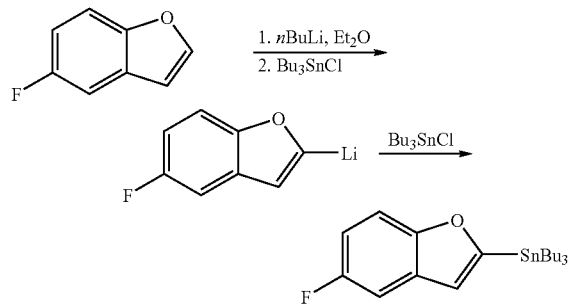

Quinoline-3-nitrile (1.0 g) was dissolved in diethyl ether (30 mL) and treated with lithium bis(trimethylsilyl)amide (1.0 M in THF, 13 mL). The reaction was stirred for 3 hours, then washed 3 times with 1 N HCl (50 mL). The combined aqueous washes were neutralized with 6 N NaOH and extracted 6 times with ethyl acetate (50 mL). The ethyl acetate extractions were dried over sodium sulfate and the solvent was evaporated to provide 0.63 g of quinoline-3-carboxamidine.

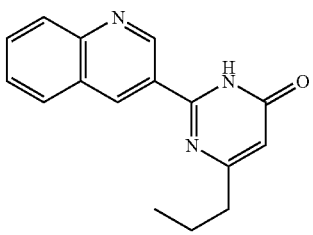

Quinoline-3-carboxamidine (314 mg), ethyl butyrylacetate (290 mg), and sodium ethoxide (21 wt % in ethanol, 1.1 mL) were refluxed for 48 h in 20 mL of ethanol. The solvent was evaporated and the residue was partitioned between ethyl acetate and brine. The ethyl acetate phase was dried with sodium sulfate and the solvent was evaporated. Silica gel chromatography (50:45:5 ethyl acetate/hexanes/methanol) provide 280 mg of 6-propyl-2-quinolin-3-yl-3H-pyrimidin-4-one.

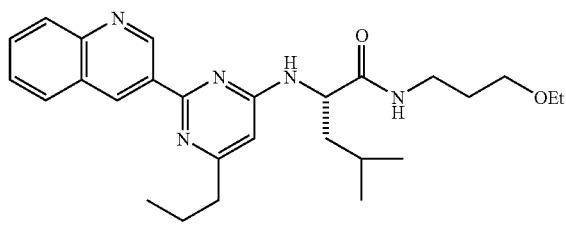

6-Propyl-2-quinolin-3-yl-3H-pyrimidin-4-one (66 mg) and triethylamine (126 mg) in methylene chloride were cooled to −78° C. and treated with trifluoromethanesulfonic anhydride. The reaction was stirred for 3.5 h at −78° C., then quenched by the addition of water. The organic layer was separated and dried with sodium sulfate. Evaporation of the solvent followed by silica gel chromatography (15% ethyl acetate in hexanes) provided 27 mg of trifluoromethanesulfonic acid 6-propyl-2-quinolin-3-yl-pyrimidin-4-yl ester. This intermediate was dissolved in methyl sulfoxide (6 mL) and treated with 2-amino-4-methylpentanoic acid (3-ethoxypropyl)amide hydrochloride (35 mg) and N,N-diisopropylethylamine (61 μL). The reaction was stirred overnight at room temperature, then diluted with ethyl acetate (50 mL) and washed twice with saturated aqueous sodium chloride (50 mL). The ethyl acetate solution was dried with sodium sulfate and the solvent was evaporated. 4-Methyl-2-(6-propyl-2-quinolin-3-yl-pyrimidin-4-ylamino)-pentanoic acid (3-ethoxypropyl) amide (20.3 mg) was isolated after column chromatography (40% ethyl acetate in hexanes). ESI-MS (m/z) 465 [M+H]$^+$.

2-[2-(5-bromopyridin-3-yl)-6-propylpyrimidin-4-ylamino]-4-methylpentanoic acid (3-ethoxypropyl)-amide (65 mg), 3-trifluoromethoxyphenylboronic acid (110 mg), and tetrakis(triphenylphosphine)palladium (0) (15 mg) were heated at 80° C. in 15 mL acetonitrile and 15 mL 0.4 M sodium carbonate for 16 h. The reaction was cooled to rt and extracted with ethyl acetate. Silica gel chromatography (70:25:5 hexanes/ethyl acetate/methanol as eluent) provided the title compound with slight impurities. These impurities were removed by forming the hydrochloride salt of the product and washing with ethyl ether. Final purification with semi-prep HPLC provided 57.8 mg of 4-Methyl-2-{6-propyl-2-[5-(3-trifluoromethoxyphenyl)pyridin-3-yl]pyrimidin-4-ylamino}pentanoic acid (3-ethoxypropyl) amide as the TFA salt.

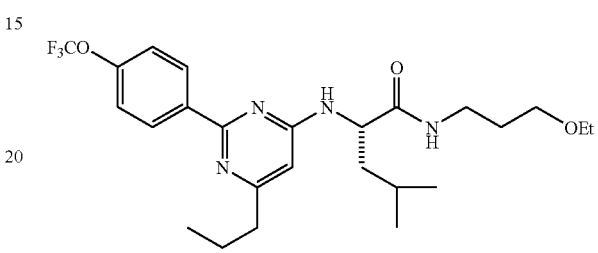

A mixture of 2-(2-chloro-6-propyl-pyrimidin-4-ylamino)-4-methyl-pentanoic acid (3-ethoxy-propyl)-amide (31.4 mg), 4-(trifluoromethoxy)phenylboronic acid (19 mg), sodium carbonate (0.4M aqueous solution, 0.5 mL), and acetonitrile (0.5 mL) was degassed with argon for five minutes. Tetrakis (triphenylphosphine) palladium(0) was added and the mixture was heated to 80° C. for 4 hours. The reaction mixture was taken up in ethyl acetate, washed twice with brine, and the volatiles were removed in vacuo. The product was purified on silica gel, using 50% ethyl acetate/hexanes as the mobile phase, to give 13.5 mg of 4-methyl-2-[6-propyl-2-(4-trifluoromethoxyphenyl)pyrimidin-4-ylamino] pentanoic acid (3-ethoxypropyl) amide. ESI-MS (m/z) 497 [M+H]$^+$.

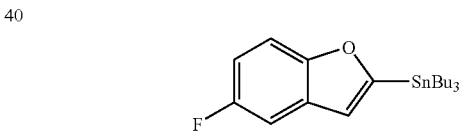

Butyllithium (1.5 mL, 2.4 mmol, 1.6 M) was added at −75° C. to a solution of 5-fluorobenzofuran (0.3 g, 2.2 mmol) in THF (10 mL). Tributyltin chloride (0.98 g, 1 mL) was added at −75° C. and the mixture was allowed to warm to 25° C. over a period of 2 hours. Water (25 mL) was added and the aqueous layer was extracted with diethyl ether (2×25 mL). The combined organic extracts were dried over Na$_2$SO$_4$ and concentrated. Silica gel chromatography (pentane) provided tributyl-(5-fluorobenzofuran-2-yl)-stannane (210 mg).

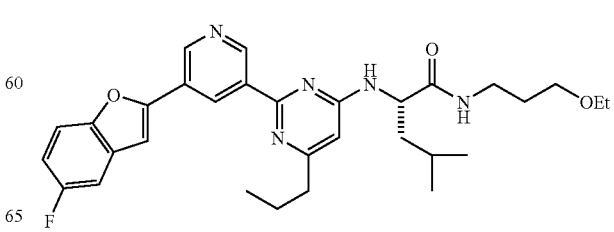

Under an atmosphere of argon, a solution of tributyl(5-fluorobenzofuran-2-yl)stannane (17 mg), 2-[2-(5-bromopyridin-3-yl)-6-butylpyrimidin-4-ylamino]-4-methylpentanoic acid (3-ethoxypropyl)amide (20 mg) and (PPh$_3$)$_2$PdCl$_2$ (2 mg) in N,N-dimethylformamide (1 mL) was heated at 80° C. for 12 h and then quenched with water (10 mL). The mixture was extracted with ethyl acetate (3×20 mL) and the combined organic extracts were dried over sodium sulfate and concentrated. The crude product was purified by semi-preparative HPLC to give 4.6 mg of 2-{2-[5-(5-fluorobenzofuran-2-yl)pyridin-3-yl]-6-propylpyrimidin-4-ylamino}-4-methylpentanoic acid (3-ethoxypropyl) amide as a TFA salt. ESI-MS (m/z) 562 [M+H]$^+$.

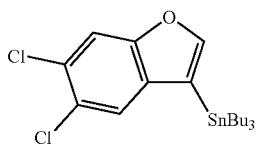

At −75° C., n-butyllithium (1.6 M in hexane, 1.0 mL) was added to a solution of 3-bromo-5,6-dicholorofuran (0.4 g, 1.5 mmol) in diethyl ether (40 mL). After 1 min, tributyltin chloride (0.5 g, 0.41 mL) in diethyl ether was added and the reaction mixture was allowed to warm to rt over 2 h. Water (2 mL) was added to quench the reaction. The organic layer was washed with water (15 mL), dried and evaporated. The crude product was then purified by column chromatography to afford tributyl-(5,6-dichloro-benzofuran-3-yl)stannane (400 mg, 0.84 mmol, 56%).

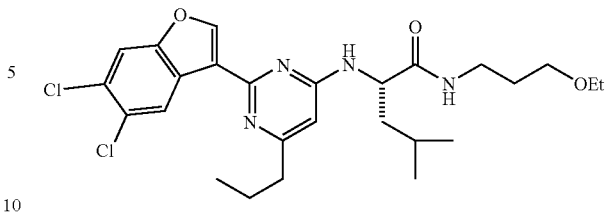

A mixture of tributyl-(5,6-dichloro-benzofuran-3-yl)-stannne (0.4 g, 0.8 mmol), 2-[2-choloro-6-butylpyrimidin-4-ylamino]-4-methylpentanoic acid (3-ethoxy-propyl)amide (100 mg), (PPh$_3$)$_2$PdCl$_2$ (8 mg) and potassium carbonate (1 g) in DMSO (8 mL) was stirred at 80° C. for 12 h. The reaction was quenched with water (10 mL) and the mixture was extracted with ethyl acetate (3×20 mL). The combined organic extracts were dried over sodium sulfate and concentrated. The crude product was purified by semi-preparative HPLC to give 13 mg of 2-[2-(5,6-dichlorobenzofuran-3-yl)-6-propylpyrimidin-4-ylamino]-4-methyl-pentanoic acid (3-ethoxypropyl) amide as a TFA salt.

The —N(R$^9$)(CH$_2$)$_m$C(R$^1$R$^2$)(CH$_2$)$_n$R$^4$ groups can be prepared by coupling of a protected amino acid (e.g. Boc amino acid) with an amine using a coupling reagent (e.g. DCC, EDCI) well known in the literature (Scheme 23A). Removal of the amino protecting group gave a primary amine which can then be used to react with the chloropyrimidines, dichloropyrimidines and triflate derivatives of pyrimidine shown in the previous sections. Alternatively, an amino acid tert-butyl ester can be reacted with a 4-chloropyrimidine derivative (Scheme 23B). Removal of the tert-butyl ester followed by coupling with an amine yields compounds of the invention.

Scheme 23

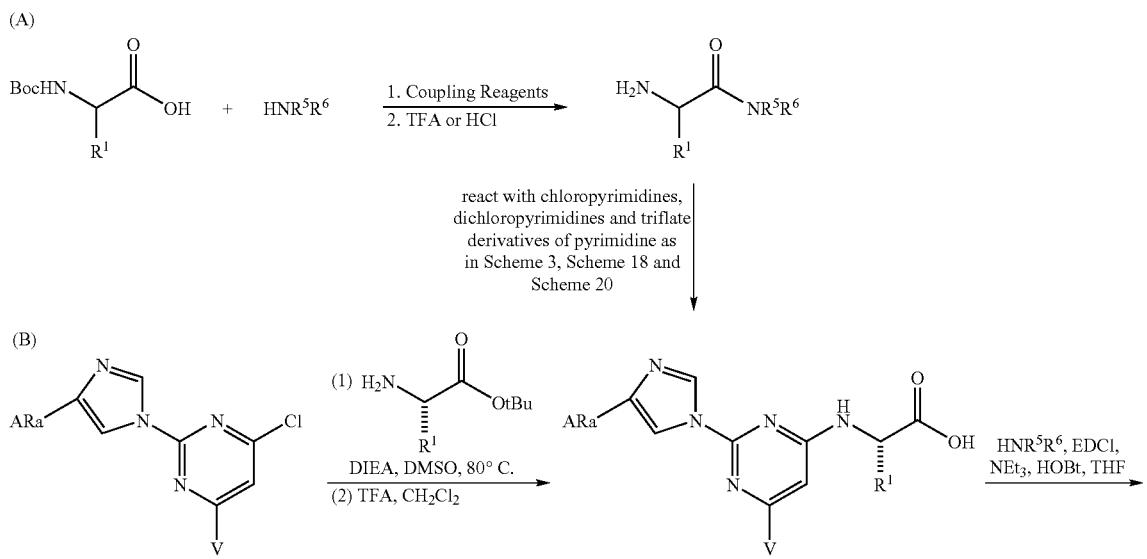

-continued

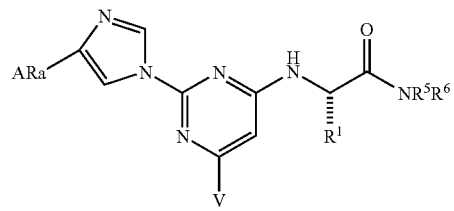

Representative procedures for Scheme 23B are as follows:

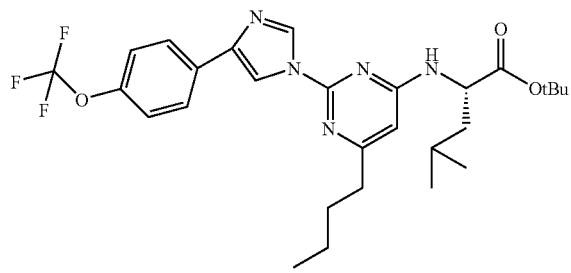

L-Leucine tert-butyl ester hydrochloride (291 mg) was dissolved in DMSO (5 mL) under an argon atmosphere and treated with diisopropylethylamine (450 μL, 2.6 mmol, 4 eq.) followed by 4-Butyl-6-chloro-2-[4-(4-trifluoromethoxy-phenyl)-imidazol-1-yl]-pyrimidine (274 mg). The mixture was heated to 80° C. for 48 h. DMSO and the volatiles were removed in vacuo to give a crude residue from which 2-{6-butyl-2-[4-(4-trifluoromethoxyphenyl) imidazol-1-yl] pyrimidin-4-ylamino}-4-methyl-pentanoic acid tert-butyl ester (321 mg) was isolated by flash chromatography (n-hexanes/ethyl acetate 4/1).

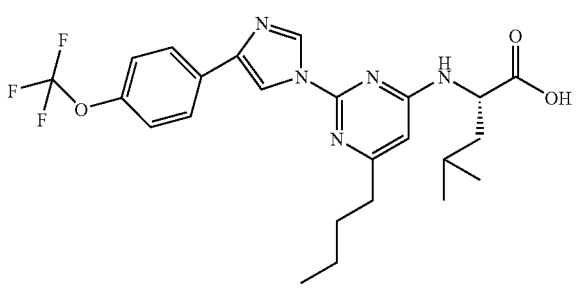

The tert-butyl ester above was dissolved in dichloromethane (7 mL) and treated with TFA (3 mL) at rt for 4 h. The solution was concentrated in vacuo to yield a crude TFA salt from which 2-{6-Butyl-2-[4-(4-trifluoromethoxyphenyl) imidazol-1-yl]pyrimidin-4-ylamino}-4-methylpentanoic acid. (210 mg) was isolated by flash chromatography (n-hexanes/ethyl acetate 3/1).

Some HNR⁵R⁶ used in Scheme 23 are not commercially available. For example, 4,4,4-trifluorobutylamine was synthesized via reductive animation of 4,4,4-trifluorobutyraldehyde using a literature procedure (*J. Am. Chem. Soc.*, 1971, 93, 2897). N-(3-aminopropyl)-N,O-dimethylhydroxylamine was synthesized in 2 steps by alkylation of N,O-dimethylhydroxylamine with N-(3-bromopropyl)phthalimide (Scheme 24) followed by removal of the phthalimide protecting group with hydrazine (*J. Org. Chem.*, 1978, 43, 2320). The procedures to prepare 2-[3-(methoxymethylamino)propyl]isoindole-1,3-dione are shown below.

Scheme 24

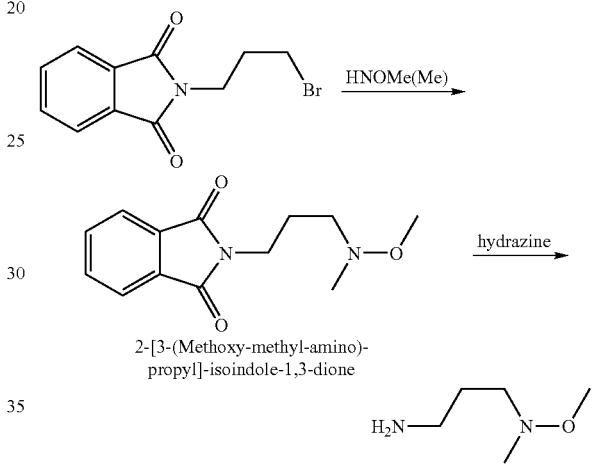

2-[3-(Methoxy-methyl-amino)-propyl]-isoindole-1,3-dione

A stirred mixture of N,O-dimethylhydroxylamine hydrochloride (5.6 g), N-(3-bromopropyl)phthalimide (3.0 g), and potassium carbonate (15.5 g) was heated at 55° C. for 24 h in DMSO. The mixture was partitioned between water and ethyl acetate. The ethyl acetate was separated and washed 3 times with brine. The ethyl acetate was evaporated to provide a 3:1 mixture of desired product and unreacted bromide. This crude material was converted to the HCl salt with 0.6 M HCl in 95% ethanol and the resulting oil was partitioned between 1 N HCl and ethyl ether. The ethyl ether portion was washed twice with 1 N HCl. The combined HCl washes were made basic with NaOH and extracted with methylene chloride. The methylene chloride was dried with sodium sulfate and evaporated to provide 2-[3-(methoxymethylamino)propyl]isoindole-1,3-dione (200 mg).

Synthetic procedures for additional examples of HNR⁵R⁶ are as follow:

To a 20% potassium hydroxide solution (25 mL) at 0° C. was added nitromethane (2.7 mL, 50 mmol) over 5 min followed by the slow addition via syringe pump of 2-furaldehyde (4.1 mL, 50 mM). The resulting brown solution was stirred vigorously for an additional 10 min at 0° C. then poured into an ice cold 50% HCl solution. The precipitate was collected via filtration, thoroughly washed with water, taken up in MeOH, solvents removed under reduced pressure, taken up in CHCl₃ and filtered to remove any material that did not dissolve to give 2-(2-nitrovinyl)furan (10% yield).

2-(2-Nitrovinyl)furan (0.62 g, 4.4 mM) in anhydrous Et₂O (10 mL) was added via double ended needle to an ice-cold solution of LAH (8.9 mL, 1.0M/Et₂O) diluted with Et₂O (25 mL). After the addition was complete the mixture was removed from the ice bath and heated at a gentle reflux overnight. The cooled mixture was quenched by the careful addition of water (0.35 mL), 10% NaOH (0.53 mL) and water (1.0 mL). Celite was added to the precipitate, which was filtered and solids thoroughly rinsed with Et₂O, dried (MgSO₄) filtered and solvents removed to yield 2-(furan-2-yl)ethanamine (68%). ESI-MS (m/z) 112 [M+H]⁺.

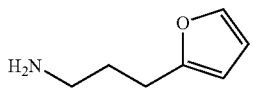

At 0° C., butyllithium (70 mL, 1.6 M in hexane) was added to a solution of furan (10 g, 0.15 mol) in THF (150 mL). The mixture was stirred at 0° C. for 1h, then treated with a solution of 1,3-dibromopropane (30 g, 0.15 mol) in THF (50 mL). The mixture was allowed to warm to 25° C. over 2 h, then quenched with a saturated NH₄Cl solution (50 mL). The aqueous phase was extracted with diethyl ether (3× 50 mL) and the combined organic extracts was dried over Na₂SO₄. The solvent was evaporated to give crude 2-(3-bromopropyl)furan (30 g), which was purified by silica gel chromatography (10% methylene chloride in hexanes). A mixture of 2-(3-bromopropyl)furan (7.6 g, 40 mmol) and sodium azide (10 g, 150 mmol) in DMF (200 mL) was stirred for 15 h at 90 C. Water (250 mL) was then added and the mixture was extracted by diethyl ether (3×100 mL). The combined organic extracts was washed with water (3×50 mL) and dried over sodium sulfate. The solvent was removed to give pure 2-(3-azidopropyl)-furan as an oil (5 g). A mixture of 2-(3-azidopropyl)furan (0.5 g) and Pd/C (0.05 g, 10%) in methanol (15 mL) was stirred at 25° C. for 8 h under a hydrogen atmosphere. The catalyst was filtered off and solvent was evaporated to give 3-Furan-2-yl-propylamine in quantitative yield.

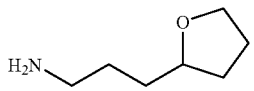

To thoroughly dried ground 4 Å molecular sieves (5 g) was added anhydrous CH₂Cl₂ (20 mL) and 4-methylmorpholine-N-oxide (NMO) (1.76 g, 15 mmol). The mixture was stirred at 0° C. for 15 min, then tetrahydrofurfuryl alcohol (0.97 mL, 10 mmol) and tetrapropylammonium perruthenate (TPAP) (0.17 g, 0.5 mmol) were added and the mixture stirred for 60 min. The solvent volume was reduced and then the entire reaction contents was passed through a short silica gel column with 50% Et₂O/H elutant to yield tetrahydrofuran-2-carbaldehyde (approx 50% yield, together with a dimeric product).

The crude aldehyde (assumed 5 mM), (cyanomethyl) triphenylphosphonium chloride (1.77 g, 5.3 mmol), DBU (0.82 mL, 5.5 mmol) in toluene (50 mL) were heated at reflux for 60 min, then the reaction volume was reduced in vacuo and the entire reaction contents added to a silica gel column. Elution with 20% ethyl acetate/hexanes gave 3-(tetrahydro-furan-2-yl)-acrylonitrile (50%) as a 4:3 mixture (¹H NMR) of the E/Z isomers.

Raney Ni (approx 1 mL) was added to 3-(tetrahydro-furan-2-yl)-acrylonitrile (0.43 g, 3.5 mmol) in THF (6 mL), the mixture was evacuated then charged with 1 atm H₂ (balloon) then stirred overnight. The mixture was recharged with Raney Ni (1 mL) and H₂ and stirring was continued an additional 24 hour, until no starting material was evident via TLC. The reaction contents were filtered through a celite plug, that was thoroughly rinsed with MeOH, solvents removed to yield 3-(Tetrahydro-furan-2-yl)-propylamine (51% yield). ESI-MS (m/z) 130 [M+H]⁺.

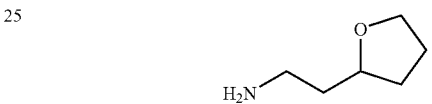

Tetrahydrofurfuryl alcohol (2.01 g, 19.7 mmol, 1.0 eq.) was dissolved in dichloromethane (100 mL) under an argon atmosphere, cooled to 0° C. and treated sequentially with triethylamine (3.02 mL, 21.7 mmol, 1.1 eq) and methanesulfonyl chloride (1.60 mL, 20.7 mmol, 1.05 eq.). The ice bath was removed and stirring continued for 14 h before the mixture was poured into a separatory funnel containing water. The phases were separated and the organic layer was washed with water (4×), dried on MgSO4, filtered and concentrated in vacuo to yield 3.26 g [92%] of tetrahydrofurfuryl methanesulfonate as a crude pale yellow oil, used in the subsequent displacement step without purification.

Crude tetrahydrofurfuryl methanesulfonate from above (1.0 g, 5.56 mmol, 1.0 eq.) was dissolved in DMSO (5 mL) under an argon atmosphere and treated with NaCN (817 mg, 16.7 mmol, 3 eq.) at 80° C. for 3.5 h. The mixture was cooled to rt, diluted with diethyl ether and shaken with sat. aq. NaCl. The brine was separated and extracted with diethyl ether (4×). The combined organic phases were dried on MgSO₄, filtered and concentrated carefully in vacuo [NB: suspected volatility of product] to give a crude oil from which the carbonitrile product [247 mg, 40%] was isolated by flash chromatography (20–50% ethyl acetate in n-hexanes). Tetrahydro-2-furanacetonitrile from above (75 mg, 670 μmol, 1.0 eq.) was treated under argon atmosphere with BH₃-THF (0.5 mL, 5 mmol, excess; 1.0 M in THF) for 2 h at rt. The solution was rotoevaporated to a crude oil which was carefully treated with MeOH and then rotoevaporated once again. The residue was treated with MeOH (0.5 mL) and 1.0 N aq. HCl (0.5 mL) overnight at rt and then concentrated in vacuo. Pure 3-(tetrahydrofuran-2-yl) ethylamine (33 mg, 43%) was isolated from the crude oil by flash chromatography (0–10% MeOH in dichloromethane +1–2% NH₄OH). ESI-MS (m/z) 116 [M+H]⁺.

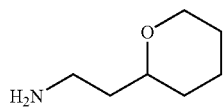

2-(Bromomethyl)tetrahydropyran (100 μL), sodium cyanide (191 mg), and tetrabutylammonium iodide (100 mg) were stirred at 80 C. in 3 mL DMSO for 3 hours. The mixture was cooled and partitioned between ethyl ether and brine. The ethyl ether phase was washed once more with brine, dried and evaporated to provide the crude intermediate nitrile (110 mg). This material was dissolved in ethyl ether and treated with lithium aluminum hydride (125 mg). The mixture was stirred for 3 days, then quenched at 0 C. with the sequential addition of 0.125 mL water, 0.125 mL 3 M NaOH, and 0.375 mL more water. After 15 minutes of vigorous stirring the mixture was filtered to provide, after solvent evaporation, 2-(tetrahydropyran-2-yl) ethylamine (91 mg).

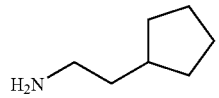

Triethylamine (2.1 mL, 15 mM) and methanesulfonyl chloride (0.85 mL, 11 mM) were added drop wise to a cold (−5 to −10° C.) solution of 2-(tetrahydro-furan-3-yl)-ethanol (1.14 g, 10 mM) in dichloromethane (15 mL). The reaction was stirred for 20 min at this temp then water (10 mL) was added and the reaction was stirred an additional 10 min then the phases were separated and the aqueous phase was extracted with dichloromethane (3×20 mL). The combined organics were washed with 50% aqueous HCl, sat. NaHCO$_3$, dried (MgSO$_4$), filtered and concentrated to give a quantitative yield of methanesulfonic acid 2-(tetrahydrofuran-3-yl)-ethyl ester.

The crude mesylate (2.03 g, 10 mM), sodium azide (3.25 g, 50 mM) and DMF were combined and heated at 80° C. for 2 hr, cooled to rt then the mixture was diluted with EA and thoroughly washed with water (3×100 mL) and brine. The organics were dried, filtered and concentrated then passed through a short silica gel column eluted with 30% ethyl acetate/hexanes to yield 3-(2-azido-ethyl) tetrahydro-furan (1.04 g, 75%). A catalytic amount of 10% palladium on carbon was added to a methanolic solution of the azide (1.04 g, 7.5 mM), the reaction flask was then briefly evacuated under house vacuum and H$_2$ was added via a balloon. The reaction was stirred at rt overnight under an atmosphere of H$_2$, filtered through a plug of celite, which was thoroughly rinsed with MeOH. One molar HCl in Et$_2$O (10 mL) was added then the volatiles were removed to give 2-(cyclopentyl)ethylamine as the HCl salt (51% yield). ESI-MS (m/z) 114 [M+H]$^+$.

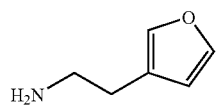

A freshly prepared solution of sodium methoxide (prepared by dissolving sodium (0.46 g, 20 mmol) in MeOH (5 mL)) was added very slowly via a double ended needle to a solution of 3-furaldehyde (1.73 mL, 20 mM) and nitromethane (1.08 mL, 20 mmol) in MeOH (4 mL) cooled to 0° C. The mixture was stirred at 0° C. an addition 5 min, then Et$_2$O (10 mL) was added. The resultant salt was collected via filtration, thoroughly washed with Et$_2$O, taken up in a minimum amount of water then the solution was added to an ice cold solution of 25% HCl (80 mL). The solid that formed was collected by filtration and washed with water, then the moist product was taken up in CHCl$_3$/MeOH and solvents removed to give 3-(2-nitrovinyl) furan (69%) as a pale yellow solid.

The same LAH reduction procedure as that described above for the reduction of 2-(2-nitro-vinyl)-furan was followed to give 2-Furan-3-yl-ethylamine. in 61% yield. ESI-MS (m/z) 112 [M+H]$^+$.

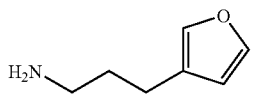

Wittig reaction of 3-furaldehyde (0.43 mL, 5 mmol) with (cyanomethyl)triphenylphosphonium chloride as described above gave 3-furan-3-yl)-acrylonitrile (quant) as a 5:1 mixture ($^1$H NMR) of the E/Z isomers after column chromatography (15% EA/H elutant). Hydrogenation of 3-furan-3-yl)-acrylonitrile with Raney Ni as described above gave a product mixture (64%) (MS, m/z 126.1 (MH$^+$), 130.2, 234.1) that was purified via column chromatography. Elution with 10% MeOH/CH$_2$Cl$_2$ gave bis-(3-furan-3-yl-propyl)-amine (ESI-MS (m/z) 234 [M+H]$^+$), elution with 1% NH$_4$OH/10% MeOH/CH$_2$Cl$_2$ gave 3-Furan-3-yl-propylamine (ESI-MS (m/z) 126 [M+H]$^+$) together with approx 10% ($^1$H NMR) of over reduction product 3-(tetrahydrofuran-3-yl)-propylamine (ESI-MS (m/z) 130 [M+H]$^+$).

Dichloromethane extraction of tetrahydrofuran-3-carboxaldehyde in water (50%, 2 mL) gave pure aldehyde (0.72 g, 7.2 mM) that was reacted with nitromethane in an analogous manner as used for the preparation of 2-Furan-3-yl-ethylamine above, to yield 3-(2-Nitrovinyl)-tetrahydrofuran (0.57 g, 55% yield) after column chromatography (elution with 30% ethyl acetate/Hexanes). The vinyl-nitro compound was reduced with LAH as described for the synthesis of 2-(furan-2-yl-)ethylamine, except that 1 M HCl/Et$_2$O (5 mL) was added to the filtered solvent prior to evaporation to yield 2-(Tetrahydrofuran-3-yl) ethylamine as the HCl salt (30% yield). ESI-MS (m/z) 116 [M+H]$^+$.

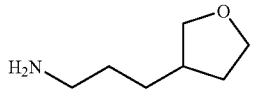

Tetrahydro-3-furanmethanol (0.96 mL, 10 mmol) was oxidized to tetrahydrofuran-3-carbaldehyde (assume 50%) via the TPAP/MNO oxidation procedure described for 3-(tetrahydro-furan-2-yl)-propylamine. Wittig reaction of the crude aldehyde with (cyanomethyl)triphenylphosphonium chloride as described for 3-(tetrahydrofuran-2-yl)propylaamine gave 3-(tetrahydrofuran-3-yl)acrylonitrile (3.3 mmol) as a 2:1 mixture ($^1$H NMR) of the E/Z isomers after column chromatography (10% Et$_2$O/CH$_2$Cl$_2$ elutant). Hydrogenation of 3-(tetrahydrofuran-3-yl)acrylonitrile in the presence of Raney Ni as detailed for 3-(tetrahydro-furan-2-yl)-propylamine gave 3-(tetrahydrofuran-3-yl) propylamine. (33% yield). ESI-MS (m/z) 130 [M+H]$^+$.

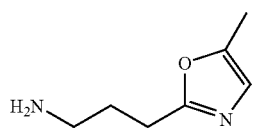

To a mixture of 4-tert-butoxycarbonylaminobutyric acid (5 g), 1-(3-dimethylaminopropyl)-3-ethylcarbodiimide hydrochloride (5.66 g) and triethylamine (7.47 g) in dichloromethane (80 mL) at rt was added 2-propynylamine (1.49 g). After being stirred at rt for 3 h, the mixture was diluted with dichloromethane (80 mL) and washed with 0.5 M HCl (aqueous, 2×), saturated NaHCO$_3$ (1×) and water (1×). The dichloromethane was dried over sodium sulfate, filtered and evaporated to afford (3-Prop-2-ynylcarbamoyl-propyl)-carbamic acid tert-butyl ester (1.67 g).

Sodium hydride (60 mg, 60% dispersion) was added to a mixture of (3-prop-2-ynylcarbamoylpropyl)carbamic acid tert-butyl ester (0.5 g) and dimethylsulfoxide (10 mL) under argon. The mixture was stirred at rt for 4 h. Saturated aqueous ammonium chloride (30 mL) was added to quench the reaction and the mixture was extracted with ethyl acetate (2×). Combined ethyl acetate layers were washed with water (1×), dried over sodium sulfate, filtered and evaporated. The crude product was purified by column chromatography (20 to 30% ethyl acetate in hexanes) to give [3-(5-methyloxazol-2-yl)-propyl]carbamic acid tert-butyl ester (150 mg). HCl in dioxane (4M, 3 mL) was added to [3-(5-methyl-oxazol-2-yl)-propyl]-carbamic acid tert-butyl ester (250 mg). The mixture was stirred at rt for 2 h and was evaporated to dryness in vacuo to give the HCl salt of 3-(5-Methyloxazol-2-yl)propylamine (228 mg). ESI-MS (m/z) 141 [M+H]$^+$.

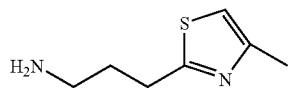

To a round-bottom flask containing N-Boc-γ-aminobutyric acid (2.5 g, 12.3 mmol, 1.0 eq) and 1,1'-carbonyl duimidazole (2.10 g, 12.9 mmol, 1.05 eq) was added dichloromethane (50 mL, anhydrous). The clear, colorless solution was stirred at rt for 5 min., then cooled to 0° C. Dry ammonia was bubbled into the solution for 2 min., yielding a turbid white mixture. The ice bath was removed and stirring continued for 45 min. Argon was bubbled through the suspension to purge excess ammonia and the flask contents were carefully concentrated in vacuo. N-Boc-γ-aminobutyramide (2.5 g) was isolated from the crude residue by flash chromatography [0–4% methanol in dichloromethane]. ESI-MS (m/z) 203 [M+H]$^+$, 225 [M+Na]$^+$, 427 [dimer+Na]$^+$.

The butyramide from above (2.35 g, 11.6 mmol, 1.0 eq) was suspended in dichloromethane (75 mL, anhydrous) at rt under argon and treated with Lawesson's reagent (2.6 g, 6.4 mmol, 0.55 eq). After stirring for 4 h, the mixture was concentrated in vacuo to yield a yellow suspension/oil from which the corresponding thioamide (400 mg, 16%) was isolated by flash chromatography (30–50% ethyl acetate in n-hexanes). ESI-MS (m/z) 219 [M+H]$^+$, 241 [M+Na]$^+$. The thioamide from above (0.36 g, 1.63 mmol, 1.0 eq) was suspended in EtOH (10 mL, absolute) under argon at rt. 1-Bromo-2,2-dimethoxypropane (0.22 mL, 1.63 mmol, 1.0 eq) was added via syringe and stirring continued for 72 h at rt. The mixture was then heated to 70° C. for 16 h and concentrated in vacuo. Mass spectrometric analysis of the crude residue was consistent with a corresponding thiazole structure, and no further manipulation was performed before removal of the Boc protecting group in the next step. ESI-MS (m/z) 257 [M+H]$^+$, 201 [M-$^t$Bu]$^+$, 157 [M-Boc]$^+$.

Crude thiazole from above was dissolved in dichloromethane (2 mL, anhydrous) under argon at rt and treated with TFA (2 mL, anhydrous). The mixture stirred for 1 h and was then concentrated in vacuo to give a crude brown oil from which 3-(4-Methylthiazol-2-yl) propylamine (236 mg, 93% from thioamide) was isolated by flash chromatography (MeOH 0–20% in dichloromethane).

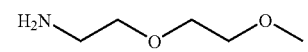

Di-tert-butyl dicarbonate (11 g) was added to a solution of 2-(2-hydroxy-ethoxy)-ethylamine (5.3 g) in methylene chloride (200 mL). After 1 hour, the solvents were evaporated to provide the N-tert-butoxycarbonyl derivative (10.5 g). The Boc-protected intermediate (1.0 g) was dissolved in 50 mL THF, cooled to 0 C, and treated with NaH (60% w/w in mineral oil, 0.6 g) followed by iodomethane (0.3 mL). The mixture was stirred for 3 hours at 0 C, then quenched by the addition of saturated aqueous ammonium chloride. The mixture was extracted with ethyl ether (2×100 mL) and the extracts washed with brine (1×100 mL). The crude residue isolated from the extracts was chromatographed on silica gel (30% ethyl acetate in hexanes) to provide 0.4 g of N-(tert-butyloxycarbonyl)-2-(2-methoxyethoxy) ethylamine. The Boc group was removed by dissolving the compound in 1:1 methylene chloride/TFA and stirring for 0.5 h, then evaporating the solvent to give 2-(2-methoxyethoxy) ethylamine.

Three pyrimidines used extensively in the invention were not commercially available and required synthesis. In one case, 2,4-dichloro-6-ethylpyrimidine was synthesized by alkylation of 2,4-dichloro-6-methylpyrimidine using LDA and iodomethane (Scheme 25). In another case, 2,4-dichloro-6-propyl pyrimidine was synthesized by refluxing 4-hydroxy-2-mercapto-6-propylpyrimidine in phosphorous oxychloride (Scheme 26).

Scheme 25

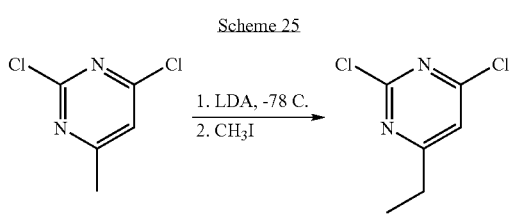

A solution of 2,4-dichloro-6-methylpyrimidine (4.0 g) in 90 mL THF was cooled to −78 C and treated dropwise with LDA (2 M, 14.7 mL). After 35 min, iodomethane (1.55 mL) was added and the reaction was stirred for 3 more hours at −78 C. The reaction was allowed to slowly warm to room temperature, then quenched with 0.5 mL of water. The mixture was dissolved in water and extracted with ethyl acetate. Chromatography (30% ethyl acetate in hexanes) provided 1.64 g of 2,4-Dichloro-6-ethylpyrimidine.

Scheme 26

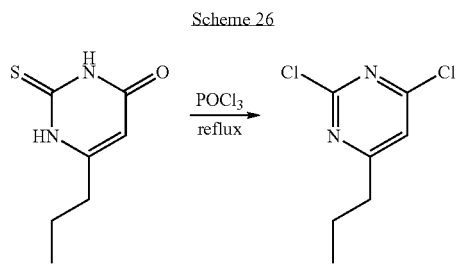

A solution of 4-hydroxy-2-mercapto-6-propylpyrimidine (17.7 g) in phosphorous oxychloride (100 mL) was refluxed for 24 h. The phosphorous oxychloride was evaporated to give an oil which was neutralized with aqueous sodium bicarbonate and extracted with ethyl acetate. Chromatography (2% ethyl acetate in hexanes) provided 7.5 g of 2,4-Dichloro-6-propylpyrimidine.

4-Butyl-2,6-dichloro-pyrimidine was prepared from 2,4-dichloro-pyrimidine by literature procedures (*J. Org. Chem.* 1988, 53(17), 4137).

General Procedures for the preparation of sulfinyl- and sulfonyl-amine containing products are outlined in Scheme 27.

Scheme 27

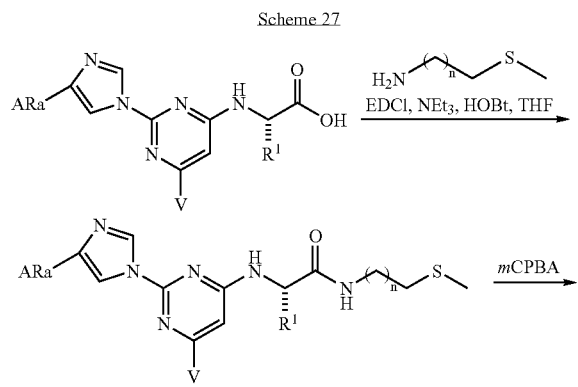

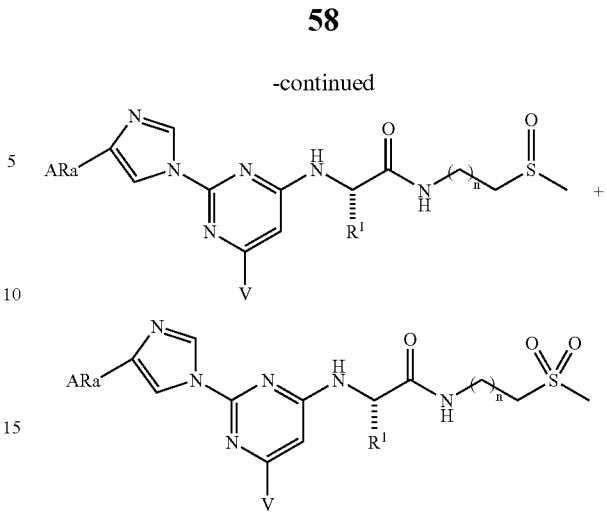

Commercially available sulfanyl-amines were coupled with the acid by standard coupling conditions. 3-Chloroperoxybenzoic acid (77%, 1 equiv.) was added to the purified amide in dichloromethane and stirred at rt for 1 hr, at which time one half of the reaction mixture was removed, quenched with the addition of sat. NaHCO$_3$ and set aside. An additional equivalent of 3-chloroperoxybenzoic acid (based on original stoichiometry) was added to the remaining reaction mixture, then stirred overnight and quenched in the same manner. The two reaction mixtures were combined, extracted with CH$_2$Cl$_2$, and then the combined organics were washed with water, dried, filtered and evaporated. The sulfinyl- and sulfonyl-amine products were then easily separated via column chromatography, with the sulfone eluting first with ethyl acetate followed by the sulfoxide with 5 to 10% MeOH/EA.

In this manner, products containing 2-methylsulfanyl-ethyl-, 2-methanesulfinyl-ethyl-, 2-methanesulfonyl-ethyl-, 3-methylsulfanyl-propyl-, 3-methanesulfinyl-propyl-, 3-methanesulfonyl-propyl-, 2-Thiomorpholin-4-yl-ethyl- and 2-(1-Oxo-$\lambda^4$-thiomorpholin-4-yl)-ethyl-amides were prepared.

Synthetic procedures of three representative examples with modifications in the V group are shown as follows (scheme 28 and 29):

Scheme 28

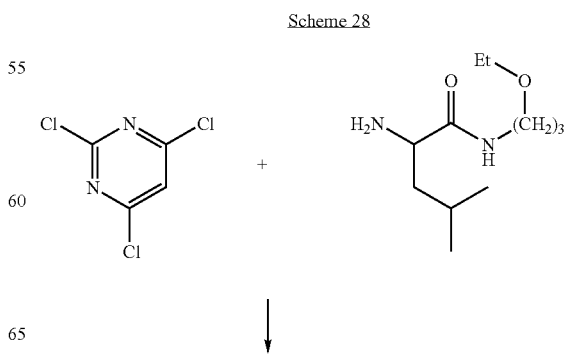

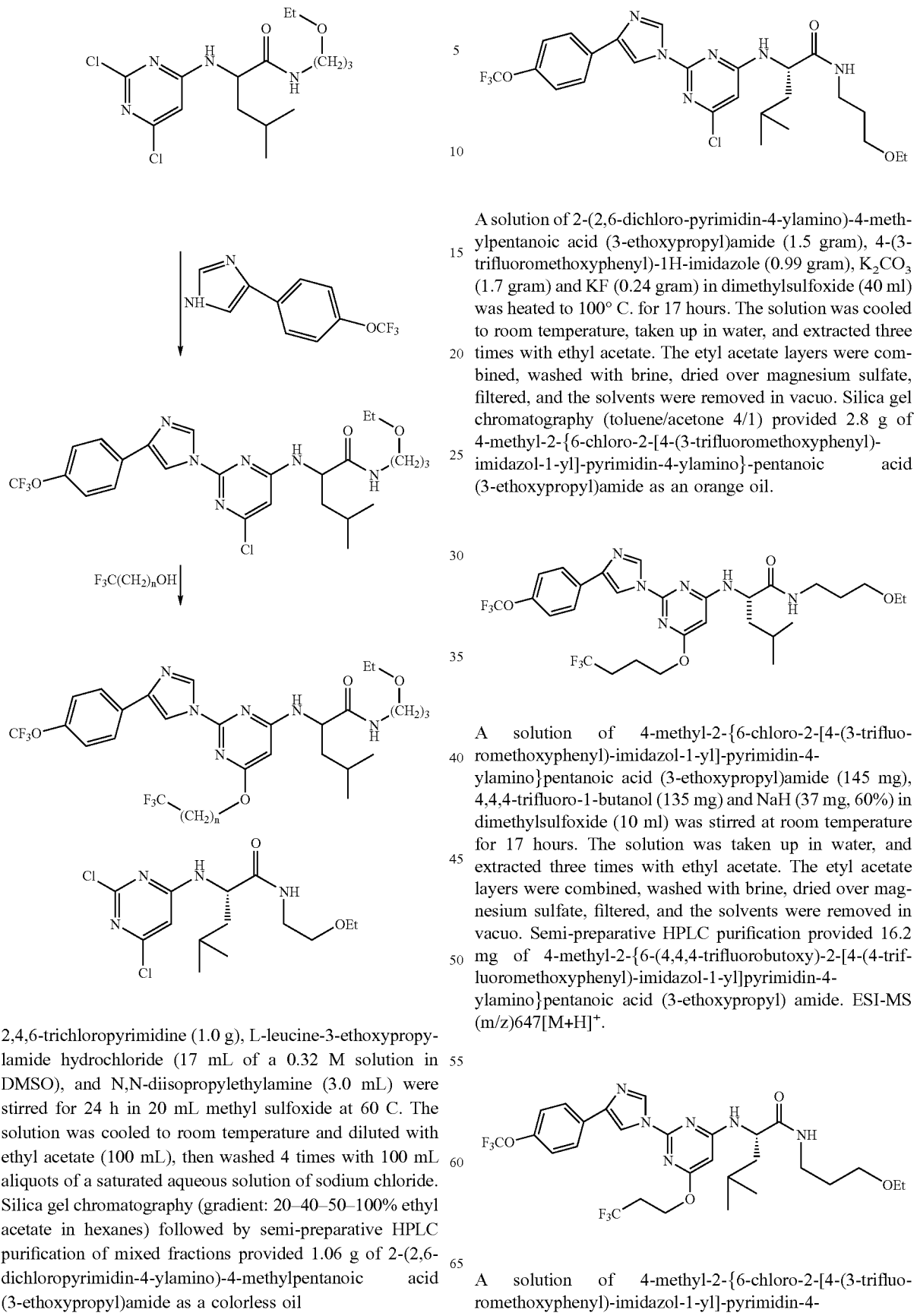

2,4,6-trichloropyrimidine (1.0 g), L-leucine-3-ethoxypropylamide hydrochloride (17 mL of a 0.32 M solution in DMSO), and N,N-diisopropylethylamine (3.0 mL) were stirred for 24 h in 20 mL methyl sulfoxide at 60 C. The solution was cooled to room temperature and diluted with ethyl acetate (100 mL), then washed 4 times with 100 mL aliquots of a saturated aqueous solution of sodium chloride. Silica gel chromatography (gradient: 20–40–50–100% ethyl acetate in hexanes) followed by semi-preparative HPLC purification of mixed fractions provided 1.06 g of 2-(2,6-dichloropyrimidin-4-ylamino)-4-methylpentanoic acid (3-ethoxypropyl)amide as a colorless oil A solution of 2-(2,6-dichloro-pyrimidin-4-ylamino)-4-methylpentanoic acid (3-ethoxypropyl)amide (1.5 gram), 4-(3-trifluoromethoxyphenyl)-1H-imidazole (0.99 gram), $K_2CO_3$ (1.7 gram) and KF (0.24 gram) in dimethylsulfoxide (40 ml) was heated to 100° C. for 17 hours. The solution was cooled to room temperature, taken up in water, and extracted three times with ethyl acetate. The etyl acetate layers were combined, washed with brine, dried over magnesium sulfate, filtered, and the solvents were removed in vacuo. Silica gel chromatography (toluene/acetone 4/1) provided 2.8 g of 4-methyl-2-{6-chloro-2-[4-(3-trifluoromethoxyphenyl)-imidazol-1-yl]-pyrimidin-4-ylamino}-pentanoic acid (3-ethoxypropyl)amide as an orange oil.

A solution of 4-methyl-2-{6-chloro-2-[4-(3-trifluoromethoxyphenyl)-imidazol-1-yl]-pyrimidin-4-ylamino}pentanoic acid (3-ethoxypropyl)amide (145 mg), 4,4,4-trifluoro-1-butanol (135 mg) and NaH (37 mg, 60%) in dimethylsulfoxide (10 ml) was stirred at room temperature for 17 hours. The solution was taken up in water, and extracted three times with ethyl acetate. The etyl acetate layers were combined, washed with brine, dried over magnesium sulfate, filtered, and the solvents were removed in vacuo. Semi-preparative HPLC purification provided 16.2 mg of 4-methyl-2-{6-(4,4,4-trifluorobutoxy)-2-[4-(4-trifluoromethoxyphenyl)-imidazol-1-yl]pyrimidin-4-ylamino}pentanoic acid (3-ethoxypropyl) amide. ESI-MS (m/z)647[M+H]⁺.

A solution of 4-methyl-2-{6-chloro-2-[4-(3-trifluoromethoxyphenyl)-imidazol-1-yl]-pyrimidin-4- ylamino}pentanoic acid (3-ethoxypropyl)amide (100 mg), KF (20 mg), N,N-diisopropylethylamine (70 μL) and K₂CO₃ (55 mg) in 3,3,3-trifluoro-1-propanol (2 ml) was stirred at 80° C. for 17 hours. The solution was cooled to room temperature, taken up in water, and extracted three times with ethyl acetate. The etyl acetate layers were combined, washed with brine, dried over magnesium sulfate, filtered, and the solvents were removed in vacuo. Semi-preparative HPLC purification provided 18.5 mg of 4-methyl-2-{6-(3,3,3-trifluoropropoxy)-2-[4-(4-trifluoromethoxyphenyl) imidazol-1-yl]pyrimidin-4-ylamino} pentanoic acid (3-ethoxypropyl) amide. ESI-MS(m/z)634[M+H]⁺.

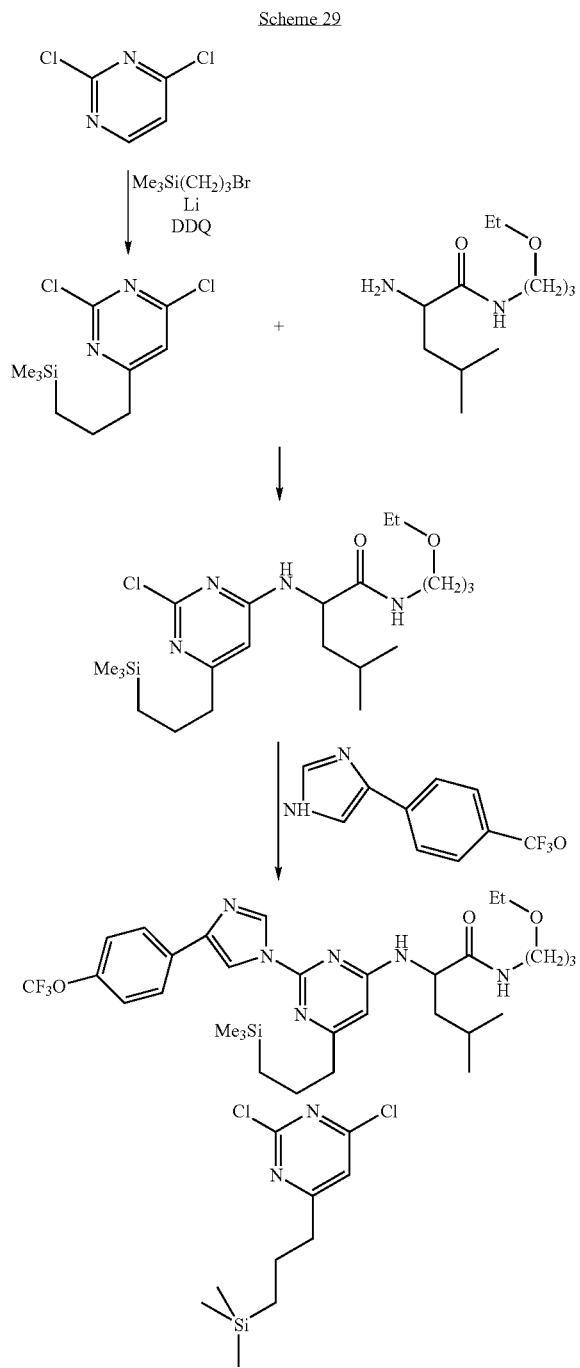

At −20° C. to a solution of Li (3 gram) in diethyl ether (150 ml) was slowly added 3-trimethylsilyl-propyl bromide (33.8 gram). Stirred for 30 min at −20° C. and 1 hour at 0° C. This solution was slowly added to a solution of 2,4 dichloro pyrimidine (19.3 gram) in diethyl ether (388 ml) at −30° C. stirred for 30 min at −30° C. and 30 mm at 0° C. to this solution was added glacial acid (11.1 ml), H₂O (1.15 ml) in THF (34.7 ml) and DDQ (29.7 gram) in THF (127 ml). Reaction mixture was stirred for 30 min. At 0° C. NaOH (3 m, 50 ml) and Na₂S₂O₃ (saturated solution, 200 ml) was added. The reaction mixture was stirred for 30 min and extracted two times with diethyl ether. The diethyl ether layers were combined, washed with brine, dried over magnesium sulfate, filtered, and the solvents were removed in vacuo. Silica gel chromatography (heptane/ethyl acetate 4/1) provided 23.6 g of 2,4-dichloro-6-[3-(trimethylsilyl) propyl] pyrimidine.

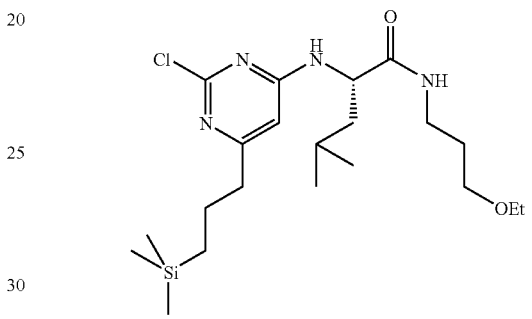

2,4-dichloro-6-[3-(trimethylsilyl)-propyl]pyrimidine (1 gram), L-leucine-3-ethoxypropylamide hydrochloride (1 gram) and N,N-diisopropylethylamine (2.3 mL) were stirred for 17 h in 20 mL dimethyl sulfoxide at 55° C. The solution was cooled to room temperature and diluted with ethyl acetate (100 mL), then washed 4 times with 100 mL aliquots of a saturated aqueous solution of sodium chloride, dried over magnesium sulfate, filtered, and the solvents were removed in vacuo. Silica gel chromatography (heptane/ethyl acetate 3/1) provided 978 mg of 2-(2-chloro- 6-[3-trimethylsilylpropyl]pyrimidin-4-ylamino)-4-methyl-pentanoic acid (3-ethoxypropyl)amide.

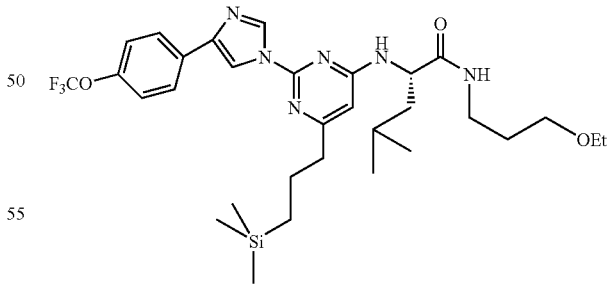

A solution of 2-(2-chloro-6-[3-trimethylsilyl-propyl]pyrimidin-4-ylamino)-4-methyl-pentanoic acid (3-ethoxy-propyl) amide (400 mg), 4-(3-trifluoromethoxy-phenyl)-1H-imidazole (413 mg), KF (55 mg) and K₂CO₃ (375 mg) in dimethyl sulfoxide (8 ml) was stirred at 100° C. for 17 hours. The solution was cooled to room temperature, taken up in water, and extracted three times with ethyl acetate. The etyl acetate layers were combined, washed with brine, dried over magnesium sulfate, filtered, and the solvents were removed in vacuo. Semi-preparative HPLC purification provided 340 mg of 4-methyl-2-{6-(3-trimethylsilylpropyl)-2-[4-(4-trifluoromethoxyphenyl)-imidazol-1-yl]pyrimidin-4-ylamino}pentanoic acid (3-ethoxypropyl)amide. ESI-MS (m/z)672[M+H]$^+$.

The following compounds, shown in Tables 1 through 8 are representative of the compounds of the invention and were synthesized by the foregoing methods. The appropriate M+1 peaks in mass spectroscopy were observed for each of the examples.

Biological Tests

The IL-8, and GROα chemokine inhibitory effects of compounds of the present invention are determined by the following in vitro assays:

Receptor Binding Assays:

[$^{125}$I] IL-8 (human recombinant) is obtained from Amersham Corp., Arlington Heights, Ill., with specific activity 2000 Ci/mmol. [$^{125}$I]GROα is obtained from NEN-New England Nuclear. All other chemicals are of analytical grade. High levels of recombinant human IL-8 type α and β receptors were individually expressed in Chinese hamster ovary cells as described previously [Holmes, et al., Science 253, 1278 (1991)]. The Chinese hamster ovary membranes were homogenized according to a previously described protocol (Haour, et al., J. Biol. Chem. 249, 2195–2205 (1974)], except that the homogenization buffer is changed to 10 mM Tris-HCL, 1 mM MgSO$_4$, 0.5 mM EDTA (ethylenediaminetetraacetic acid), 1 mM PMSF (α-toluenesulphonyl fluoride), 0.5 mg/L Leupeptin, pH 7.5. Membrane protein concentration was determined using Pierce Co. micro-assay kit using bovine serum albumin as a standard. All assays were performed in a 96-well micro plate format. Each reaction mixture contained [$^{125}$I] IL-8 (0.25 nM) or [$^{125}$I] GROα and 0.5 µg/mL of IL-8Rα or 1.0 µg/mL of IL-8Rβ membranes in 20 mM MgSO$_4$. 0;1,<EDTA. 25 mM NaCl and 0.03% CHAPS. The compound of interest, which had been pre-dissolved in DMSO so as to reach a final concentration of between 0.01 nM and 100 µM was added . The assay was initiated by addition of [$^{125}$I] IL-8. After 1 hour at room temperature the plate was harvested using a Tomtech 96-well harvester onto a glass fiber filtermat blocked with 1% polyethylenimine/0.5% BSA and washed 3 times with 25 mM NaCl, 10 mM TrisHCl, 1 mM MgSO$_4$. 0.5 mM EDTA, 0.03% CHAPS, pH 7.4. The filter was then dried and counted on the Betaplate liquid scintillation counter. The recombinant IL-8Rα, or Type I, receptor is also referred to herein as the non-permissive receptor and the recombinant IL-8 Rβ, or Type II, or CXCR2 receptor is referred to as the permissive receptor.

A slight modification was made in obtaining the data in Tables 4 to 11 (Compounds 701 to 1040). [$^{125}$I]-IL8 (human recombinant) was obtained from NEN-New England Nuclear, Boston, Mass. with a specific activity of 2200 Ci/mmol. Recombinant CXCR2 receptors were expressed in Chinese hamster ovary cells as described above and the Chinese hamster ovary membranes were homogenized as above except that a slightly different homgenization buffer was used: 10 mM Tris, pH=8, 1.2 mM MgSO$_4$, 0.1 mM EDTA, 25 mM NaCl and 1 unit/mL Bacitracin. Assays were performed in a 96-well micro plate as before, but the assay was changed slightly: each reaction contained [$^{125}$I] IL8 (0.1 nM) and 50 µg/mL of CXCR2 membranes in 1% DMSO, 10 mM Tris, pH=8, 1.2 mM MgSO$_4$, 0.1 mM EDTA, and 25 mM NaCl, 0.03% CHAPS. The assay was initiated by addition of CXCR2 membranes to the plate. After 1 hour at room temperature the plate was harvested using a Tomtech 96-well harvester onto a glass fiber filterplate (Millipore Corporation; Multiscreen-FC, Opaque plates, 1.2 µm type C filter; cat # MAFCNOB50) pre-wet with 0.3% polyethyleneimine and washed 3 times with 10 mM Tris pH=8, 1 mM MgSO$_4$, 0.5 mM EDTA, 25 mM NaCl, 0.5% BSA using 100 µL/well. Fifty microliters per well of scintillation cocktail is added to each well and the plate was counted on the Betaplate liquid scintillation counter.

Chemotaxis Assay:

The in vitro inhibitory properties of these compounds are determined in the neutrophil chemotaxis assay as described in Current Protocols in Immunology, vol. I, Suppl 1, Unit 6.12.3, whose disclosure is incorporated herein by reference in its entirety. The chemoattractants IL-8, GROα, GROβ, GROγ and NAP-2 are placed in the bottom chamber of a 48 multiwell chamber (Neuro Probe, Cabin John, MD) at a concentration between 0.1 and 100 nM. The two chambers are separated by a 5 µm polycarbonate filter. When compounds of this invention are tested, they are mixed with the cells (0.001–1000 nM) just prior to the addition of the cells to the upper chamber. Incubation is allowed to proceed for between about 45 and 90 min. at about 37° C. in a humidified incubator with 5% CO$_2$. At the end of the incubation period, the polycarbonate membrane is removed and the top side washed, the membrane then stained using the Diff Quick staining protocol (Baxter Products, McGraw Park, Ill., USA). Cells which have chemotaxed to the chemokine are visually counted using a microscope. Generally, four fields are counted for each sample, these numbers are averaged to give the average number of cells which had migrated. Each sample is tested in triplicate and each compound repeated at least four times. To certain cells (positive control cells) no compound is added, these cells represent the maximum chemotactic response of the cells. In the case where a negative control (unstimulated) is desired, no chemokine is added to the bottom chamber. The difference between the positive control and the negative control represents the chemotactic activity of the cells.

Elastase Release Assay:

The compounds of this invention are tested for their ability to prevent Elastase release from human neutrophils. Neutrophils are isolated from human blood as described in Current Protocols in Immunology Vol. I, Suppl 1 Unit 7.23.1. PMNs 0.88×10$^6$ cells suspended in Ringer's Solution (NaCl 118, KCl 4.56, NaHCO$_3$ 25, KH$_2$PO$_4$ 1.03, Glucose 11.1, HEPES 5 mM, pH 7.4) are placed in each well of a 96 well plate in a volume of 50 µl. To this plate is added the test compound (0.001–1000 nM) in a volume of 50 ul, Cytochalasin B in a volume of 50 µl (20 ug/mL) and Ringers buffer in a volume of 50 µl. These cells are allowed to warm (37° C., 5% CO$_2$, 95% RH) for 5 min. before Il-8, GROα, GROβ, GROγ or NAP-2 at a final concentration of 0.01–1000 nM was added. The reaction is allowed to proceed for 45 min. before the 96-well plate is centrifuged (800×g 5 min.) and 100 µl of the supernatant removed. This supernatant is added to a second 96 well plate followed by an artificial elastase substrate (MeOSuc-Ala-Ala-Pro-Val-AMC, Nova Biochem, LaJolla, Calif.) to a final concentration of 6 µg/ml dissolved in phosphate buffered saline. Immediately, the plate is placed in a fluorescent 96 well plate reader (Cytofluor 2350, Millipore, Bedford, Mass.) and data collected at 3 min. intervals according to the method of Nakajima et al. *J. Biol. Chem.* 254, 4027 (1979). The amount of elastase released from the PMNs is calculated by measuring the rate of MeOSuc-Ala-Ala-Pro-Val-AMC degradation.

TNF-α in Traumatic Brain Injury Assay

The present assay provides for examination of the expression of tumor necrosis factor mRNA in specific brain regions which follow experimentally induced lateral fluid percussion traumatic brain injury (TBI) in rats. Adult Sprague-Dawley rats (n=42) were anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury, n=18). Animals are sacrificed by decapitation at 1, 6 and 24 hr. post injury, brains removed, and tissue samples of left (injured) parietal cortex (LC), corresponding area in the contralateral right cortex (RC) are prepared. Total RNA was isolated and Northern blot hybridization is performed and quantitated relative to an TNF-α positive control RNA (macrophage=100%). A marked increase of TNF-α mRNA expression is observed in LH (104±17% of positive control, $p<0.05$ compared with sham), LC (105±21%, $p<0.05$) and LA (69±8%, $p<0.01$ in the traumatized hemisphere 1 hr. following injury. An increased TNF-α mRNA expression is also observed in LH (46±8%, $p<0.05$), LC (30±3%, $p<0.01$) and LS (32±3%, $p<00.01$) at 6 hr. which resolves by 24 hr. following injury. In the contralateral hemisphere, expression of TNF-α mRNA is increased in RH (46±2%, $p<0.01$), RC (4±3%) and RA (22±8%) at 1 hr. and in RH (28±11%), RC (7±5%) and RA (26±6%, $p<0.05$) at 6 hr. following injury. In sham (surgery without injury) or naive animals, no consistent changes in expression of TNF-α mRNA are observed in any of the 6 brain areas in either hemisphere at any times. These results indicate that following parasagittal fluid-percussion brain injury, the temporal expression of TNF-α mRNA is altered in specific brain regions, including those of the non-traumatized hemisphere. Since TNF-α is able to induce nerve growth factor (NGF) and stimulate the release of other cytokines from activated astrocytes, this post-traumatic alteration in gene expression of TNF-α plays an important role in both the acute and regenerative response to CNS trauma.

CNS Injury model for IL-β mRNA

This assay characterizes the regional expression of interleukin-1β(IL-1β) mRNA in specific brain regions following experimental lateral fluid-percussion traumatic brain injury (TBI) in rats. Adult Sprague-Dawley rats (n=42) are anesthetized with sodium pentobarbital (60 mg/kg, i.p.) and subjected to lateral fluid-percussion brain injury of moderate severity (2.4 atm.) centered over the left temporaparietal cortex (n=18), or "sham" treatment (anesthesia and surgery without injury). Animals are sacrificed at 1, 6 and 24 hr. post injury, brains removed, and tissue samples of left (injured) parietal cortex (LC), corresponding area in the contralateral right cortex (RC), cortex adjacent to injured parietal cortex (LA), corresponding adjacent area in the right cortex (RA), left hippocampus (LH) and right hippocampus (RH) are prepared. Total RNA is isolated and Northern blot hybridization was performed and the quantity of brain tissue IL-1β mRNA is presented as percent relative radioactivity of IL-1β positive macrophage RNA which was loaded on same gel. At 1 hr. following brain injury, a marked and significant increase in expression of IL-1β mRNA is observed in LC (20.0±0.7% of positive control, n=6, $p<0.05$ compared with sham animal), LH (24.5±0.9%, $p<0.05$) and LA (21.5±3.1%, $p<0.05$) in the injured hemisphere, which remained elevated up to 6 hr. post injury in the LC (4.0±0.4%, n=6, $p<0.05$) and LH (5.0±1.3%, $p<0.05$). In sham or naive animals, no expression of IL-1β mRNA is observed in any of the respective brain areas. These results indicate that following TBI, the temporal expression of IL-1β mRNA is regionally stimulated in specific brain regions. These regional changes in cytokines, such as IL-1β play a role in the post-traumatic brain injury.

Lipopolysaccharide Mediated Production of Cytokines

Human peripheral blood mononuclear cells (PBMC) are isolated from fresh human blood according to the procedure of Chin and Kostura, *J. Immunol.* 151, 5574–5585 (1993). Whole blood is collected by sterile venipuncture into 60 mL syringes coated with 1.0 mL of sodium heparin (Upjohn, 1000 U/mL) and diluted 1:1 in Hanks Balance Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2\times10^6$ cell/mL in RPM containing 10% fresh autologous human serum, penicillin streptomycin (10 U/mL) and 0.05% DMSO. Lipopolysaccharide (Salmonella type Re545; Sigma Chemicals) is added to the cells to a final concentration of 100 ng/mL). An aliquot (0.1 mL) of the cells is quickly dispensed into each well of a 96 well plate containing 0.1 mL of the test compound, at the appropriate dilution, and are incubated for 24 hours at 37° C. in 5% $CO_2$. At the end of the culture period, cell culture supernatants are assayed for IL-1β, TNF-α, IL-6 and $PGE_2$ production using specific ELISA.

IL-1 Mediated Cytokine Production

Human peripheral blood mononuclear cells are isolated from fresh human blood according to the procedure of Chin and Kostura, *J. Immunol* 151, 5574–5585 (1993). Whole blood is collected by sterile venipuncture into 60 mL syringes coated with 1.0 mL of sodium-heparin (Upjohn, 1000 U/mL) and diluted 1:1 in Hanks Balanced Salt Solution (Gibco). The erythrocytes are separated from the PBMC's by centrifugation on a Ficoll-Hypaque lymphocyte separation media. The PBMC's are washed three times in Hanks Balanced Salt Solution and then resuspended to a final concentration of $2\times10^6$ cell/mL in RPMI containing 10% fresh analogous human serum, penicillin streptomycin (10 U/mL) and 0.05% DMSO. Endotoxin free recombinant human IL-1β is then added to a final concentration of 50 pMolar. An aliquot (0.1 mL) of the cells is quickly dispensed into each well of a 96 well plate containing 0.1 mL of the compound at the appropriate dilution, and are incubated for 24 hours, at 37° C. in 5% $CO_2$. At the end of the culture period, cell culture supernatants are assayed for TNF-α, IL-6 and $PGE_2$ syntheses using specific ELISA.

Determination of IL-1β, TNF-α, IL-6 and Prostanoid Production from LPS or IL-1 Stimulated PBMC's

IL-1β ELISA

Human IL-1β can be detected in cell-culture supernatants or whole blood with the following specific trapping ELISA. Ninety-six well plastic plates (Immulon 4; dynatech) are coated for 12 hours at 4° C. with 1 mg/mL protein-A affinity chromatography purified mouse anti-human IL-1β monoclonal antibody (purchased as an ascites preparation from LAO Enterprise, Gaithersburg, Md.) diluted in Dulbecco's phosphate-buffered saline (—$MgCl_2$, —$CaCl_2$). the plates are washed with PBS-Tween (Kirkegaard and Perry) then blocked with 1% BSA diluent and blocking solution (Kirkegaard and Perry) for 60 minutes at room temperature followed by washing with PBS Tween. IL-1β standards are prepared from purified recombinant IL-1β produced from *E. coli*. The highest concentration begins at 10 ng/mL followed by 11 two-fold serial dilutions. For detection of IL-1β from cell culture supernatants or blood plasma, 10–25 μL of supernatant is added to each test well with 75–90 μL of PBS Tween. Samples are incubated at room temperature for 2 hours then washed 6 times with PBS Tween on an automated plate washer (Dennly). Rabbit anti-human IL-1β polyclonal antisera diluted 1:500 in PBS-Tween is added to the plate and incubated for 1 hour at room temperature followed by six washes with PBS-Tween. Detection of bound rabbit anti-IL-1β IgG is accomplished with Fab fragments of Goat anti-rabbit IgG-horseradish peroxidase conjugate (Accurate Scientific) diluted 1:10,000 in PBS-Tween. Peroxidase activity was determined using TMB peroxidase substrate kit (Kirkegaard and Perry) with quantitation of color density on a 96-well plate Molecular Devices spectrophotometer set to determine absorbance at 450 nM. Samples are evaluated using a standard curve of absorbance versus concentration. Four-parameter logistics analysis generally is used to fit data and obtain concentrations of unknown compounds.

TNF-α ELISA

Immulon 4 (Dynatech) 96-well plastic plates are coated with a 0.5 mg/mL solution of mouse anti-human TNF-α monoclonal antibody. The secondary antibody is a 1:2500 dilution of a rabbit anti-human TNF-α polyclonal serum purchased from Genzyme. All other operations are identical to those described above for IL-1β. The standards are prepared in PBS-Tween+10% FBS or HS. Eleven 2-fold dilutions are made beginning at 20 ng/mL TNF-α.

IL-6 ELISA

Levels of secreted human IL-6 are also determined by specific trapping ELISA as described previously in Chin and Kostura, *J. Immunol.* 151, 5574–5585 (1993). (Dynatech) ELISA plates are coated with mouse anti-human Il-6 monoclonal antibody diluted to 0.5 mg/mL in PBS. The secondary antibody, a rabbit anti-human IL-6 polyclonal antiserum, is diluted 1:5000 with PBS-Tween. All other operations are identical to those described above for IL-1β. The standards are prepared in PBS-Tween+10% FBS or HS. Eleven 2-fold dilutions are made beginning at 50 ng/mL IL-6.

PGE$_2$ Production

Prostaglandin E2 is detected in cell culture supernatants from LPS or IL-1 stimulated PBMC'S using a commercially available enzyme immunoassay. The assay purchased from Cayman Chemical (Catalogue number 514040) and is run according to the manufacturers instructions.

Interleukin 8 (IL-8) HUVEC

Primary human umbilical cord endothelial cells (HUVEC) (Cell Systems, Kirland, Wash.) are maintained in culture medium supplemeuted with 15% fetal bovine serum and 1% CS-HBGF consisting of aFGF and heparin. The cells are then diluted 20-fold before being plated (250 μl) into gelatin coated 96-well plates. Prior to use, culture medium is replaced with fresh medium (200 μl). Buffer or test compound (25 μl, at appropriate concentrations) is then added to each well in quadruplicate wells and the plates incubated for 6 h in a humidified incubator at 37° C. in an atmosphere of 5% $CO_2$. At the end of the incubation period, supernatant is removed and assayed for IL-8 concentration using an IL-8 ELISA kit obtained from R&D Systems (Minneapolis, Minn.). All data is presented as mean value (ng/ml) of multiple samples based on the standard curve. $IC_{50}$ values where appropriate can be generated by non-linear regression analysis.

Interleukin 8 (IL-8) HEK

Human embryonic kidney cells (HEK-293) expressing either CXCR1 or CXCR2 were grown as a monolayer to ~80% confluence in MEM (Sigma cat. #M5650) containing 10% FBS, 1% glutamine and 1% penicillin/streptomycin. Cells were trypsinized and suspended to $2\times10^6$ cells per mL in binding buffer [Hanks Balanced Salts (HBS) containing 25 mM HEPES and 0.05% BSA]. To U-bottom polypropylene 96-well plates containing dried test compounds was added 84 μL of [$^{125}$I] IL8 (Dupont/NEN) in binding buffer followed by 16 μL of cells (32,000 cells/well). The final [$^{125}$I]IL8 concentration was 0.25 nM. Non-specific binding of [$^{125}$I] was measured by adding 5 μL of 25 μM IL8 to control wells without library compounds. The plates were incubated for 1 h at room temperature followed by harvesting using a SKATRON MICRO96 CELL HARVESTER™ onto glass fiber filtermats treated with 0.3% polyethyleneimine and washed three times with PBS. The filtermat was dried in a microwave oven for 1 min., treated with MeltilLex A™ scintillation wax (Wallac Oy, Turku, Finland), and counted on a scintillation counter. $IC_{50}$ values can be generated by non-linear regression analysis.

The compounds shown in the following tables 1 to 8, as well as compounds 501, 502, 601, 602, 603 and 1031–1040 have been synthesized according to the methods described above and have been tested in the biological tests described below. Compounds of the invention exhibit inhibition of IL-8 binding to human embryonic kidney cells with $IC_{50}$'s below 1 mM. Preferred compounds are those with $IC_{50}$'s below 10 μM. (Table 1B). Most preferred compounds are those with $IC_{50}$'s below 500 nM (Table 1A). Other compounds of the invention having $IC_{50}$'s above 10 μM are shown in Table 1C and Charts 1 and 2. All compounds in Tables 4–12 and Charts 1 and 2 exhibit inhibitory activity of Ki≦10 μM in the binding assay described.

TABLE 1A

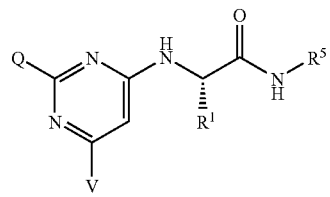

| Ex # | Q | V | $R^1$ | $R^5$ |
|---|---|---|---|---|
| 1 | 1-imidazolyl | —S(CH$_2$)$_7$CH$_3$ | —CH$_2$CH(CH$_3$)$_2$ | —(CH$_2$)$_3$OCH$_3$ |
| 2 | 1-imidazolyl | —S(CH$_2$)$_7$CH$_3$ | —CH$_2$CH(CH$_3$)$_2$ | —(CH$_2$)$_3$OEt |

TABLE 1A-continued

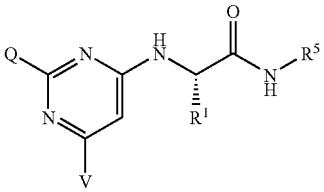

| Ex # | Q | V | R¹ | R⁵ |
|---|---|---|---|---|
| 3 | 1-imidazolyl | —S(CH$_2$)$_7$CH$_3$ | —CH$_2$CH(CH$_3$)$_2$ | —(CH$_2$)$_3$OiPr |
| 4 | 1-imidazolyl | —S(CH$_2$)$_7$CH$_3$ | —CH$_2$CH(CH$_3$)$_2$ | —(CH$_2$)$_3$OBu |
| 7 | 1-imidazolyl | —S(CH$_2$)$_7$CH$_3$ | —CH$_2$CH(CH$_3$)$_2$ | —(CH$_2$)$_3$SCH$_3$ |
| 8 | 1-imidazolyl | —S(CH$_2$)$_7$CH$_3$ | —CH$_2$CH(CH$_3$)$_2$ | —(CH$_2$)$_3$SCH(CH$_3$)$_2$ |
| 11 | 4-methyl-1-imidazolyl | —S(CH$_2$)$_7$CH$_3$ | —CH$_2$CH(CH$_3$)$_2$ | 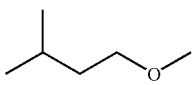 |
| 13 | 4-methyl-1-imidazolyl | —S(CH$_2$)$_7$CH$_3$ | —CH$_2$CH(CH$_3$)$_2$ | 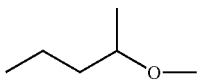 |
| 15 | 1-imidazolyl | —S(CH$_2$)$_7$CH$_3$ | —CH$_2$CH(CH$_3$)$_2$ | 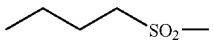 |
| 17 | 4-methyl-1-imidazolyl | —S(CH$_2$)$_8$CH$_3$ | —CH$_2$CH(CH$_3$)$_2$ | —(CH$_2$)$_3$OBu |
| 18 | 4-methyl-1-imidazolyl | 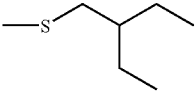 | —CH$_2$CH(CH$_3$)$_2$ | —(CH$_2$)$_3$OBu |
| 25 | 1-imidazolyl | —S(CH$_2$)$_7$CH$_3$, | —(CH$_2$)$_3$CH$_3$ | —(CH$_2$)$_3$OCH$_3$ |
| 26 | 1-imidazolyl | —S(CH$_2$)$_7$CH$_3$ | —(CH$_2$)$_3$CH$_3$ | —(CH$_2$)$_3$OEt |
| 32 | 1-imidazolyl | —S(CH$_2$)$_7$CH$_3$ | —CH$_2$CH(CH$_3$)$_2$ | —(CH$_2$)$_4$CH$_3$ |
| 40 | iPrOC(=O)—N(CH$_3$)— | —S(CH$_2$)$_7$CH$_3$ | —CH$_2$CH(CH$_3$)$_2$ | —(CH$_2$)$_3$OCH$_3$ |
| 60 | CH$_3$C(=O)NH— | —S(CH$_2$)$_7$CH$_3$ | —CH$_2$CH(CH$_3$)$_2$ | —(CH$_2$)$_2$SCH(CH$_3$)$_2$ |
| 66 | phenyl | —S(CH$_2$)$_7$CH$_3$ | —CH$_2$CH(CH$_3$)$_2$ | —(CH$_2$)$_2$SCH(CH$_3$)$_2$ |
| 67 | 3-pyridinyl | —S(CH$_2$)$_7$CH$_3$ | —CH$_2$CH(CH$_3$)$_2$ | —(CH$_2$)$_2$SCH(CH$_3$)$_2$ |
| 68 | 4-pyridinyl | —S(CH$_2$)$_7$CH$_3$ | —CH$_2$CH(CH$_3$)$_2$ | —(CH$_2$)$_3$SCH$_3$ |
| 71 | 5(6)-methyl-1-benzimidazolyl | —S(CH$_2$)$_7$CH$_3$ | S(CH$_2$)$_7$CH$_3$ | —(CH$_2$)$_3$OEt |
| 77 | 4-methyl-1-imidazolyl | —S(CH$_2$)$_7$CH$_3$ | —CH$_2$CH(CH$_3$)$_2$ | —(CH$_2$)$_3$OCH$_3$ |
| 82 | CH$_3$CH(OH)— | —S(CH$_2$)$_7$CH$_3$ | —CH$_2$CH(CH$_3$)$_2$ | —(CH$_2$)$_3$OEt |
| 89 | 4-methyl-imidazolyl | —S(CH$_2$)$_7$CH$_3$ | —CH$_2$CH(CH$_3$)$_2$ | —(CH$_2$)$_3$OEt |
| 94 | 1-imidazolyl | 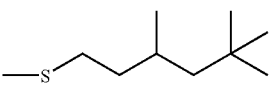 | —CH$_2$CH(CH$_3$)$_2$ | —(CH$_2$)$_3$OEt |
| 95 | 1-imidazolyl | 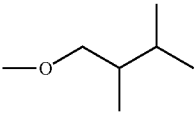 | —CH$_2$CH(CH$_3$)$_2$ | —(CH$_2$)$_3$OEt |
| 96 | 1-imidazolyl | 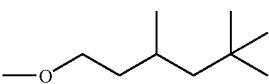 | —CH$_2$CH(CH$_3$)$_2$ | —(CH$_2$)$_3$OEt |
| 98 | 1-imidazolyl | 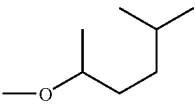 | —CH$_2$CH(CH$_3$)$_2$ | —(CH$_2$)$_3$OEt |

TABLE 1A-continued

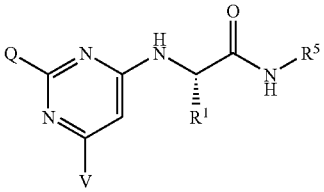

| Ex # | Q | V | R¹ | R⁵ |
|---|---|---|---|---|
| 103 | 1-benzimidazolyl |  | —CH₂CH(CH₃)₂ | —(CH₂)₃OCH₃ |
| 105 | 4-methyl-1-imidazolyl | 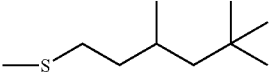 | —(CH₂)₃CH₃ | —(CH₂)₃OEt |
| 106 | 4-methyl-1-imidazolyl | 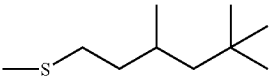 | —CH₂CH(CH₃)₂ | —(CH₂)₃OEt |
| 108 | 1-benzimidazolyl | 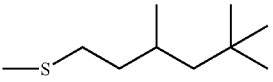 | —CH₂CH(CH₃)₂ | —(CH₂)₃OCH₃ |
| 110 | 1-benzimidazolyl | —S(CH₂)₅COOEt | —CH₂CH(CH₃)₂ | —(CH₂)₃OCH₃ |
| 111 | 1-benzimidazolyl | —S(CH₂)₄OPh | —CH₂CH(CH₃)₂ | —(CH₂)₃OEt |
| 112 | 1-imidazolyl | 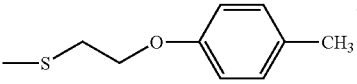 | —CH₂CH(CH₃)₂ | —(CH₂)₃SCH₃ |
| 117 | 4-methyl-1-imidazolyl | —S(CH₂)₇CH₃ | —CH₂CH(CH₃)₂ | —(CH₂)₃OCH₃ |
| 123 | 3-pyridinyl | —O(CH₂)₇CH₃ | —CH₂CH(CH₃)₂ | —(CH₂)₃OCH₃ |
| 126 | 3-pyridinyl | —S(CH₂)₇CH₃ | —CH₂CH(CH₃)₂ | —(CH₂)₃OCH₃ |
| 131 | 1-imidazolyl | —S(CH₂)₅CH₃ | —CH₂CH(CH₃)₂ | —(CH₂)₃SCH₃ |
| 133 | 1-imidazolyl | —O(CH₂)₅CH₃ | —CH₂CH(CH₃)₂ | —(CH₂)₂SCH(CH₃)₂ |
| 134 | 1-imidazolyl | —S(CH₂)₄CH₃ | —CH₂CH(CH₃)₂ | —(CH₂)₃SCH₃ |
| 135 | 1-imidazolyl | —(CH₂)₅CH₃ | —CH₂CH(CH₃)₂ | —(CH₂)₃SCH₃ |
| 145 | 1-imidazolyl | 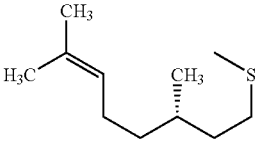 | —CH₂CH(CH₃)₂ | —(CH₂)₃OCH₃ |
| 146 | 1-imidazolyl | —S-farnesyl | —CH₂CH(CH₃)₂ | —(CH₂)₃OCH₃ |
| 147 | 4-methyl-1-imidazolyl | 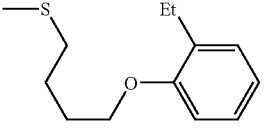 | —CH₂CH(CH₃)₂ | —(CH₂)₃OEt |
| 149 | 4-methyl-1-imidazolyl | 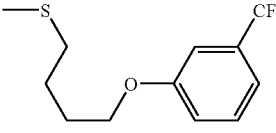 | —CH₂CH(CH₃)₂ | —(CH₂)₃OEt |
| 150 | 4-methyl-1-imidazolyl | —S(CH₂)₄S—Ph | —CH₂CH(CH₃)₂ | —(CH₂)₃OEt |

TABLE 1A-continued

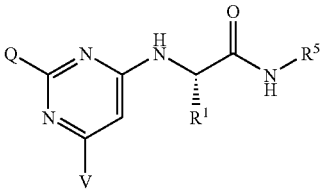

| Ex # | Q | V | R¹ | R⁵ |
|---|---|---|---|---|
| 151 | 4-methyl-1-imidazolyl | 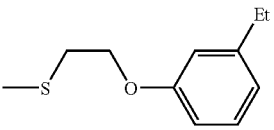 | —CH₂CH(CH₃)₂ | —(CH₂)₃OEt |
| 152 | 4-methyl-1-imidazolyl | 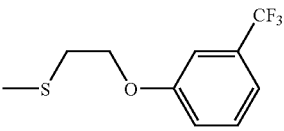 | —CH₂CH(CH₃)₂ | —(CH₂)₃OEt |
| 154 | 4-methyl-1-imidazolyl | 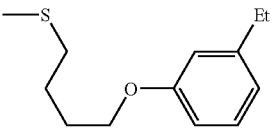 | —CH₂CH(CH₃)₂ | —(CH₂)₃OEt |
| 157 | 4-methyl-1-imidazolyl | 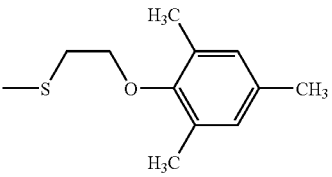 | —CH₂CH(CH₃)₂ | —(CH₂)₃OEt |
| 158 | 1-benzimidazolyl | —S(CH₂)₂OPh | —CH₂CH(CH₃)₂ | —(CH₂)₃OCH₃ |
| 160 | 4-methyl-1-imidazolyl | 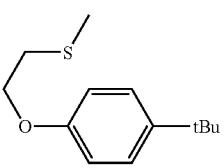 | —CH₂CH(CH₃)₂ | —(CH₂)₃OEt |
| 161 | 1-benzimidazolyl | —S(CH₂)₄OPh | —CH₂CH(CH₃)₂ | —(CH₂)₃OCH₃ |
| 308 | 1-imidazolyl | n-hexyl | —CH₂CH(CH₃)₂ | 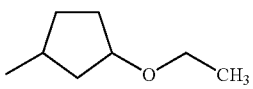 |
| 309 | 1-imidazolyl | —(CH₂)₂Ph | —CH₂CH(CH₃)₂ | 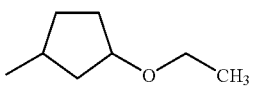 |
| 310 | 1-imidazolyl | n-butyl | —CH₂CH(CH₃)₂ | 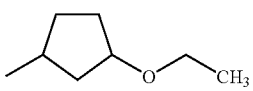 |
| 311 | 1-imidazolyl | —(CH₂)₂-pyridin-2-yl | —CH₂CH(CH₃)₂ | —(CH₂)₃OEt |
| 312 | 1-imidazolyl | —(CH₂)₂Ph | —CH₂CH(CH₃)₂ | —(CH₂)₃OEt |
| 314 | 1-imidazolyl | —(CH₂)₂Ph | 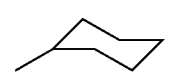 | —(CH₂)₃OEt |

TABLE 1A-continued

| Ex # | Q | V | R¹ | R⁵ |
|---|---|---|---|---|
| 315 | 1-imidazolyl | —(CH$_2$)$_2$Ph | —(CH$_2$)$_2$—CH(CH$_3$)$_2$ | —(CH$_2$)$_3$OEt |
| 316 | 1-imidazolyl | —(CH$_2$)$_2$-cyclohexyl | —CH$_2$CH(CH$_3$)$_2$ | —(CH$_2$)$_3$OEt |
| 318 | 1-imidazolyl | —(CH$_2$)$_2$-cyclohexyl | cyclohexyl | —(CH$_2$)$_3$OEt |
| 319 | 1-imidazolyl | —(CH$_2$)$_2$-cyclohexyl | —(CH$_2$)$_2$—CH(CH$_3$)$_2$ | —(CH$_2$)$_3$OEt |
| 320 | 1-imidazolyl | —O-nPr | —CH$_2$CH(CH$_3$)$_2$ | —(CH$_2$)$_3$OEt |
| 321 | 1-imidazolyl | t-butyl | —CH$_2$CH(CH$_3$)$_2$ | —(CH$_2$)$_3$OEt |
| 322 | 1-imidazolyl | 3-methoxyphenylpropyl | —CH$_2$CH(CH$_3$)$_2$ | —(CH$_2$)$_3$OEt |
| 323 | 1-imidazolyl | n-hexyl | —CH$_2$CH(CH$_3$)$_2$ | —CH$_2$CH=CHCH$_2$OEt |
| 324 | 1-imidazolyl | n-hexyl | —CH$_2$CH(CH$_3$)$_2$ | —(CH$_2$)$_4$OEt |
| 325 | 1-imidazolyl | n-hexyl | —CH$_2$CH(CH$_3$)$_2$ | —(CH$_2$)$_3$OH |
| 326 | 1-imidazolyl | n-butyl | —CH$_2$CH(CH$_3$)$_2$ | —(CH$_2$)$_3$OEt |
| 327 | 1-imidazolyl | n-octyl | —CH$_2$CH(CH$_3$)$_2$ | —(CH$_2$)$_3$OEt |
| 328 | 1-imidazolyl | n-octyl | —CH$_2$CH(CH$_3$)$_2$ | —(CH$_2$)$_3$OEt |
| 330 | 1-imidazolyl | n-octyl | —CH$_2$CH(CH$_3$)$_2$ | —(CH$_2$)$_3$OEt |
| 331 | 1-imidazolyl | 4-chlorophenylpropyl | —CH$_2$CH(CH$_3$)$_2$ | —(CH$_2$)$_3$OEt |
| 333 | 1-imidazolyl | n-butyl | cyclopropyl | —(CH$_2$)$_3$OEt |
| 334 | 3-pyridinyl | n-butyl | —CH$_2$CH(CH$_3$)$_2$ | —(CH$_2$)$_3$OEt |
| 335 | 4-trifluoromethyl-1-imidazolyl | n-butyl | —CH$_2$CH(CH$_3$)$_2$ | —(CH$_2$)$_3$OEt |
| 336 | 3-fluorophenyl | n-butyl | —CH$_2$CH(CH$_3$)$_2$ | —(CH$_2$)$_3$OEt |
| 337 | 2-methyl-1-imidazolyl | n-butyl | —CH$_2$CH(CH$_3$)$_2$ | —(CH$_2$)$_3$OEt |
| 338 | 1-imidazolyl | —(CH$_2$)$_2$Ph | cyclopropyl | —(CH$_2$)$_3$OEt |
| 339 | 1-imidazolyl | n-hexyl | cyclohexyl | —(CH$_2$)$_3$OEt |
| 340 | 1-imidazolyl | n-hexyl | cyclohexyl | —(CH$_2$)$_3$OEt |
| 341 | 1-imidazolyl | n-butyl | —(CH$_2$)$_2$—CH(CH$_3$)$_2$ | —(CH$_2$)$_3$OEt |
| 342 | 1-imidazolyl | n-butyl | cyclohexyl | —(CH$_2$)$_3$OEt |
| 343 | 1-imidazolyl | n-butyl | cyclohexyl | —(CH$_2$)$_3$OEt |

TABLE 1A-continued

| Ex # | Q | V | R¹ | R⁵ |
|---|---|---|---|---|
| 344 | 4-pyridinyl | n-butyl | —CH₂CH(CH₃)₂ | —(CH₂)₃OEt |
| 345 | 1-imidazolyl | n-hexyl | —CH₂CH(CH₃)₂ | —(CH₂)₃OEt |
| 346 | 1-imidazolyl | 4-methylphenylpropyl | —CH₂CH(CH₃)₂ | —(CH₂)₃OEt |
| 347 | 1-imidazolyl | 4-fluorophenylpropyl | —CH₂CH(CH₃)₂ | —(CH₂)₃OEt |
| 349 | 4-methyl-1-imidazolyl | n-butyl | —CH₂CH(CH₃)₂ | —(CH₂)₃OEt |
| 350 | 1-imidazolyl | n-hexyl | —CH₂CH(CH₃)₂ | —(CH₂)₃OEt |
| 351 | 1-imidazolyl | n-hexyl | —(CH₂)₂—CH(CH₃)₂ | —(CH₂)₃OEt |

TABLE 1B

| Ex # | Q | V | R¹ | R⁵ |
|---|---|---|---|---|
| 5 | 1-imidazolyl | —S(CH₂)₇CH₃ | —CH₂CH(CH₃)₂ | —(CH₂)₃CH₃ |
| 6 | 1-imidazolyl | —S(CH₂)₇CH₃ | —CH₂CH(CH₃)₂ | —(CH₂)₃Phenyl |
| 12 | 4-methyl-1-imidazolyl | —S(CH₂)₇CH₃ | —CH₂CH(CH₃)₂ | 2-methylbutyl methyl ether |
| 14 | 1-imidazolyl | —S(CH₂)₇CH₃ | —CH₂CH(CH₃)₂ | 3-morpholinopropyl |
| 16 | 1-benzimidazolyl | —S(CH₂)₆CH₃ | —CH₂CH(CH₃)₂ | —CH₂CH₂OEt |
| 21 | 4-methyl-1-imidazolyl | —S(CH₂)₈CH₃ | —CH₂CH(CH₃)₂ | 4-methoxybenzyl |
| 28 | 1-imidazolyl | —S(CH₂)₇CH₃ | —CH₂SCH₃ | —(CH₂)₄CH₃ |
| 29 | 1-imidazolyl | —S(CH₂)₇CH₃ | —C(CH₃)₃ | —(CH₂)₄CH₃ |
| 30 | 1-imidazolyl | —S(CH₂)₇CH₃ | —CH₂CH₃ | —(CH₂)₃OCH₃ |
| 31 | 1-imidazolyl | —S(CH₂)₇CH₃ | —CH(CH₃)₂ | —(CH₂)₃CH₃ |
| 35 | iPrOC(=O)NH— | —S(CH₂)₇CH₃ | —CH₂CH(CH₃)₂ | —(CH₂)₃OCH₃ |

TABLE 1B-continued

| Ex # | Q | V | R¹ | R⁵ |
|---|---|---|---|---|
| 38 | CH₃O-CH₂CH₂-O-C(=O)-NH— | —S(CH₂)₇CH₃ | —CH₂CH(CH₃)₂ | —(CH₂)₃OCH₃ |
| 42 | CH₃O-CH₂CH₂-O-C(=O)-NH— | —S(CH₂)₇CH₃ | —CH₂CH(CH₃)₂ | —(CH₂)₃OCH₃ |
| 43 | CH₃O-CH₂CH₂-O-C(=O)-NH— | —S(CH₂)₇CH₃ | —CH₂CH(CH₃)₂ | —(CH₂)₃OCH₃ |
| 44 | Cyclohexyl-C(=O)-NH— | —S(CH₂)₇CH₃ | —CH₂CH(CH₃)₂ | —(CH₂)₃OCH₃ |
| 45 | iBuC(=O)NH— | —S(CH₂)₇CH₃ | —CH₂CH(CH₃)₂ | —(CH₂)₃OCH₃ |
| 46 | MeOCH₂C(=O)NH— | —S(CH₂)₇CH₃ | —CH₂CH(CH₃)₂ | —(CH₂)₃OCH₃ |
| 48 | Cyclohexyl-NH-C(=O)-NH— | —S(CH₂)₇CH₃ | —CH₂CH(CH₃)₂ | —(CH₂)₃OCH₃ |
| 49 | Cyclopropyl-C(=O)-N(CH₃)— | —S(CH₂)₇CH₃ | —CH₂CH(CH₃)₂ | —(CH₂)₃OCH₃ |
| 50 | Cyclohexyl-C(=O)-N(CH₃)— | —S(CH₂)₇CH₃ | —CH₂CH(CH₃)₂ | —(CH₂)₃OCH₃ |
| 51 | iBuC(=O)N(CH₃)— | —S(CH₂)₇CH₃ | —CH₂CH(CH₃)₂ | —(CH₂)₃OCH₃ |
| 52 | CH₃O-CH₂-C(=O)-N(CH₃)— | —S(CH₂)₇CH₃ | —CH₂CH(CH₃)₂ | —(CH₂)₃OCH₃ |
| 53 | CH₃S-(CH₂)₃-C(=O)-N(CH₃)— | —S(CH₂)₇CH₃ | —CH₂CH(CH₃)₂ | —(CH₂)₃OCH₃ |

TABLE 1B-continued

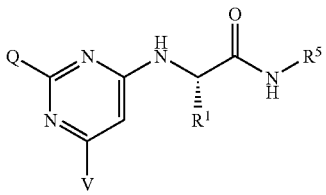

| Ex # | Q | V | R¹ | R⁵ |
|---|---|---|---|---|
| 54 | 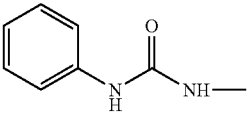 | —S(CH$_2$)$_7$CH$_3$ | —CH$_2$CH(CH$_3$)$_2$ | —(CH$_2$)$_3$OCH$_3$ |
| 55 | 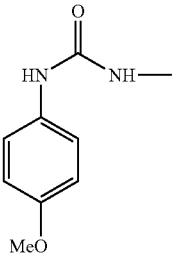 | —S(CH$_2$)$_7$CH$_3$ | —CH$_2$CH(CH$_3$)$_2$ | —(CH$_2$)$_3$OCH$_3$ |
| 56 | 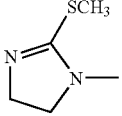 | —S(CH$_2$)$_7$CH$_3$ | —CH$_2$CH(CH$_3$)$_2$ | —(CH$_2$)$_2$SCH(CH$_3$)$_2$ |
| 57 | 1-benzimidazolyl | —S(CH$_2$)$_7$CH$_3$ | —CH$_2$CH(CH$_3$)$_2$ | —(CH$_2$)$_2$SCH(CH$_3$)$_2$ |
| 58 | 1-pyrrolyl | —S(CH$_2$)$_7$CH$_3$ | —CH$_2$CH(CH$_3$)$_2$ | —(CH$_2$)$_2$SCH(CH$_3$)$_2$ |
| 61 | 4-morpholinyl | —S(CH$_2$)$_7$CH$_3$ | —CH$_2$CH(CH$_3$)$_2$ | —(CH$_2$)$_3$OCH$_3$ |
| 62 | 4-(Boc)-piperazin-1-yl | —S(CH$_2$)$_7$CH$_3$ | —CH$_2$CH(CH$_3$)$_2$ | —(CH$_2$)$_3$OCH$_3$ |
| 63 | 1-piperazinyl TFA salt | —S(CH$_2$)$_7$CH$_3$ | —CH$_2$CH(CH$_3$)$_2$ | —(CH$_2$)$_3$OCH$_3$ |
| 69 | 2-pyridinyl | —S(CH$_2$)$_7$CH$_3$ | —CH$_2$CH(CH$_3$)$_2$ | —(CH$_2$)$_2$SCH(CH$_3$)$_2$ |
| 73 | 1-pyrrolyl | —Cl | —CH$_2$CH(CH$_3$)$_2$ | —(CH$_2$)$_3$OCH$_3$ |
| 75 | 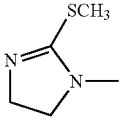 | —F | —CH$_2$CH(CH$_3$)$_2$ | —(CH$_2$)$_3$SCH$_3$ |
| 78 | 4-(hydroxymethyl)-1-imidazolyl | —S(CH$_2$)$_7$CH$_3$ | —CH$_2$CH(CH$_3$)$_2$ | —(CH$_2$)$_3$OCH$_3$ |
| 80 | 4-(phenoxymethyl)-1-imidazolyl | —S(CH$_2$)$_7$CH$_3$ | —CH$_2$CH(CH$_3$)$_2$ | —(CH$_2$)$_3$OCH$_3$ |
| 81 | HOCH$_2$— | —S(CH$_2$)$_7$CH$_3$ | —CH$_2$CH(CH$_3$)$_2$ | —(CH$_2$)$_3$OEt |
| 83 | HOOC— | —S(CH$_2$)$_7$CH$_3$ | —CH$_2$CH(CH$_3$)$_2$ | —(CH$_2$)$_3$OEt |
| 84 | CH$_3$OOC— | —S(CH$_2$)$_7$CH$_3$ | —CH$_2$CH(CH$_3$)$_2$ | —(CH$_2$)$_3$OEt |
| 85 | 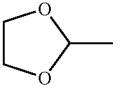 | —S(CH$_2$)$_7$CH$_3$ | —CH$_2$CH(CH$_3$)$_2$ | —(CH$_2$)$_3$OEt |
| 86 | CH$_3$C(=O)— | —S(CH$_2$)$_7$CH$_3$ | —CH$_2$CH(CH$_3$)$_2$ | —(CH$_2$)$_3$OEt |
| 87 | HOOCCH$_2$— | —S(CH$_2$)$_7$CH$_3$ | —CH$_2$CH(CH$_3$)$_2$ | —(CH$_2$)$_3$OEt |
| 88 | CH$_3$OOCCH$_2$— | —S(CH$_2$)$_7$CH$_3$ | —CH$_2$CH(CH$_3$)$_2$ | —(CH$_2$)$_3$OEt |
| 90 | 1-imidazolyl | —S(CH$_2$)$_3$CF$_3$ | —CH$_2$CH(CH$_3$)$_2$ | —(CH$_2$)$_3$OEt |

TABLE 1B-continued

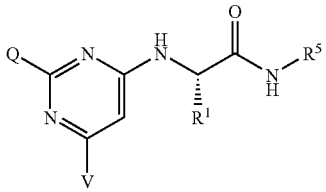

| Ex # | Q | V | R$^1$ | R$^5$ |
|---|---|---|---|---|
| 91 | 1-imidazolyl | 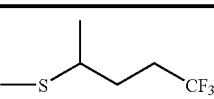 | —CH$_2$CH(CH$_3$)$_2$ | —(CH$_2$)$_3$OEt |
| 92 | 4-methyl-1-imidazolyl | —S-tBu | —CH$_2$CH(CH$_3$)$_2$ | —(CH$_2$)$_3$OEt |
| 93 | 4-methyl-1-imidazolyl | —SCH$_3$ | —CH$_2$CH(CH$_3$)$_2$ | —(CH$_2$)$_3$OEt |
| 97 | 1-imidazolyl | 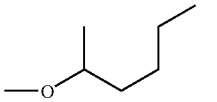 | —CH$_2$CH(CH$_3$)$_2$ | —(CH$_2$)$_3$OEt |
| 99 | 4-methyl-1-imidazolyl | 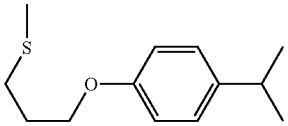 | —CH$_2$CH(CH$_3$)$_2$ | —(CH$_2$)$_3$OEt |
| 100 | 1-imidazolyl | —S(CH$_2$)$_{10}$OH | —CH$_2$CH(CH$_3$)$_2$ | —(CH$_2$)$_3$OCH$_3$ |
| 101 | 1-imidazolyl | 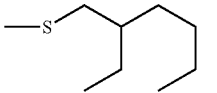 | —CH$_2$CH(CH$_3$)$_2$ | —(CH$_2$)$_3$OCH$_3$ |
| 102 | 1-benzimidazolyl | 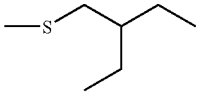 | —CH$_2$CH(CH$_3$)$_2$ | —(CH$_2$)$_3$OCH$_3$ |
| 104 | 4-phenyl-1-imidazolyl | —S(CH$_2$)$_5$CN | —CH$_2$CH(CH$_3$)$_2$ | —(CH$_2$)$_3$OEt |
| 107 | 1-benzimidazolyl | 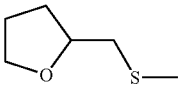 | —CH$_2$CH(CH$_3$)$_2$ | —(CH$_2$)$_3$OCH$_3$ |
| 113 | 4-methyl-1-imidazolyl | 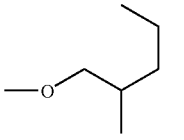 | —CH$_2$CH(CH$_3$)$_2$ | —(CH$_2$)$_3$OCH$_3$ |
| 114 | 4-methyl-1-imidazolyl | 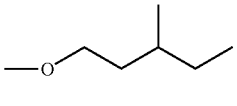 | —CH$_2$CH(CH$_3$)$_2$ | —(CH$_2$)$_3$OCH$_3$ |
| 120 | 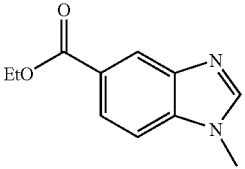 | —S(CH$_2$)$_7$CH$_3$ | —CH$_2$CH(CH$_3$)$_2$ | —(CH$_2$)$_3$OCH$_3$ |

TABLE 1B-continued

| Ex # | Q | V | R¹ | R⁵ |
|---|---|---|---|---|
| 124 |  | —O(CH$_2$)$_7$CH$_3$ | —CH$_2$CH(CH$_3$)$_2$ | —(CH$_2$)$_3$OEt |
| 125 | 5-methoxy methyl-3-pyridinyl | —S(CH$_2$)$_7$CH$_3$ | —CH$_2$CH(CH$_3$)$_2$ | —(CH$_2$)$_3$OCH$_3$ |
| 127 | 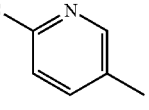 | —S(CH$_2$)$_7$CH$_3$ | —CH$_2$CH(CH$_3$)$_2$ | —(CH$_2$)$_3$OCH$_3$ |
| 128 | 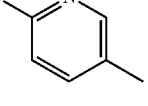 | —S(CH$_2$)$_7$CH$_3$ | —CH$_2$CH(CH$_3$)$_2$ | —(CH$_2$)$_3$OCH$_3$ |
| 129 | 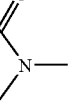 | —S(CH$_2$)$_7$CH$_3$ | —CH$_2$CH(CH$_3$)$_2$ | —(CH$_2$)$_3$OCH$_3$ |
| 130 | 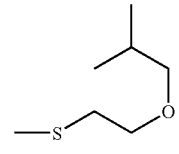 | —S(CH$_2$)$_7$CH$_3$ | —CH$_2$CH(CH$_3$)$_2$ | —(CH$_2$)$_3$OCH$_3$ |
| 139 | 1-benzimidazolyl | 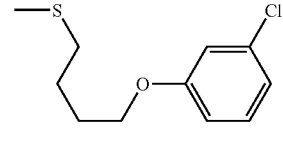 | —CH$_2$CH(CH$_3$)$_2$ | —(CH$_2$)$_3$OCH$_3$ |
| 141 | 1-imidazolyl | —S(CH$_2$)$_9$OH | —CH$_2$CH(CH$_3$)$_2$ | —(CH$_2$)$_3$OCH$_3$ |
| 148 | 4-methyl-1-imidazolyl | 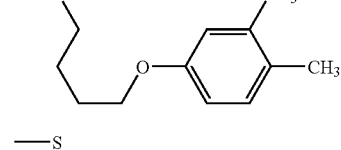 | —CH$_2$CH(CH$_3$)$_2$ | —(CH$_2$)$_3$OEt |
| 153 | 4-methyl-1-imidazolyl | 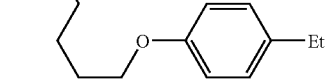 | —CH$_2$CH(CH$_3$)$_2$ | —(CH$_2$)$_3$OEt |
| 155 | 4-methyl-1-imidazolyl |  | —CH$_2$CH(CH$_3$)$_2$ | —(CH$_2$)$_3$OEt |

TABLE 1B-continued

| Ex # | Q | V | R¹ | R⁵ |
|---|---|---|---|---|
| 156 | 4-methyl-1-imidazolyl | —S—CH₂-cyclopropyl-CH₂OPh | —CH₂CH(CH₃)₂ | —(CH₂)₃OEt |
| 159 | 1-imidazolyl | —S(CH₂)₂O-(2-chloropyridin-3-yl) | —CH₂CH(CH₃)₂ | —(CH₂)₃SCH₃ |
| 313 | 1-imidazolyl | —(CH₂)₂Ph | cyclohexylmethyl | —(CH₂)₃OEt |
| 317 | 1-imidazolyl | —(CH₂)₂-cyclohexyl | cyclohexylmethyl | —(CH₂)₃OEt |
| 329 | 1-imidazolyl | n-octyl | cyclohexylmethyl | —(CH₂)₃OEt |
| 332 | 1-imidazolyl | —(CH₂)₃-(3,4-dichlorophenyl) | —CH₂CH(CH₃)₂ | —(CH₂)₃OEt |
| 348 | 1-imidazolyl | —(CH₂)₃-(3,4-difluorophenyl) | —CH₂CH(CH₃)₂ | —(CH₂)₃OEt |

TABLE 1C

| Ex # | Q | V | R¹ | R⁵ |
|---|---|---|---|---|
| 9 | 4-methyl-1-imidazolyl | —S(CH₂)₇CH₃ | —CH₂CH(CH₃)₂ | 1-ethyl-1-(methoxymethyl)cyclopropyl |
| 10 | 4-methyl-1-imidazolyl | —S(CH₂)₂C(CH₃)₃ | —CH₂CH(CH₃)₂ | 1-ethyl-1-(methoxymethyl)cyclopropyl |

TABLE 1C-continued

| Ex # | Q | V | R¹ | R⁵ |
|---|---|---|---|---|
| 19 | 4-methyl-1-imidazolyl | —S(CH₂)₈CH₃ | —CH₂CH(CH₃)₂ | 3-methoxyphenyl-methyl |
| 20 | 4-methyl-1-imidazolyl | —S-CH₂CH(Et)Et | —CH₂CH(CH₃)₂ | 3-methoxyphenyl-methyl |
| 22 | 4-methyl-1-imidazolyl | —S-CH₂CH(Et)Et | —CH₂CH(CH₃)₂ | 4-methoxyphenyl-methyl |
| 23 | 1-imidazolyl | —S(CH₂)₇CH₃ | —(CH₂)₂CH₃ | —(CH₂)₃OCH₃ |
| 24 | 1-imidazolyl | —S(CH₂)₇CH₃ | —(CH₂)₂CH₃ | —(CH₂)₃OEt |
| 27 | 1-imidazolyl | —S(CH₂)₇CH₃ | —CH₂CH₃ | —(CH₂)₃OEt |
| 33 | 1-imidazolyl | —S(CH₂)₇CH₃ | —CH(CH₃)CH₂CH₃ | —(CH₂)₄CH₃ |
| 34 | MeOC(=O)NH— | —S(CH₂)₇CH₃ | —CH₂CH(CH₃)₂ | —(CH₂)₃OCH₃ |
| 36 | BnOC(=O)NH— | —S(CH₂)₇CH₃ | —CH₂CH(CH₃)₂ | —(CH₂)₃OCH₃ |
| 37 | PhOC(=O)NH— | —S(CH₂)₇CH₃ | —CH₂CH(CH₃)₂ | —(CH₂)₃OCH₃ |
| 39 | CH₃OC(=O)—N(CH₃)— | —S(CH₂)₇CH₃ | —CH₂CH(CH₃)₂ | —(CH₂)₃OCH₃ |
| 41 | BnOC(=O)—N(CH₃)— | —S(CH₂)₇CH₃ | —CH₂CH(CH₃)₂ | —(CH₂)₃OCH₃ |
| 47 | EtNHC(=O)NH— | —S(CH₂)₇CH₃ | —CH₂CH(CH₃)₂ | —(CH₂)₃OCH₃ |
| 59 | Ph-C(=NH)-N(H)(Me) | —S(CH₂)₇CH₃ | —CH₂CH(CH₃)₂ | —(CH₂)₂SCH(CH₃)₂ |
| 64 | 4-(acetyl)-piperazin-1-yl | —S(CH₂)₇CH₃ | —CH₂CH(CH₃)₂ | —(CH₂)₃OCH₃ |
| 65 | 3-quinolinyl | —S(CH₂)₇CH₃ | —CH₂CH(CH₃)₂ | —(CH₂)₂SCH(CH₃)₂ |
| 70 | 3-furanyl | —S(CH₂)₇CH₃ | —CH₂CH(CH₃)₂ | —(CH₂)₃OCH₃ |
| 72 | Ph-C(=NH)-N(H)(Me) | —S(CH₂)₁₁CH₃ | —CH₂CH(CH₃)₂ | —(CH₂)₂SCH(CH₃)₂ |
| 74 | Ph-C(=NH)-N(H)(Me) | —F | —CH₂CH(CH₃)₂ | —(CH₂)₃SCH₃ |
| 79 | CH₃OCH₂OCH₂-(1-methylimidazol-4-yl) | —S(CH₂)₇CH₃ | —CH₂CH(CH₃)₂ | —(CH₂)₃OCH₃ |
| 109 | 1-benzimidazolyl | —S(CH₂)₅COOH | —CH₂CH(CH₃)₂ | —(CH₂)₃OCH₃ |

TABLE 1C-continued

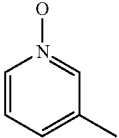

| Ex # | Q | V | R[1] | R[5] |
|------|---|---|------|------|
| 115 | 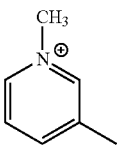 | —O(CH$_2$)$_7$CH$_3$ | —CH$_2$CH(CH$_3$)$_2$ | —(CH$_2$)$_3$OCH$_3$ |
| 116 | 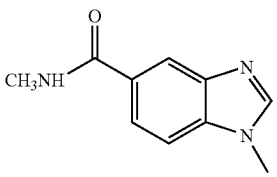 | —O(CH$_2$)$_7$CH$_3$ | —CH$_2$CH(CH$_3$)$_2$ | —(CH$_2$)$_3$OCH$_3$ |
| 118 | 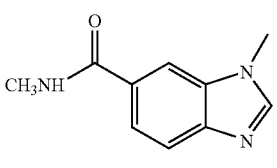 | —S(CH$_2$)$_7$CH$_3$ | —CH$_2$CH(CH$_3$)$_2$ | —(CH$_2$)$_3$OCH$_3$ |
| 119 | 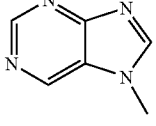 | —S(CH$_2$)$_7$CH$_3$ | —CH$_2$CH(CH$_3$)$_2$ | —(CH$_2$)$_3$OCH$_3$ |
| 121 |  | —S(CH$_2$)$_7$CH$_3$ | —CH$_2$CH(CH$_3$)$_2$ | —(CH$_2$)$_3$OCH$_3$ |
| 122 | 5-pyrimidinyl | —S(CH$_2$)$_7$CH$_3$ | 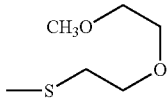 | —(CH$_2$)$_3$OCH$_3$ |
| 132 | 1-imidazolyl | —NH(CH$_2$)$_7$CH$_3$ | —CH$_2$CH(CH$_3$)$_2$ | —(CH$_2$)$_3$SCH$_3$ |
| 137 | 1-imidazolyl | Phenyl | —CH$_2$CH(CH$_3$)$_2$ | —(CH$_2$)$_3$SCH$_3$ |
| 138 | 4-methyl-1-imidazolyl | 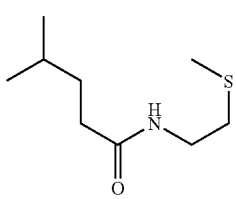 | —(CH$_2$)$_3$CH$_3$ | —(CH$_2$)$_3$OEt |
| 140 | 1-imidazolyl |  | —CH$_2$CH(CH$_3$)$_2$ | —(CH$_2$)$_3$OCH$_3$ |
| 142 | 1-imidazolyl | —CH(COOEt)$_2$ | —CH$_2$CH(CH$_3$)$_2$ | —(CH$_2$)$_3$OCH$_3$ |

TABLE 1C-continued

| Ex # | Q | V | R¹ | R⁵ |
|---|---|---|---|---|
| 143 | 4-phenyl-1-imidazolyl | —CH₃ | —CH₂CH(CH₃)₂ | —(CH₂)₃SCH₃ |
| 144 | 1-imidazolyl | (CH₃)₂C=CHCH₂CH₂C(CH₃)=CHCH₂SCH₃ (geranyl-type thioether) | —CH₂CH(CH₃)₂ | —(CH₂)₃OCH₃ |

TABLE 2

| Ex # | V | (ring) |
|---|---|---|
| 201 | —S—CH₂CH(C₂H₅)₂ | 1-piperidinyl |
| 202 | —S(CH₂)₇CH₃ | 4-morpholinyl |
| 203 | —S(CH₂)₄OPh | 4-morpholinyl |
| 204 | —S(CH₂)₇CH₃ | 1-piperidinyl |
| 205 | —S—CH₂CH₂CH(CH₃)CH₂C(CH₃)₃ | 1-pyrrolidinyl |
| 206 | —S(CH₂)₇CH₃ | 1-pyrrolidinyl |

TABLE 2A

| Entry | Structure |
|---|---|
| 308 | [Structure: 2-(1-imidazolyl)-6-hexyl-pyrimidin-4-yl linked via NH to (S)-leucine amide with N-(3-ethoxycyclopentyl)] |

TABLE 2A-continued
| Entry | Structure |
|---|---|
| 309 | 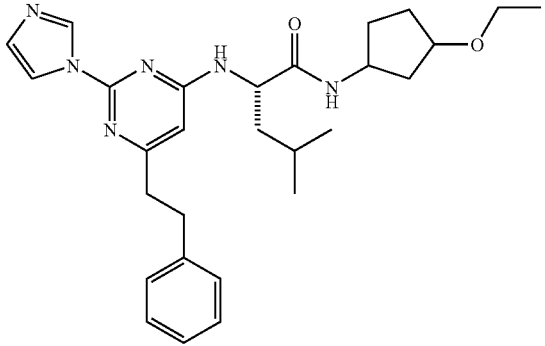 |
| 310 | 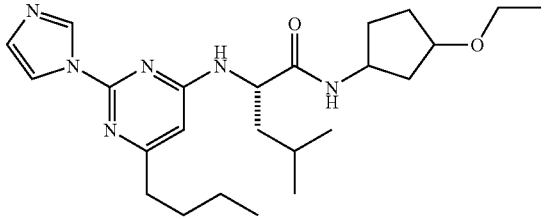 |
| 311 | 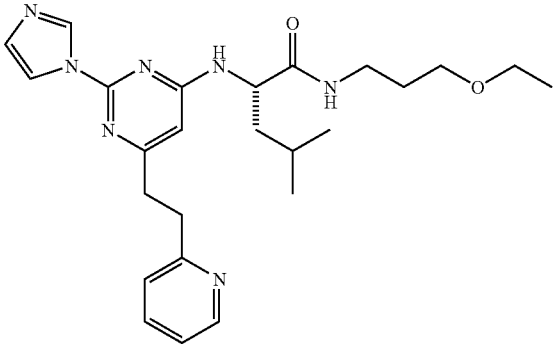 |
| 312 | 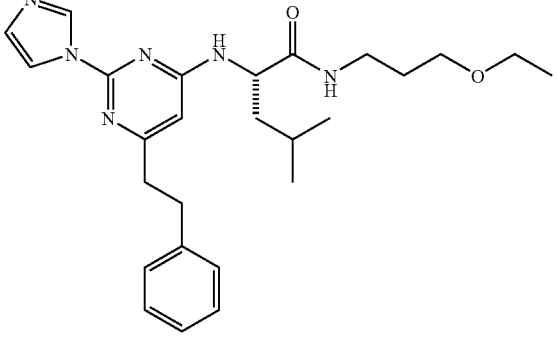 |

TABLE 2A-continued

| Entry | Structure |
|---|---|
| 313 | 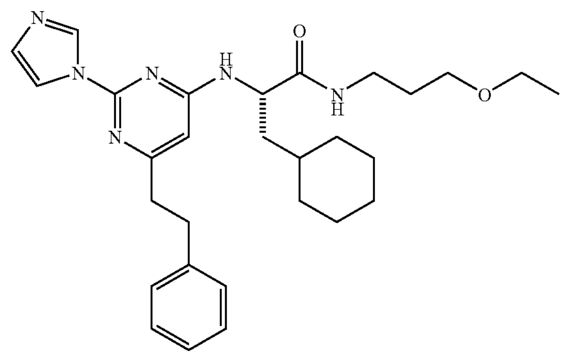 |
| 314 | 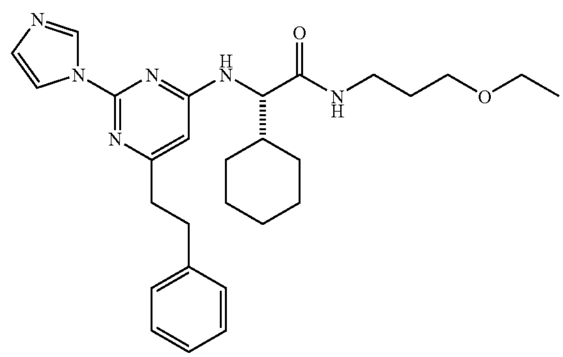 |
| 315 | 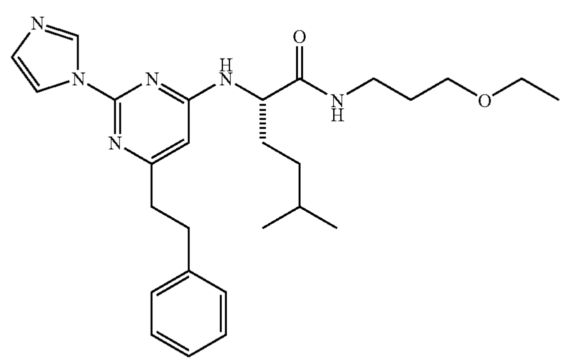 |
| 316 | 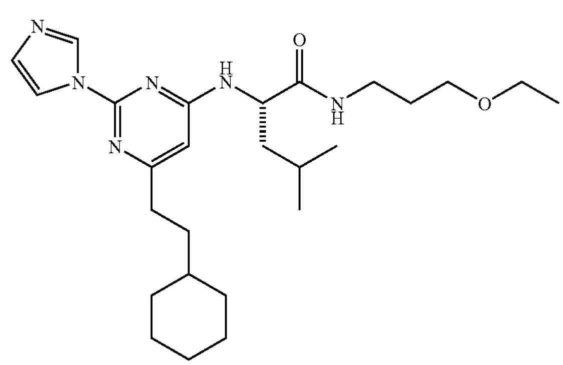 |

TABLE 2A-continued

| Entry | Structure |
|---|---|
| 317 | 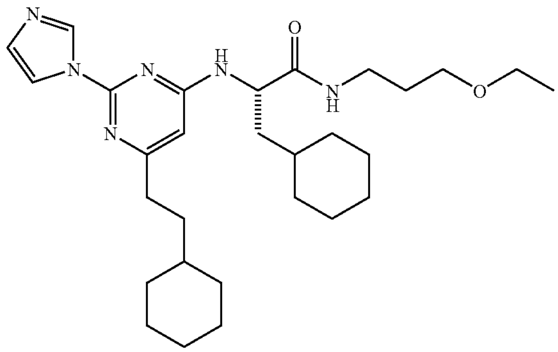 |
| 318 | 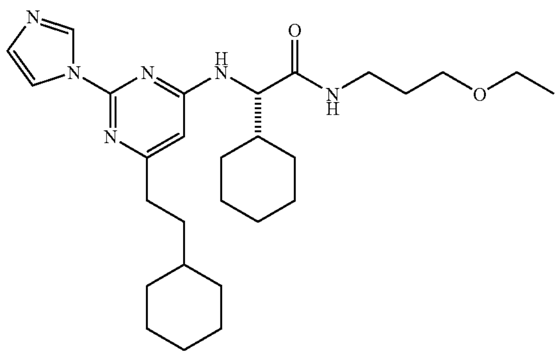 |
| 319 | 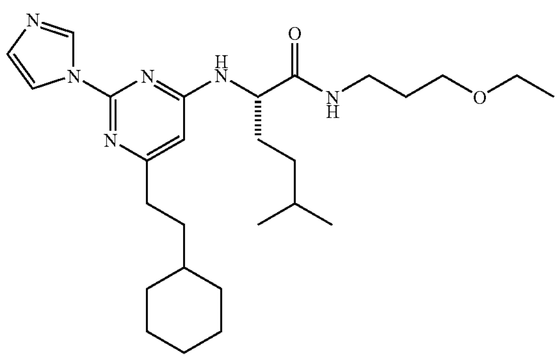 |
| 320 | 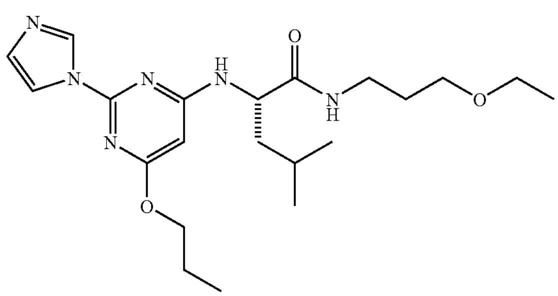 |

TABLE 2A-continued
| Entry | Structure |
|---|---|
| 321 | 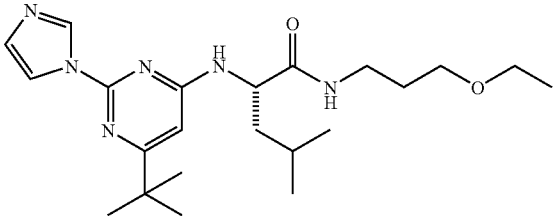 |
| 322 | 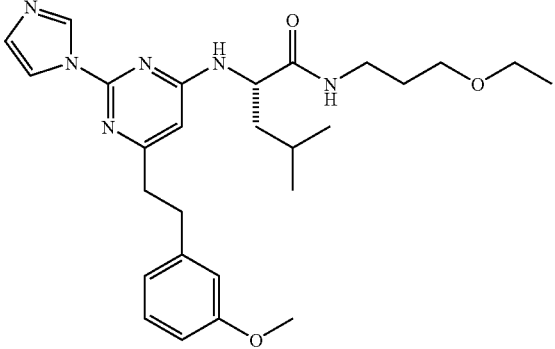 |
| 323 | 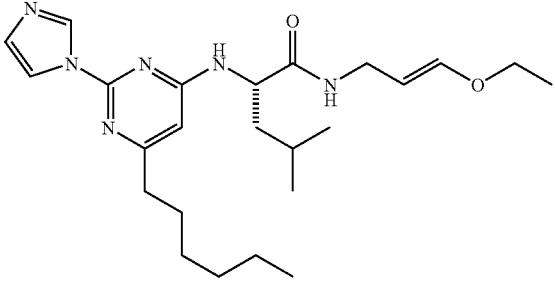 |
| 324 | 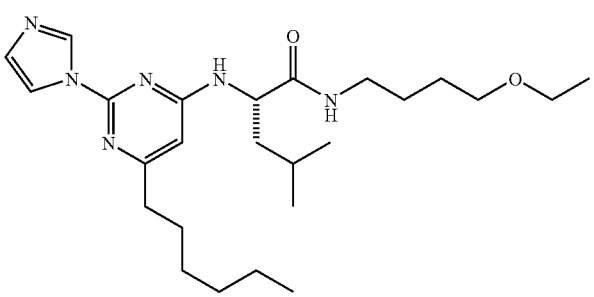 |
| 325 | 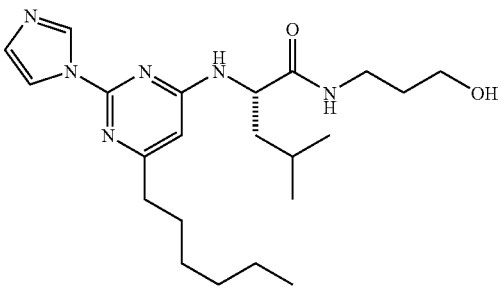 |

TABLE 2A-continued

| Entry | Structure |
|---|---|
| 326 | 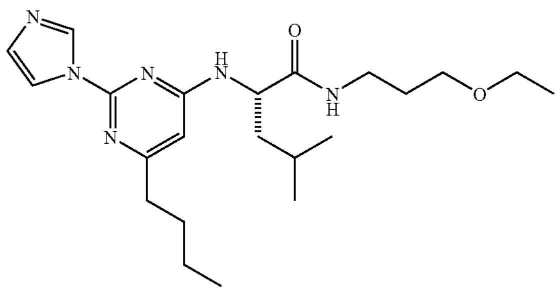 |
| 327 | 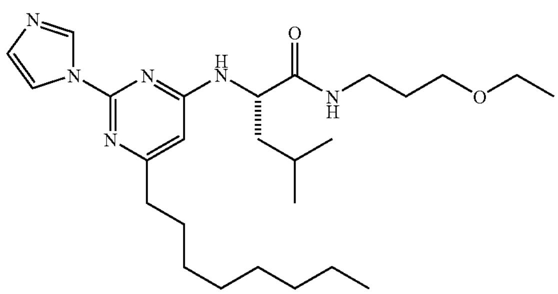 |
| 328 | 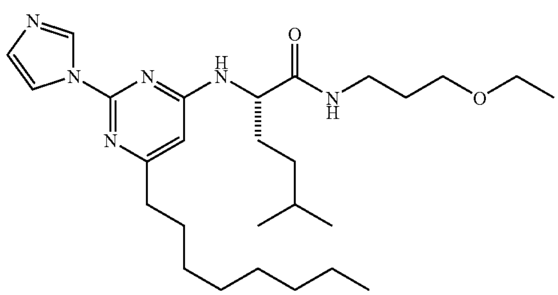 |
| 329 | 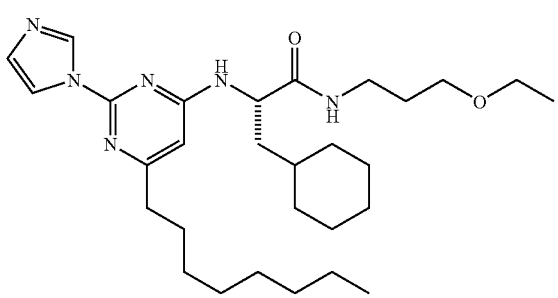 |
| 330 | 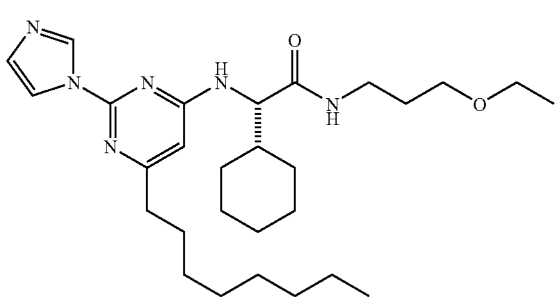 |

TABLE 2A-continued
| Entry | Structure |
|---|---|
| 331 | 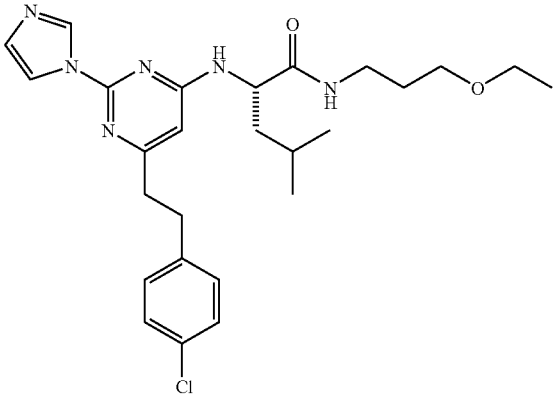 |
| 332 | 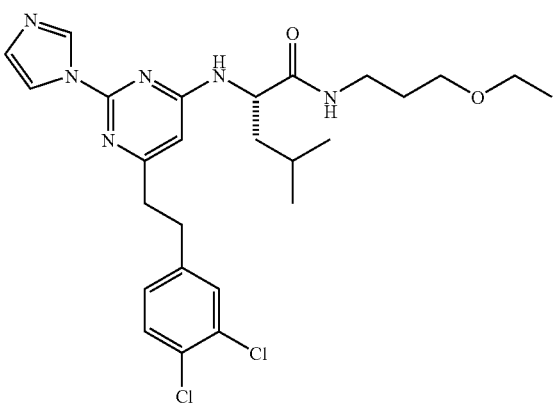 |
| 333 | 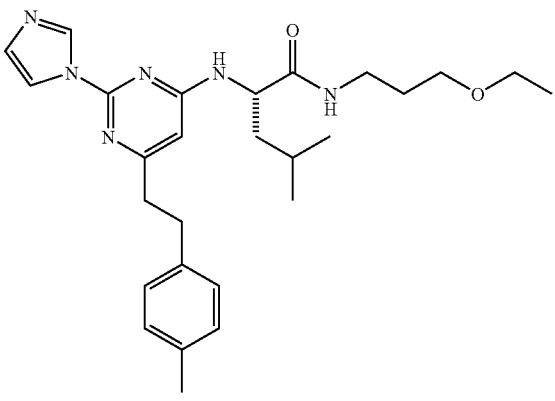 |

TABLE 2A-continued
| Entry | Structure |
|---|---|
| 334 | 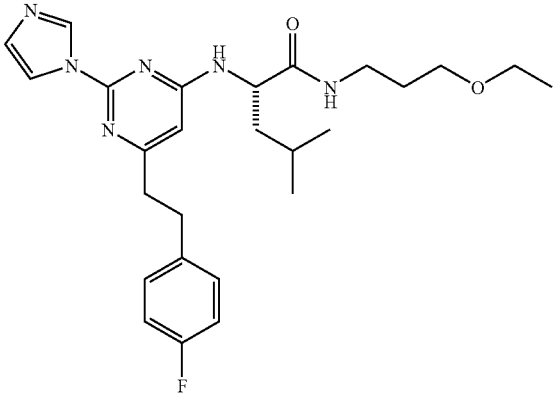 |
| 335 | 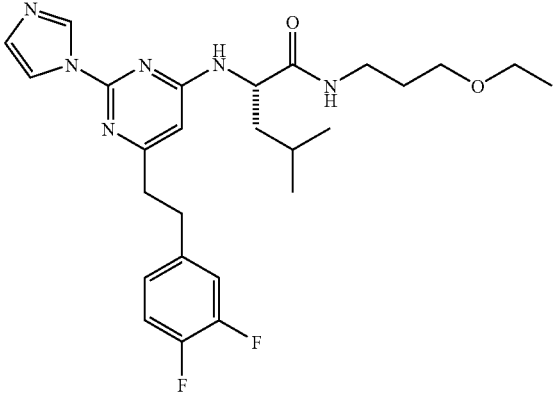 |
| 336 | 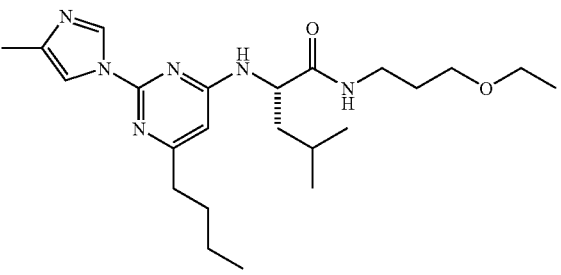 |
| 337 | 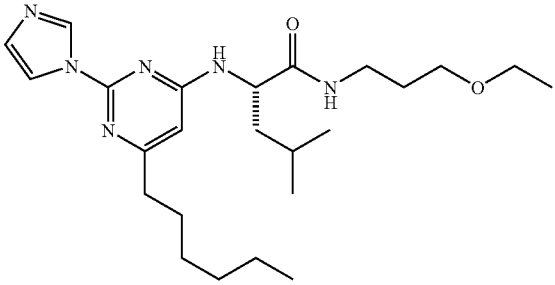 |

TABLE 2A-continued
| Entry | Structure |
|---|---|
| 338 | 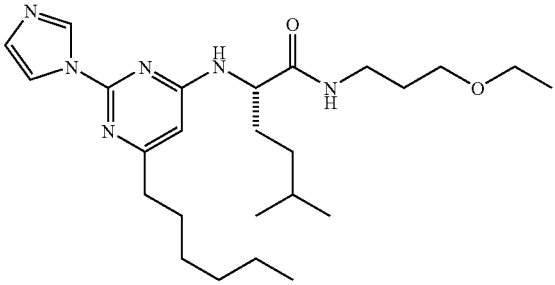 |
| 339 | 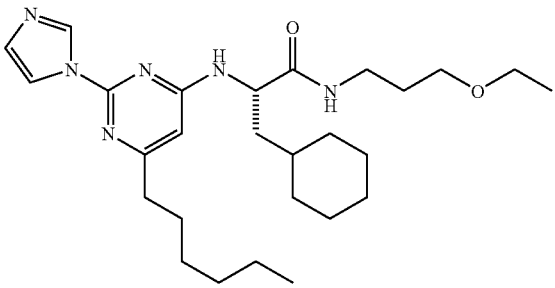 |
| 340 | 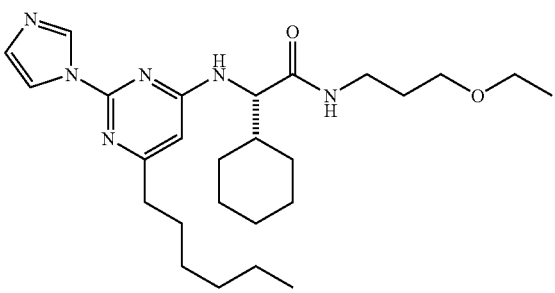 |
| 341 | 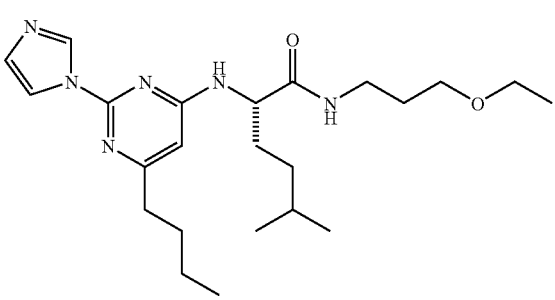 |
| 342 | 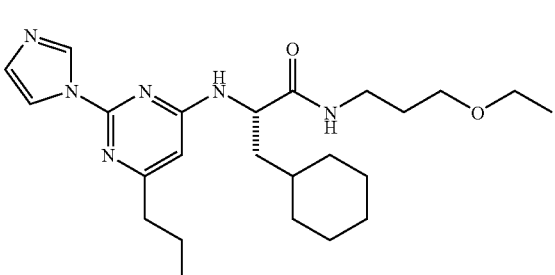 |

TABLE 2A-continued

| Entry | Structure |
|---|---|
| 343 | (2-(imidazol-1-yl)-6-butylpyrimidin-4-yl)amino-cyclohexyl-C(=O)NH-CH₂CH₂CH₂-O-CH₂CH₃ |
| 344 | (2-(pyridin-4-yl)-6-butylpyrimidin-4-yl)amino-leucyl-NH-CH₂CH₂CH₂-O-CH₂CH₃ |
| 345 | (2-(imidazol-1-yl)-6-hexylpyrimidin-4-yl)amino-[CH₂-O-iPr]-C(=O)NH-CH₂CH₂CH₂-O-CH₂CH₃ |
| 346 | (2-(imidazol-1-yl)-6-butylpyrimidin-4-yl)amino-[CH₂-cyclopropyl]-C(=O)NH-CH₂CH₂CH₂-O-CH₂CH₃ |
| 347 | (2-(pyridin-3-yl)-6-butylpyrimidin-4-yl)amino-leucyl-NH-CH₂CH₂CH₂-O-CH₂CH₃ |

TABLE 2A-continued
| Entry | Structure |
|---|---|
| 348 | 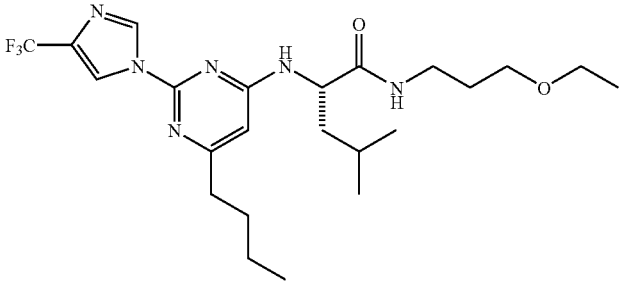 |
| 349 | 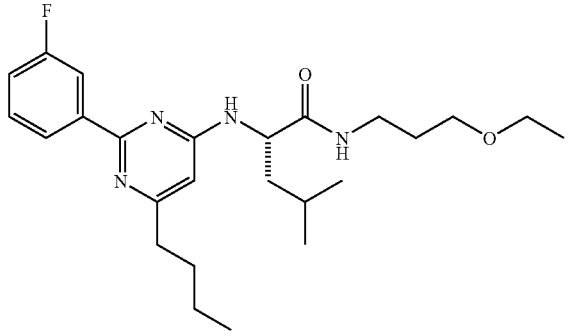 |
| 350 | 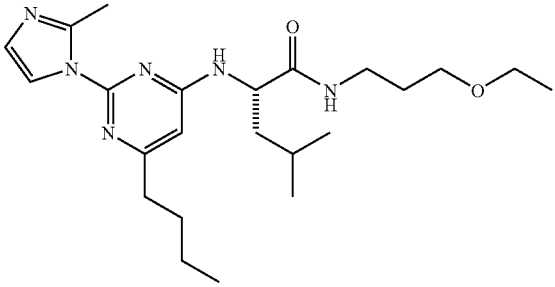 |
| 351 | 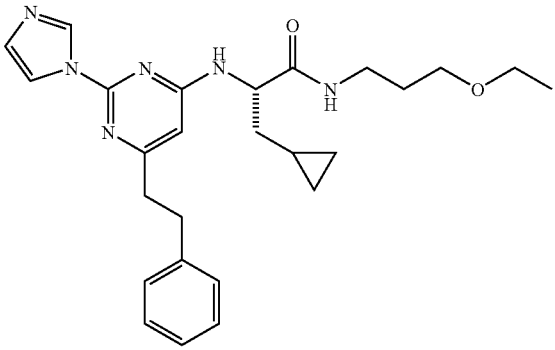 |

TABLE 3

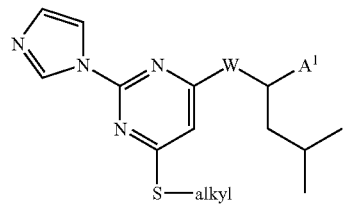

| Ex# | alkyl | W | A[1] |
|---|---|---|---|
| 304 | 1-octyl | NCH$_3$ | —C(=O)NH(CH$_2$)$_4$CH$_3$ |
| 305 | 1-octyl | NH | —C(=O)NH(CH$_2$)$_3$OCH$_3$ |

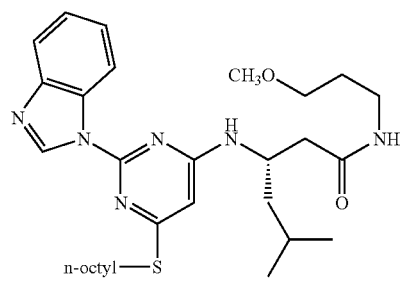

501

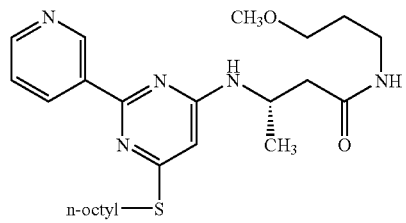

502

TABLE 3-continued

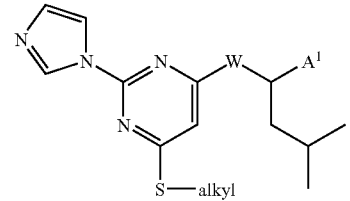

| Ex# | alkyl | W | A[1] |
|---|---|---|---|

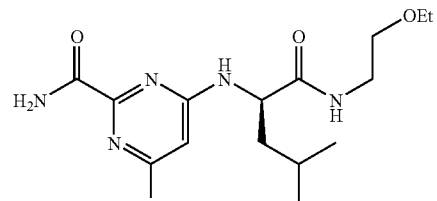

601

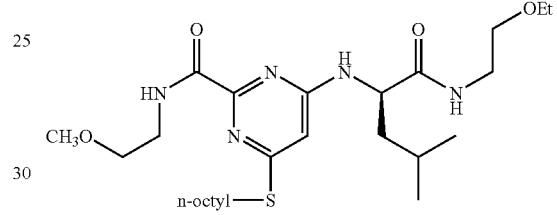

602

In the following Tables 4 to 12, the symbols Ra, Rb, Rc etc. and the symbols ARa, ARb, ARc etc. used to indicate differences in substitution pattern of the compounds and to represent different aromatic substituents, respectively. The meaning of which will be clear to the reader in view of the definitions used in formulae I to V.

TABLE 4

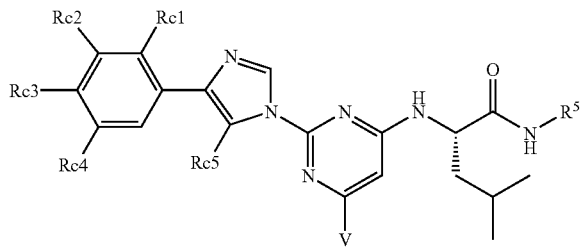

| Example # | Rc1 | Rc2 | Rc3 | Rc4 | Rc5 | V | R[5] |
|---|---|---|---|---|---|---|---|
| 701 | H | H | H | H | H | (CH$_2$)$_3$CH$_3$ | (CH$_2$)$_3$OEt |
| 702 | H | H | H | H | H | (CH$_2$)$_2$CH$_3$ | (CH$_2$)$_3$OEt |
| 703 | H | H | H | H | CH$_3$ | (CH$_2$)$_2$CH$_3$ | (CH$_2$)$_3$OEt |
| 704 | H | H | H | H | CH$_3$ | CH$_3$ | (CH$_2$)$_3$OEt |
| 705 | H | H | H | H | CH$_3$ | (CH$_2$)$_2$CH$_3$ | (CH$_2$)$_3$CF$_3$ |
| 706 | H | H | H | H | CH$_3$ | CH$_3$ | (CH$_2$)$_3$CF$_3$ |
| 707 | H | H | Cl | H | H | (CH$_2$)$_3$CH$_3$ | (CH$_2$)$_3$OEt |
| 708 | H | H | Cl | H | H | C(CH$_3$)$_3$ | (CH$_2$)$_3$OEt |
| 709 | H | H | Cl | H | H | (CH$_2$)$_2$CH$_3$ | (CH$_2$)$_3$OEt |
| 710 | H | H | Cl | H | H | CH$_2$CH$_3$ | (CH$_2$)$_3$OEt |
| 711 | H | H | Cl | H | H | CH$_3$ | (CH$_2$)$_3$OEt |
| 712 | H | H | Cl | H | H | H | (CH$_2$)$_3$OEt |
| 713 | H | H | Cl | H | H | (CH$_2$)$_2$CH$_3$ | (CH$_2$)$_3$CF$_3$ |

TABLE 4-continued

[Structure: A trisubstituted phenyl group (with Rc1, Rc2, Rc3, Rc4) attached to an imidazole (bearing Rc5) linked to a pyrimidine (bearing V) with an NH-leucine-amide-NHR5 side chain]

| Example # | Rc1 | Rc2 | Rc3 | Rc4 | Rc5 | V | R⁵ |
|---|---|---|---|---|---|---|---|
| 714 | H | H | Cl | H | H | CH₃ | (CH₂)₃CF₃ |
| 715 | H | H | Cl | H | H | (CH₂)₃CH₃ | (CH₂)₃NMe(OMe) |
| 716 | H | H | Cl | H | H | (CH₂)₃CH₃ | (CH₂)₄NMe(OMe) |
| 717 | H | H | Cl | H | H | (CH₂)₂CH₃ | cyclopentyl-OEt |
| 718 | H | Cl | H | H | H | (CH₂)₂CH₃ | (CH₂)₃OEt |
| 719 | H | Cl | H | H | H | CH₃ | (CH₂)₃OEt |
| 720 | Cl | H | H | H | H | (CH₂)₃CH₃ | (CH₂)₃OEt |
| 721 | Cl | H | H | H | H | CH₃ | (CH₂)₃OEt |
| 722 | H | Cl | Cl | H | H | (CH₂)₃CH₃ | (CH₂)₃OEt |
| 723 | H | Cl | Cl | H | H | (CH₂)₂CH₃ | (CH₂)₃OEt |
| 724 | H | Cl | Cl | H | H | CH₃ | (CH₂)₃OEt |
| 725 | Cl | H | Cl | H | H | CH₃ | (CH₂)₃OEt |
| 726 | Cl | H | Cl | H | H | CH₃ | (CH₂)₃OEt |
| 727 | H | Cl | H | Cl | H | CH₃ | (CH₂)₃OEt |
| 728 | H | Cl | H | Cl | H | CH₃ | (CH₂)₃OEt |
| 729 | H | Cl | CH₃ | H | CH₃ | CH₃ | (CH₂)₃OEt |
| 730 | H | Cl | CH₃ | H | CH₃ | CH₃ | (CH₂)₃OEt |
| 731 | H | F | Cl | H | H | (CH₂)₂CH₃ | (CH₂)₃OEt |
| 732 | H | H | F | H | H | (CH₂)₃CH₃ | (CH₂)₃OEt |
| 733 | H | H | F | H | H | (CH₂)₂CH₃ | (CH₂)₃OEt |
| 734 | H | F | H | H | H | (CH₂)₃CH₃ | (CH₂)₃OEt |
| 735 | H | F | H | H | H | (CH₂)₂CH₃ | (CH₂)₃OEt |
| 736 | H | F | H | H | H | (CH₂)₃CH₃ | (CH₂)₃OEt |
| 737 | H | F | F | H | H | (CH₂)₂CH₃ | (CH₂)₃OEt |
| 738 | H | F | F | H | H | CH₃ | (CH₂)₃OEt |
| 739 | H | F | CH₃ | H | H | CH₃ | (CH₂)₃OEt |
| 740 | H | F | CH₃ | H | H | CH₃ | (CH₂)₃CF₃ |
| 741 | H | H | CH₃ | H | H | (CH₂)₃CH₃ | (CH₂)₃OEt |
| 742 | H | H | CH₃ | H | H | (CH₂)₃CH₃ | (CH₂)₃OEt |
| 743 | H | H | OCH₃ | H | H | (CH₂)₃CH₃ | (CH₂)₃OEt |
| 744 | H | H | OCH₃ | H | H | (CH₂)₃CH₃ | (CH₂)₃OEt |
| 745 | H | H | OCH₃ | H | H | (CH₂)₃CH₃ | (CH₂)₃OEt |
| 746 | H | OCH₃ | H | H | H | (CH₂)₃CH₃ | (CH₂)₃OEt |
| 747 | OCH₃ | H | H | H | H | (CH₂)₃CH₃ | (CH₂)₃OEt |
| 748 | H | H | OCF₃ | H | H | (CH₂)₃CH₃ | (CH₂)₃OEt |
| 749 | H | H | OCF₃ | H | H | (CH₂)₃CH₃ | (CH₂)₃OEt |
| 750 | H | H | OCF₃ | H | H | (CH₂)₃CH₃ | (CH₂)₃OEt |
| 751 | H | H | OCF₃ | H | H | CH₃ | (CH₂)₃OEt |
| 752 | H | H | OCF₃ | H | H | H | (CH₂)₃OEt |
| 753 | H | H | OCF₃ | H | H | (CH₂)₃CH₃ | (CH₂)₃OEt |
| 754 | H | H | OCF₃ | H | H | (CH₂)₃CH₃ | (CH₂)₃OEt |
| 755 | H | OCF₃ | H | H | H | (CH₂)₃CH₃ | (CH₂)₃OEt |
| 756 | OCF₃ | H | H | H | H | (CH₂)₃CH₃ | (CH₂)₃OEt |
| 757 | H | H | OCHF₂ | H | H | (CH₂)₃CH₃ | (CH₂)₃OEt |
| 758 | H | H | CF₃ | H | H | (CH₂)₃CH₃ | (CH₂)₃OEt |
| 759 | H | H | CF₃ | H | H | (CH₂)₃CH₃ | (CH₂)₃OEt |
| 760 | H | H | CF₃ | H | H | (CH₂)₃CH₃ | (CH₂)₃OEt |
| 761 | H | H | CF₃ | H | H | CH₃ | (CH₂)₃OEt |
| 762 | H | H | CF₃ | H | H | H | (CH₂)₃OEt |
| 763 | H | CF₃ | H | H | H | (CH₂)₃CH₃ | (CH₂)₃OEt |
| 764 | CF₃ | H | H | H | H | (CH₂)₃CH₃ | (CH₂)₃OEt |
| 765 | H | H | OH | H | H | (CH₂)₃CH₃ | (CH₂)₃OEt |
| 766 | H | H | OH | H | H | (CH₂)₃CH₃ | (CH₂)₃OEt |
| 767 | H | H | CN | H | H | (CH₂)₃CH₃ | (CH₂)₃OEt |
| 768 | H | H | CN | H | H | (CH₂)₃CH₃ | (CH₂)₃OEt |
| 769 | H | H | NO₂ | H | H | (CH₂)₃CH₃ | (CH₂)₃OEt |
| 770 | H | H | NH₂ | H | H | (CH₂)₃CH₃ | (CH₂)₃OEt |
| 771 | H | OBn | H | H | H | (CH₂)₃CH₃ | (CH₂)₃OEt |

TABLE 4-continued

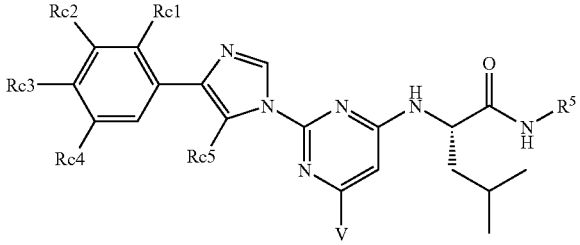

| Example # | Rc1 | Rc2 | Rc3 | Rc4 | Rc5 | V | $R^5$ |
|---|---|---|---|---|---|---|---|
| 772 | H | OBn | H | H | H | $CH_3$ | $(CH_2)_3OEt$ |
| 773 | H | H | $OCH_2CF_3$ | H | H | $(CH_2)_3CH_3$ | $(CH_2)_3OEt$ |
| 774 | H | H | $OCH_2CF_3$ | H | H | $(CH_2)_3CH_3$ | $(CH_2)_3OEt$ |
| 775 | H | $CH_3$ | $OCF_3$ | H | H | $(CH_2)_3CH_3$ | $(CH_2)_3OEt$ |
| 776 | H | Cl | $OCF_3$ | H | H | $(CH_2)_3CH_3$ | $(CH_2)_3OEt$ |
| 777 | $OCH_3$ | H | H | $OCF_3$ | H | $(CH_2)_3CH_3$ | $(CH_2)_3OEt$ |
| 778 | $OCH_3$ | H | H | $OCF_3$ | H | $(CH_2)_3CH_3$ | $(CH_2)_3OEt$ |
| 779 | $OCH_3$ | H | H | $OCF_3$ | H | $(CH_2)_3CH_3$ | $(CH_2)_3OEt$ |
| 780 | H | F | $CF_3$ | H | H | $(CH_2)_3CH_3$ | $(CH_2)_3OEt$ |
| 781 | F | H | $CF_3$ | H | H | $(CH_2)_3CH_3$ | $(CH_2)_3OEt$ |
| 782 | F | H | $CF_3$ | H | H | $(CH_2)_3CH_3$ | $(CH_2)_3OEt$ |
| 783 | H | $CF_3$ | F | H | H | $(CH_2)_3CH_3$ | $(CH_2)_3OEt$ |
| 784 | H | $CF_3$ | Cl | H | H | $(CH_2)_3CH_3$ | $(CH_2)_3OEt$ |
| 785 | H | $CF_3$ | Cl | H | H | $(CH_2)_3CH_3$ | $(CH_2)_3OEt$ |
| 786 | H | $CF_3$ | Cl | H | H | $(CH_2)_3CH_3$ | $(CH_2)_3OEt$ |
| 787 | H | CN | $OCH_3$ | H | H | $(CH_2)_3CH_3$ | $(CH_2)_3OEt$ |
| 788 | $CF_3$ | H | $CF_3$ | H | H | $(CH_2)_3CH_3$ | $(CH_2)_3OEt$ |
| 789 | H | $CF_3$ | H | $CF_3$ | H | $(CH_2)_3CH_3$ | $(CH_2)_3OEt$ |
| 790 | H | $OCH_3$ | $OCH_3$ | H | H | $(CH_2)_3CH_3$ | $(CH_2)_3OEt$ |
| 791 | H | H | $SCH_3$ | H | H | $(CH_2)_3CH_3$ | $(CH_2)_3OEt$ |
| 792 | H | H | $SCF_3$ | H | H | $(CH_2)_3CH_3$ | $(CH_2)_3OEt$ |
| 793 | H | H | $OCF_3$ | H | H | $(CH_2)_3CH_3$ | $(CH_2)_3OEt$ |
| 794 | H | H | $OCF_3$ | H | H | $(CH_2)_3CH_3$ | $(CH_2)_3OEt$ |
| 795 | H | H | $OCF_3$ | H | H | $(CH_2)_3CH_3$ | $(CH_2)_3OEt$ |
| 796 | H | H | $OCF_3$ | H | H | $(CH_2)_3CH_3$ | $(CH_2)_3OEt$ |
| 797 | H | H | $OCF_3$ | H | H | $(CH_2)_3CH_3$ | $(CH_2)_3OEt$ |
| 798 | H | H | $OCF_3$ | H | H | $(CH_2)_3CH_3$ | $(CH_2)_3OEt$ |
| 799 | H | H | $OCF_3$ | H | H | $(CH_2)_3CH_3$ | $(CH_2)_3S(O)_2CH_3$ |
| 800 | H | H | $OCF_3$ | H | H | $(CH_2)_3CH_3$ | $(CH_2)_3S(O)_2CH_3$ |

TABLE 5

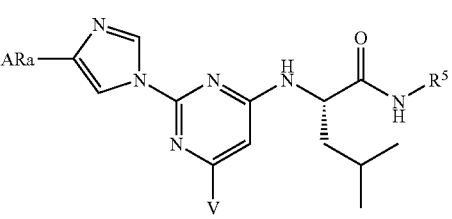

| Example # | ARa | V | $R^5$ |
|---|---|---|---|
| 801 | 2,3-dihydro-1,4-benzodioxin-6-yl | $(CH_2)_2CH_3$ | $(CH_2)_3OEt$ |
| 802 | 1,3-benzodioxol-5-yl | $(CH_2)_2CH_3$ | $(CH_2)_3OEt$ |

TABLE 5-continued

[Structure: ARa-imidazole-pyrimidine(V)-NH-CH(CH2CH(CH3)2)-C(O)-NH-R5]

| Example # | ARa | V | R5 |
|---|---|---|---|
| 803 | 2,2-difluoro-benzo[1,3]dioxol-5-yl | (CH2)2CH3 | (CH2)3OEt |
| 804 | benzo[1,3]dioxol-4-yl | (CH2)2CH3 | (CH2)3OEt |
| 805 | 2,2-difluoro-benzo[1,3]dioxol-4-yl | (CH2)2CH3 | (CH2)3OEt |
| 806 | 2,3-dihydrobenzofuran-5-yl | (CH2)2CH3 | (CH2)3OEt |
| 807 | 2-methylbenzofuran-5-yl | (CH2)3CH3 | (CH2)3OEt |
| 808 | benzothiazol-6-yl | (CH2)2CH3 | (CH2)3OEt |
| 809 | pyridin-2-yl | (CH2)3CH3 | (CH2)3OEt |
| 810 | pyridin-4-yl | (CH2)3CH3 | (CH2)3OEt |
| 811 | 6-methoxypyridin-3-yl | (CH2)2CH3 | (CH2)3OEt |
| 812 | furan-3-yl | (CH2)3CH3 | (CH2)3OEt |
| 813 | 2-methylfuran-3-yl | (CH2)3CH3 | (CH2)3OEt |
| 814 | 2-methylfuran-3-yl | (CH2)2CH3 | (CH2)3OEt |
| 815 | 2-trifluoromethylfuran-3-yl | (CH2)3CH3 | (CH2)3OEt |
| 816 | 5-trifluoromethylfuran-2-yl | (CH2)3CH3 | (CH2)3OEt |
| 817 | 5-trifluoromethylfuran-2-yl | (CH2)2CH3 | (CH2)3CF3 |
| 818 | 2-trifluoromethylfuran-3-yl | (CH2)3CH3 | (CH2)3OEt |

TABLE 5-continued
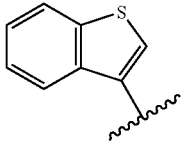
| Example # | ARa | V | R⁵ |
|---|---|---|---|
| 819 | 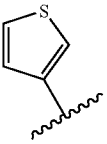 | (CH₂)₂CH₃ | (CH₂)₃OEt |
| 820 | 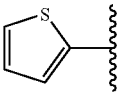 | (CH₂)₂CH₃ | (CH₂)₃OEt |
| 821 | 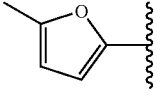 | (CH₂)₂CH₃ | (CH₂)₃OEt |
| 822 | 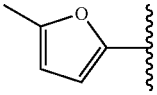 | (CH₂)₂CH₃ | (CH₂)₃OEt |
| 823 | 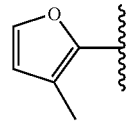 | CH₃ | (CH₂)₃OEt |
| 824 | 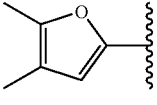 | (CH₂)₂CH₃ | (CH₂)₃OEt |
| 825 | 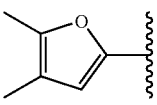 | (CH₂)₃CH₃ | (CH₂)₃OEt |
| 826 | 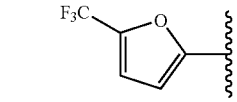 | (CH₂)₂CH₃ | (CH₂)₃OEt |
TABLE 5-continued
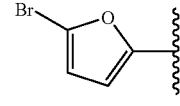
| Example # | ARa | V | R⁵ |
|---|---|---|---|
| 827 | 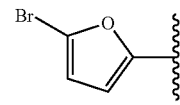 | (CH₂)₃CH₃ | (CH₂)₃OEt |
| 828 | 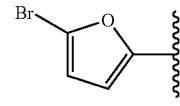 | (CH₂)₃CH₃ | (CH₂)₃OEt |
| 829 | 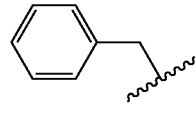 | (CH₂)₂CH₃ | (CH₂)₃OEt |
| 830 | 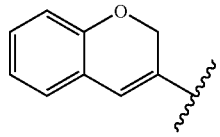 | (CH₂)₃CH₃ | (CH₂)₃CF₃ |
| 831 | 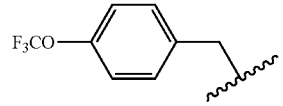 | (CH₂)₃CH₃ | (CH₂)₃OEt |
| 945 |  | (CH₂)₂CH₃ | (CH₂)₃OEt |
| 832 |  | (CH₂)₃CH₃ | (CH₂)₃OEt |

TABLE 7

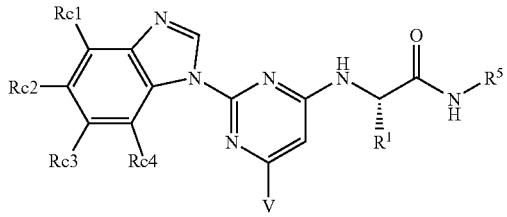

| Example # | Rc1 | Rc2 | Rc3 | Rc4 | V | R$^1$ | R$^5$ |
|---|---|---|---|---|---|---|---|
| 833 | H | H | H | H | $(CH_2)_3CH_3$ | $CH_2CH(CH_3)_2$ | $(CH_2)_3OEt$ |
| 834 | H | H | H | H | $(CH_2)_5CH_3$ | $CH_2CH(CH_3)_2$ | $(CH_2)_3OEt$ |
| 835 | H | H | H | H | $(CH_2)_3SiMe_3$ | $CH_2CH(CH_3)_2$ | $(CH_2)_3OEt$ |
| 836 | H | H | H | H | CHMe—$(CH_2)_2CH_3$ | $CH_2CH(CH_3)_2$ | $(CH_2)_3OEt$ |
| 837 | H | H | H | H | $(CH_2)_3OtBu$ | $CH_2CH(CH_3)_2$ | $(CH_2)_3OEt$ |
| 838 | H | H | H | H | $(CH_2)_3F$ | $CH_2CH(CH_3)_2$ | $(CH_2)_3OEt$ |
| 839 | H | H | H | H | $CH_2CO_2Et$ | $CH_2CH(CH_3)_2$ | $(CH_2)_3OEt$ |
| 840 | H | H | H | H | $(CH_2)_3CH_3$ | $CH_2CH(CH_3)_2$ | $(CH_2)_3OMe$ |
| 841 | H | H | H | H | $(CH_2)_3CH_3$ | $CH_2CH(CH_3)_2$ | $(CH_2)_3SMe$ |
| 842 | H | H | H | H | $(CH_2)_3CH_3$ | $CH_2CH(CH_3)_2$ | $(CH_2)_3CH_3$ |
| 843 | H | H | H | H | $(CH_2)_3CH_3$ | $CH_2CH(CH_3)_2$ | $(CH_2)_3CF_3$ |
| 844 | H | H | H | H | $(CH_2)_3CH_3$ | $CH_2CH(CH_3)_2$ | $(CH_2)_3CF_3$ |
| 845 | H | H | H | H | $(CH_2)_3CH_3$ | $CH_2CH(CH_3)_2$ | $(CH_2)_3CN$ |
| 846 | H | H | H | H | $(CH_2)_3CH_3$ | $CH_2CH(CH_3)_2$ | $(CH_2)_4CN$ |
| 847 | H | H | H | H | $(CH_2)_3CH_3$ | $CH_2CH(CH_3)_2$ | $(CH_2)_3NHCOOMe$ |
| 848 | H | H | H | H | $(CH_2)_3CH_3$ | $CH_2CH(CH_3)_2$ | $CH(CH_3)CH_2C_6H_4$ (p-OMe) |
| 849 | H | H | H | H | $(CH_2)_3CH_3$ | $CH_2CH(CH_3)_2$ | $(CH_2)_2C_6H_4$ (p-OMe) |
| 850 | H | H | H | H | $(CH_2)_3CH_3$ | $CH_2CH(CH_3)_2$ | $(CH_2)_3NMe(OMe)$ |
| 851 | H | $CF_3$ | H | H | $(CH_2)_3CH_3$ | $CH_2CH(CH_3)_2$ | $(CH_2)_3OEt$ |
| 852 | H | $CF_3$ | H | H | $(CH_2)_3CH_3$ | $CH_2CH(CH_3)_2$ | $(CH_2)_3OEt$ |
| 853 | H | $CF_3$ | H | H | $CH_2CH_3$ | $CH_2CH(CH_3)_2$ | $(CH_2)_3OEt$ |
| 854 | H | $CF_3$ | H | H | $(CH_2)_3CH_3$ | $CH_2CH(CH_3)_2$ | $(CH_2)_3CF_3$ |
| 855 | H | $CF_3$ | H | H | $CH_3$ | $CH_2CH(CH_3)_2$ | $(CH_2)_3CF_3$ |
| 856 | H | $CF_3$ | H | H | $(CH_2)_3CH_3$ | $CH_2CH(CH_3)_2$ | $(CH_2)_3OMe$ |
| 857 | H | $CF_3$ | H | H | $(CH_2)_3CH_3$ | $CH_2CH(CH_3)_2$ | $(CH_2)_3CF_3$ |
| 858 | H | H | $CF_3$ | H | $(CH_2)_3CH_3$ | $CH_2CH(CH_3)_2$ | $(CH_2)_3OEt$ |
| 859 | H | H | $CF_3$ | H | $(CH_2)_3CH_3$ | $CH_2CH(CH_3)_2$ | $(CH_2)_3OEt$ |
| 860 | H | H | $CF_3$ | H | $(CH_2)_3CH_3$ | $CH_2CH(CH_3)_2$ | $(CH_2)_3OEt$ |
| 861 | H | H | $CF_3$ | H | $(CH_2)_3CH_3$ | $CH_2CH(CH_3)_2$ | $(CH_2)_3CF_3$ |
| 862 | H | H | $CF_3$ | H | $CH_3$ | $CH_2CH(CH_3)_2$ | $(CH_2)_3CF_3$ |
| 863 | H | H | $CF_3$ | H | $(CH_2)_3CH_3$ | $CH_2CH(CH_3)_2$ | $(CH_2)_3OMe$ |
| 864 | H | H | $CF_3$ | H | $(CH_2)_3CH_3$ | $CH_2CH(CH_3)_2$ | $(CH_2)_3CF_3$ |
| 865 | H | Cl | H | H | $(CH_2)_3CH_3$ | $CH_2CH(CH_3)_2$ | $(CH_2)_3OEt$ |
| 866 | H | H | Cl | H | $(CH_2)_3CH_3$ | $CH_2CH(CH_3)_2$ | $(CH_2)_3OEt$ |
| 867 | H | $OCH_3$ | H | H | $(CH_2)_3CH_3$ | $CH_2CH(CH_3)_2$ | $(CH_2)_3OEt$ |
| 868 | H | H | $OCH_3$ | H | $(CH_2)_3CH_3$ | $CH_2CH(CH_3)_2$ | $(CH_2)_3OEt$ |
| 869 | H | F | H | H | $(CH_2)_3CH_3$ | $CH_2CH(CH_3)_2$ | $(CH_2)_3OEt$ |
| 870 | H | F | H | H | $(CH_2)_3CH_3$ | $CH_2CH(CH_3)_2$ | $(CH_2)_3OEt$ |
| 871 | H | F | H | H | $(CH_2)_3CH_3$ | $CH_2CH(CH_3)_2$ | $(CH_2)_3CF_3$ |
| 872 | H | F | H | H | $(CH_2)_3CH_3$ | $CH_2CH(CH_3)_2$ | $(CH_2)_2C_6H_4$ (p-OMe) |
| 873 | H | H | F | H | $(CH_2)_3CH_3$ | $CH_2CH(CH_3)_2$ | $(CH_2)_3OEt$ |
| 874 | H | H | F | H | $(CH_2)_3CH_3$ | $CH_2CH(CH_3)_2$ | $(CH_2)_3OEt$ |
| 875 | H | H | F | H | $(CH_2)_3CH_3$ | $CH_2CH(CH_3)_2$ | $(CH_2)_3CF_3$ |
| 876 | H | H | F | H | $(CH_2)_3CH_3$ | $CH_2CH(CH_3)_2$ | $(CH_2)_2C_6H_4$ (p-OMe) |
| 877 | H | CN | H | H | $(CH_2)_3CH_3$ | $CH_2CH(CH_3)_2$ | $(CH_2)_3OEt$ |
| 878 | H | H | CN | H | $(CH_2)_3CH_3$ | $CH_2CH(CH_3)_2$ | $(CH_2)_3OEt$ |
| 879 | H | Cl | Cl | H | $(CH_2)_3CH_3$ | $CH_2CH(CH_3)_2$ | $(CH_2)_3OEt$ |
| 880 | H | Cl | Cl | H | $(CH_2)_3CH_3$ | $CH_2CH(CH_3)_2$ | $(CH_2)_3CF_3$ |
| 881 | H | Cl | Cl | H | $(CH_2)_3CH_3$ | $CH_2CH(CH_3)_2$ | $(CH_2)_3CF_3$ |
| 882 | H | F | F | H | $(CH_2)_3CH_3$ | $CH_2CH(CH_3)_2$ | $(CH_2)_3OEt$ |
| 883 | H | F | F | H | $(CH_2)_3CH_3$ | $CH_2CH(CH_3)_2$ | $(CH_2)_3OEt$ |
| 884 | H | F | F | H | $(CH_2)_3CH_3$ | $CH_2CH(CH_3)_2$ | $(CH_2)_3OEt$ |
| 885 | H | F | F | H | $(CH_2)_3CH_3$ | $CH_2CH(CH_3)_2$ | $(CH_2)_3OEt$ |
| 886 | H | F | F | H | $(CH_2)_3CH_3$ | $CH_2CH(CH_3)_2$ | $(CH_2)_3CF_3$ |
| 887 | H | F | F | H | $(CH_2)_3CH_3$ | $CH_2CH(CH_3)_2$ | $(CH_2)_3NMe(OMe)$ |
| 888 | F | F | H | H | $(CH_2)_3CH_3$ | $CH_2CH(CH_3)_2$ | $(CH_2)_3OEt$ |
| 889 | H | H | F | F | $(CH_2)_3CH_3$ | $CH_2CH(CH_3)_2$ | $(CH_2)_3OEt$ |
| 890 | H | $OCF_3$ | H | H | $(CH_2)_3CH_3$ | $CH_2CH(CH_3)_2$ | $(CH_2)_3OEt$ |
| 891 | H | H | $OCF_3$ | H | $(CH_2)_3CH_3$ | $CH_2CH(CH_3)_2$ | $(CH_2)_3OEt$ |

TABLE 8

| Example # | Rc | V | R⁵ |
|---|---|---|---|
| 892 | Cl | (CH₂)₂CH₃ | (CH₂)₃OEt |
| 893 | phenyl | (CH₂)₂CH₃ | (CH₂)₃OEt |
| 894 | 4-(CF₃)phenyl | (CH₂)₂CH₃ | (CH₂)₃OEt |
| 895 | 3-(CF₃)phenyl | (CH₂)₂CH₃ | (CH₂)₃OEt |
| 896 | 4-(F₃CO)phenyl | (CH₂)₂CH₃ | (CH₂)₃OEt |
| 897 | 3-(F₃CO)phenyl | (CH₂)₂CH₃ | (CH₂)₃OEt |
| 898 | 4-Cl-phenyl | (CH₂)₂CH₃ | (CH₂)₃OEt |
| 899 | 3-Cl-phenyl | (CH₂)₂CH₃ | (CH₂)₃OEt |
| 900 | 4-F-phenyl | (CH₂)₂CH₃ | (CH₂)₃OEt |
| 901 | 2-F-phenyl | (CH₂)₂CH₃ | (CH₂)₃OEt |
| 902 | furan-2-yl | (CH₂)₂CH₃ | (CH₂)₃OEt |
| 903 | benzofuran-2-yl | (CH₂)₂CH₃ | (CH₂)₃OEt |
| 904 | 5-F-benzofuran-2-yl | (CH₂)₂CH₃ | (CH₂)₃OEt |
| 905 | 4-Cl-phenoxy | (CH₂)₂CH₃ | (CH₂)₃OEt |
| 906 | 4-(F₃CO)phenoxy | (CH₂)₂CH₃ | (CH₂)₃OEt |

TABLE 9

[Structure: Rc-substituted pyridine connected to pyrimidine (with V substituent) linked via NH to a chiral leucine-derived amide with NHR⁵]

| Example # | Rc | V | R⁵ |
|---|---|---|---|
| 907 | Br | (CH$_2$)$_3$CH$_3$ | (CH$_2$)$_3$OEt |
| 908 | Br | (CH$_2$)$_2$CH$_3$ | (CH$_2$)$_3$OEt |
| 909 | Br | (CH$_2$)$_2$CH$_3$ | (CH$_2$)$_3$CF$_3$ |
| 910 | phenyl | (CH$_2$)$_2$CH$_3$ | (CH$_2$)$_3$OEt |
| 911 | 3-(F$_3$C)phenyl | (CH$_2$)$_3$CH$_3$ | (CH$_2$)$_3$OEt |
| 912 | 4-(F$_3$C)phenyl | (CH$_2$)$_3$CH$_3$ | (CH$_2$)$_3$OEt |
| 913 | 2-(OCF$_3$)phenyl | (CH$_2$)$_3$CH$_3$ | (CH$_2$)$_3$OEt |
| 914 | 3-(F$_3$CO)phenyl | (CH$_2$)$_3$CH$_3$ | (CH$_2$)$_3$OEt |
| 915 | 3-(F$_3$CO)phenyl | (CH$_2$)$_2$CH$_3$ | (CH$_2$)$_3$OEt |
| 916 | 2-F-phenyl | (CH$_2$)$_2$CH$_3$ | (CH$_2$)$_3$CF$_3$ |
| 917 | 3-(F$_3$CO)phenyl | (CH$_2$)$_2$CH$_3$ | (CH$_2$)$_3$NMe(OMe) |
| 918 | 3-(F$_3$CO)phenyl | (CH$_2$)$_2$CH$_3$ | (CH$_2$)$_2$-(4-methoxyphenyl) |

TABLE 9-continued

| Example # | Rc | V | R⁵ |
| --- | --- | --- | --- |
| 919 | F₃CO-C₆H₄- | (CH₂)₃CH₃ | (CH₂)₃OEt |
| 920 | F₃CO-C₆H₄- | (CH₂)₂CH₃ | (CH₂)₃OEt |
| 921 | 5-F-benzofuran-2-yl | (CH₂)₃CH₃ | (CH₂)₃OEt |
| 922 | F₃CO-C₆H₄-O- | (CH₂)₃CH₃ | (CH₂)₃OEt |

TABLE 10

| Example # | Arb | V | R⁵ |
| --- | --- | --- | --- |
| 923 | 4-(4-F₃CO-phenyl)-imidazol-1-yl | (CH₂)₃CH₃ | -CH₂-(furan-2-yl) |
| 924 | 4-(4-F₃CO-phenyl)-imidazol-1-yl | (CH₂)₃CH₃ | -(CH₂)₃-(furan-2-yl) |
| 925 | 4-(4-F₃CO-phenyl)-imidazol-1-yl | (CH₂)₃CH₃ | -(CH₂)₃-(furan-2-yl) |

TABLE 10-continued

| Example # | Arb | V | R⁵ |
|---|---|---|---|
| 926 | F₃CO-phenyl-imidazole | (CH₂)₂CH₃ | -(CH₂)₄-furan-2-yl |
| 927 | F₃CO-phenyl-imidazole | (CH₂)₃CH₃ | -CH₂-(tetrahydrofuran-2-yl) |
| 928 | F₃CO-phenyl-imidazole | (CH₂)₃CH₃ | -(CH₂)₂-(tetrahydrofuran-2-yl) |
| 929 | F₃CO-phenyl-imidazole | (CH₂)₃CH₃ | -(CH₂)₃-(tetrahydrofuran-2-yl) |
| 930 | F₃CO-phenyl-imidazole | (CH₂)₃CH₃ | -(CH₂)₃-furan-3-yl |
| 931 | F₃CO-phenyl-imidazole | (CH₂)₃CH₃ | -CH₂-(tetrahydrofuran-3-yl) |
| 932 | F₃CO-phenyl-imidazole | (CH₂)₃CH₃ | -(CH₂)₂-(tetrahydrofuran-3-yl) |
| 933 | F₃CO-phenyl-imidazole | (CH₂)₂CH₃ | -(CH₂)₂-(tetrahydrofuran-3-yl) |
| 934 | F₃CO-phenyl-imidazole | (CH₂)₃CH₃ | -(CH₂)₃-(tetrahydrofuran-3-yl) |

TABLE 10-continued

| Example # | Arb | V | R⁵ |
|---|---|---|---|
| 935 | F₃CO-phenyl-imidazole | $(CH_2)_3CH_3$ | (CH₂)₂-tetrahydropyran-2-yl |
| 936 | F₃CO-phenyl-imidazole | $(CH_2)_3CH_3$ | CH₂-tetrahydropyran-4-yl |
| 937 | F₃CO-phenyl-imidazole | $(CH_2)_3CH_3$ | (CH₂)₂-tetrahydropyran-4-yl |
| 938 | F₃CO-phenyl-imidazole | $(CH_2)_3CH_3$ | (CH₂)₂OCH₂CH₂OCH₃ |
| 939 | F₃CO-phenyl-imidazole | $(CH_2)_3CH_3$ | (CH₂)₂-cyclopentyl |
| 940 | F₃CO-phenyl-imidazole | $(CH_2)_3CH_3$ | (CH₂)₂CH(CH₃)₂ |
| 941 | F₃CO-phenyl-imidazole | $(CH_2)_3CH_3$ | (CH₂)₃-(5-methyloxazol-2-yl) |
| 942 | F₃CO-phenyl-imidazole | $(CH_2)_3CH_3$ | (CH₂)₃-(4-methylthiazol-2-yl) |
| 943 | F₃CO-phenyl-imidazole | $(CH_2)_3CH_3$ | (CH₂)₂-(4-methoxyphenyl) |

TABLE 10-continued

| Example # | Arb | V | R⁵ |
|---|---|---|---|
| 944 | F₃CO-phenyl-imidazole | (CH₂)₃CH₃ | -(CH₂)₃C(O)NH₂ |
| 948 | F₃CO-phenyl-imidazole | (CH₂)₃CH₃ | -(CH₂)₂-(furan-3-yl) |
| 949 | 4-Cl-3-CF₃-phenyl-imidazole | (CH₂)₂CH₃ | -(CH₂)₃-(4-methylthiazol-2-yl) |
| 950 | 4-Cl-3-CF₃-phenyl-imidazole | (CH₂)₂CH₃ | -(CH₂)₂-(tetrahydrofuran-3-yl) |
| 951 | benzimidazole | (CH₂)₂CH₃ | -(CH₂)₂-(tetrahydrofuran-3-yl) |
| 952 | 2-phenyl-furan-4-yl | (CH₂)₃CH₃ | (CH₂)₃OEt |
| 953 | 5-(4-Cl-phenyl)-furan-2-yl | (CH₂)₂CH₃ | (CH₂)₃OEt |
| 954 | biphenyl | (CH₂)₂CH₃ | (CH₂)₃OEt |
| 955 | 4-phenoxyphenyl | (CH₂)₂CH₃ | (CH₂)₃OEt |

TABLE 10-continued
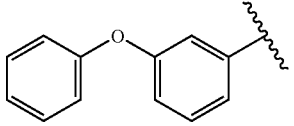
| Example # | Arb | V | R⁵ |
|---|---|---|---|
| 956 | 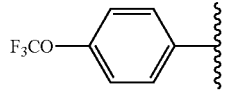 | (CH₂)₂CH₃ | (CH₂)₃OEt |
| 957 | 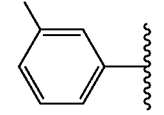 4-F₃CO-C₆H₄- | (CH₂)₂CH₃ | (CH₂)₃OEt |
| 958 | 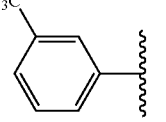 3-F₃CO-C₆H₄- | (CH₂)₃CH₃ | (CH₂)₃OEt |
| 959 | 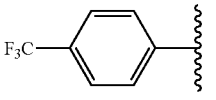 3-F₃C-C₆H₄- | (CH₂)₃CH₃ | (CH₂)₃OEt |
| 960 |  4-F₃C-C₆H₄- | (CH₂)₃CH₃ | (CH₂)₃OEt |
| 961 | 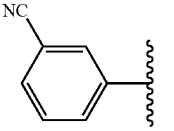 4-F-C₆H₄- | (CH₂)₃CH₃ | (CH₂)₃OEt |
| 962 | 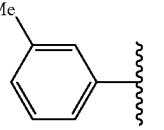 3-NC-C₆H₄- | (CH₂)₃CH₃ | (CH₂)₃OEt |
| 963 | 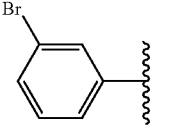 3-Me-C₆H₄- | (CH₂)₃CH₃ | (CH₂)₃OEt |
| 964 | 3-Br-C₆H₄- | (CH₂)₃CH₃ | (CH₂)₃OEt |
| 965 | 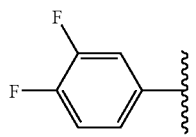 3,4-diF-C₆H₃- | (CH₂)₃CH₃ | (CH₂)₃OEt |

TABLE 10-continued
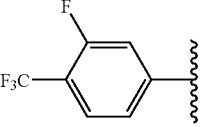
| Example # | Arb | V | R5 |
|---|---|---|---|
| 966 |  3-F-4-CF3-phenyl | (CH2)3CH3 | (CH2)3OEt |
| 967 |  3,4-diCl-phenyl | (CH2)3CH3 | (CH2)3OEt |
| 968 | 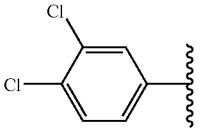 3-Cl-4-F-phenyl | (CH2)3CH3 | (CH2)3OEt |
| 969 |  3,5-diCl-phenyl | (CH2)3CH3 | (CH2)3OEt |
| 970 |  3,5-bis(CF3)-phenyl | (CH2)3CH3 | (CH2)3OEt |
| 971 | 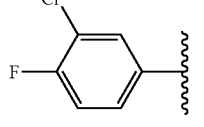 4-butyl-phenyl | (CH2)3CH3 | (CH2)3OEt |
| 972 |  4-iPr-phenyl | (CH2)3CH3 | (CH2)3OEt |
| 973 |  4-tBu-phenyl | (CH2)3CH3 | (CH2)3OEt |
| 974 | 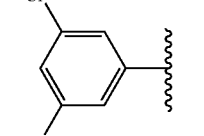 2-naphthyl | (CH2)3CH3 | (CH2)3OEt |

TABLE 10-continued

| Example # | Arb | V | R⁵ |
|---|---|---|---|
| 975 | benzo[1,3]dioxol-5-yl | (CH₂)₃CH₃ | (CH₂)₃OEt |
| 976 | benzo[1,2,5]oxadiazol-5-yl | (CH₂)₃CH₃ | (CH₂)₃OEt |
| 977 | quinolin-3-yl | (CH₂)₃CH₃ | (CH₂)₃OEt |
| 978 | 6-chloroquinolin-3-yl | (CH₂)₃CH₃ | (CH₂)₃OEt |
| 979 | benzofuran-3-yl | (CH₂)₃CH₃ | (CH₂)₃OEt |
| 980 | 5-chlorobenzofuran-3-yl | (CH₂)₃CH₃ | (CH₂)₃OEt |
| 981 | 6-chlorobenzofuran-3-yl | (CH₂)₃CH₃ | (CH₂)₃OEt |
| 982 | 7-chlorobenzofuran-3-yl | (CH₂)₃CH₃ | (CH₂)₃OEt |

TABLE 10-continued

| Example # | Arb | V | R⁵ |
|---|---|---|---|
| 983 | 5-fluoro-benzofuran-3-yl | (CH₂)₃CH₃ | (CH₂)₃OEt |
| 984 | 5-trifluoromethyl-benzofuran-3-yl | (CH₂)₃CH₃ | (CH₂)₃OEt |
| 985 | 5-trifluoromethoxy-benzofuran-3-yl | (CH₂)₃CH₃ | (CH₂)₃OEt |
| 986 | 5,7-dichloro-benzofuran-3-yl | (CH₂)₃CH₃ | (CH₂)₃OEt |
| 987 | 5,6-dichloro-benzofuran-3-yl | (CH₂)₃CH₃ | (CH₂)₃OEt |
| 988 | 2H-chromen-3-yl | (CH₂)₃CH₃ | (CH₂)₃OEt |
| 989 | 6-chloro-2H-chromen-3-yl | (CH₂)₃CH₃ | (CH₂)₃OEt |
| 990 | 6-methoxy-2H-chromen-3-yl | (CH₂)₃CH₃ | (CH₂)₃OEt |

TABLE 11

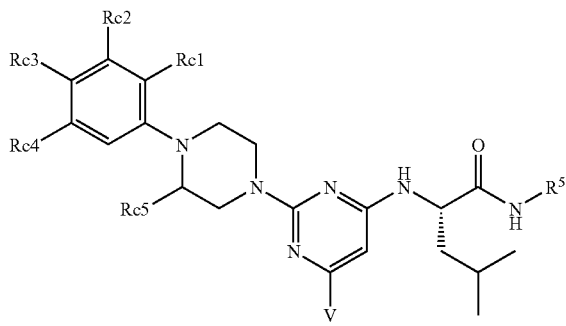

| Example # | Rc1 | Rc2 | Rc3 | Rc4 | Rc5 | V | R5 |
|---|---|---|---|---|---|---|---|
| 991 | H | H | H | H | H | $(CH_2)_3CH_3$ | $(CH_2)_3OEt$ |
| 992 | H | H | H | H | H | $(CH_2)_3CH_3$ | $(CH_2)_3CF_3$ |
| 993 | H | H | $NO_2$ | H | H | $(CH_2)_3CH_3$ | $(CH_2)_3OEt$ |
| 994 | H | H | $NO_2$ | H | H | $(CH_2)_3CH_3$ | $(CH_2)_3OEt$ |
| 995 | H | H | $NO_2$ | H | H | $CH_2CH_3$ | $(CH_2)_3OEt$ |
| 996 | H | H | $NO_2$ | H | H | $CH_3$ | $(CH_2)_3OEt$ |
| 997 | H | H | $NO_2$ | H | $CH_3$ | $(CH_2)_3CH_3$ | $(CH_2)_3OEt$ |
| 998 | H | H | Cl | H | H | $(CH_2)_3CH_3$ | $(CH_2)_3OEt$ |
| 999 | H | H | Cl | H | H | $(CH_2)_3CH_3$ | $(CH_2)_3OEt$ |
| 1000 | H | H | Cl | H | H | $CH_2CH_3$ | $(CH_2)_3OEt$ |
| 1001 | H | H | Cl | H | H | $CH_3$ | $(CH_2)_3OEt$ |
| 1002 | H | H | Cl | H | H | $(CH_2)_3CH_3$ | $(CH_2)_3NMe(OMe)$ |
| 1003 | Cl | H | H | H | H | $(CH_2)_3CH_3$ | $(CH_2)_3OEt$ |
| 1004 | H | Cl | Cl | H | H | $(CH_2)_3CH_3$ | $(CH_2)_3OEt$ |
| 1005 | H | Cl | Cl | H | H | $(CH_2)_3CH_3$ | $(CH_2)_3OEt$ |
| 1006 | Cl | Cl | H | H | H | $(CH_2)_3CH_3$ | $(CH_2)_3OEt$ |
| 1007 | H | Cl | H | Cl | H | $(CH_2)_3CH_3$ | $(CH_2)_3OEt$ |
| 1008 | H | $CF_3$ | H | H | H | $(CH_2)_3CH_3$ | $(CH_2)_3OEt$ |
| 1009 | H | H | F | H | H | $(CH_2)_3CH_3$ | $(CH_2)_3OEt$ |
| 1010 | H | H | F | H | H | $(CH_2)_3CH_3$ | $(CH_2)_3OEt$ |
| 1011 | F | H | H | H | H | $(CH_2)_3CH_3$ | $(CH_2)_3OEt$ |
| 1012 | F | H | H | H | H | $(CH_2)_3CH_3$ | $(CH_2)_3OEt$ |
| 1013 | H | H | $CH_3$ | H | H | $(CH_2)_3CH_3$ | $(CH_2)_3OEt$ |
| 1014 | H | H | $CH_3$ | H | H | $(CH_2)_3CH_3$ | $(CH_2)_3OEt$ |
| 1015 | H | $CH_3$ | H | H | H | $(CH_2)_3CH_3$ | $(CH_2)_3OEt$ |
| 1016 | $CH_3$ | H | H | H | H | $(CH_2)_3CH_3$ | $(CH_2)_3OEt$ |
| 1017 | H | $CH_3$ | $CH_3$ | H | H | $(CH_2)_3CH_3$ | $(CH_2)_3OEt$ |
| 1018 | $CH_3$ | H | $CH_3$ | H | H | $(CH_2)_3CH_3$ | $(CH_2)_3OEt$ |
| 1019 | $CH_3$ | $CH_3$ | H | H | H | $(CH_2)_3CH_3$ | $(CH_2)_3OEt$ |
| 1020 | $CH_3$ | H | H | Cl | H | $(CH_2)_3CH_3$ | $(CH_2)_3OEt$ |
| 1021 | H | H | $OCH_3$ | H | H | $(CH_2)_3CH_3$ | $(CH_2)_3OEt$ |
| 1022 | H | H | $OCH_3$ | H | H | $(CH_2)_3CH_3$ | $(CH_2)_3OEt$ |
| 1023 | H | $OCH_3$ | H | H | H | $(CH_2)_3CH_3$ | $(CH_2)_3OEt$ |
| 1024 | $OCH_3$ | H | H | H | H | $(CH_2)_3CH_3$ | $(CH_2)_3OEt$ |
| 1025 | $OCH_3$ | H | H | Cl | H | $(CH_2)_3CH_3$ | $(CH_2)_3OEt$ |
| 1026 | H | $OCH_3$ | $OCH_3$ | H | H | $(CH_2)_3CH_3$ | $(CH_2)_3OEt$ |
| 1027 | H | OH | H | H | H | $(CH_2)_3CH_3$ | $(CH_2)_3OEt$ |
| 1028 | H | H | CN | H | H | $(CH_2)_3CH_3$ | $(CH_2)_3OEt$ |
| 1029 | H | H | CN | H | $CH_3$ | $(CH_2)_3CH_3$ | $(CH_2)_3OEt$ |
| 1030 | CN | H | H | H | H | $(CH_2)_3CH_3$ | $(CH_2)_3OEt$ |

Chart 2
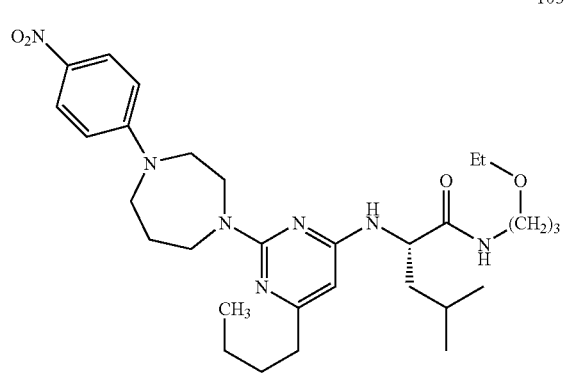
1031
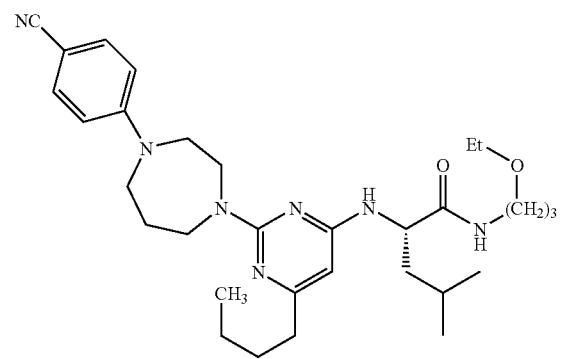
1032
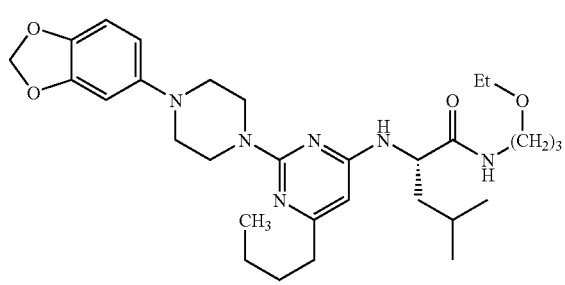
1033
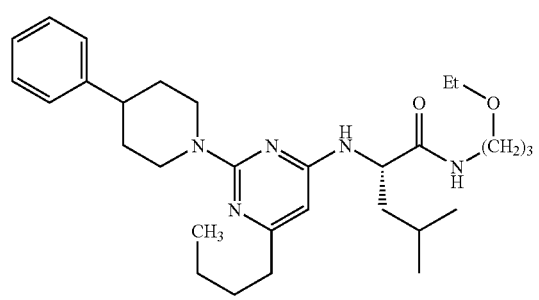
1034
-continued
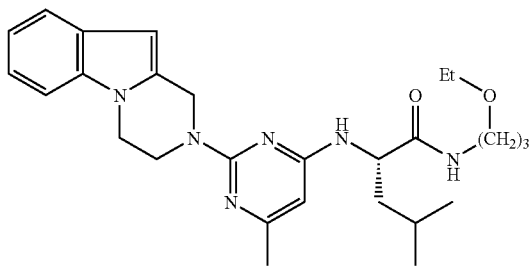
1035
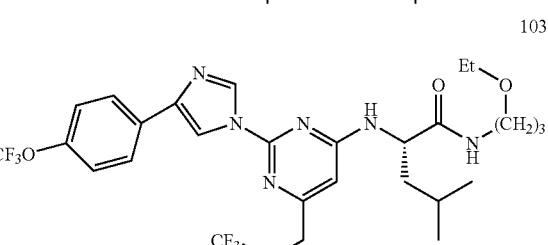
1036
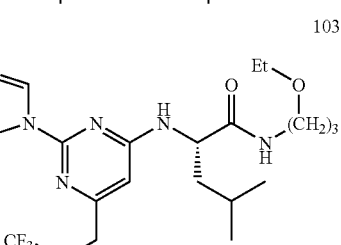
1037
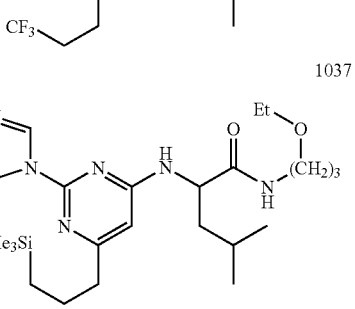
1038
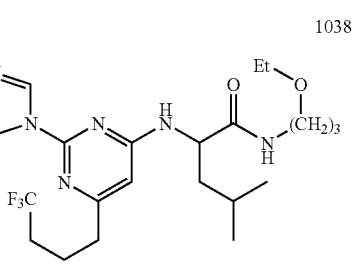
1039
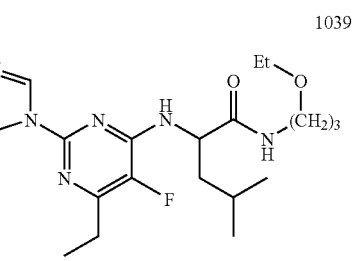
1040

While it may be possible for the compounds of formula I to be administered as the raw chemical, it is preferable to present them as a pharmaceutical composition. According to a further aspect, the present invention provides a pharmaceutical composition comprising a compound of formula Ia or a pharmaceutically acceptable salt or solvate thereof, together with one or more pharmaceutically carriers thereof and optionally one or more other therapeutic ingredients, as discussed below. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of the invention or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. The pharmaceutical formulations may additionally comprise other drugs, such as anti-inflammatory drugs.

The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol. Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia. It should be understood that in addition to the ingredients particularly mentioned above, the formulations of this invention may include other agents conventional in the art having regard to the type of formulation in question, for example those suitable for oral administration may include flavoring agents.

Preferred unit dosage formulations are those containing an effective dose, as hereinbelow recited, or an appropriate fraction thereof, of the active ingredient. The compounds of the invention may be administered orally or via injection at a dose from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula (I) are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

EXAMPLE 1

Aqueous Suspension for Injection

A suspending vehicle is prepared from the following materials:

| | |
|---|---|
| Polyethylene glycol 4000 | 30 gm. |
| Potassium chloride | 11.2 gm. |
| Polysorbate 80 | 2 gm. |

-continued

| | |
|---|---|
| Methylparaben | 0.2 gm. |
| Water for injection q.s. | 1000 mL. |

The parabens are added to a major portion of the water and are dissolved therein by stirring and heating to 65° C. The resulting solution is cooled to room temperature and the remainder of the ingredients are added and dissolved. The balance of the water to make up the required volume is then added and the solution sterilized by filtration. The sterile vehicle thus prepared is then mixed with 3 gm of IL-8 receptor antagonist of the invention (e.g. compound 310), which has been previously reduced to a particle size less than about 10 microns and sterilized with ethylene oxide gas. The mixture is passed through a sterilized colloid mill and filled under aseptic conditions into sterile containers which are then sealed.

EXAMPLE 2

Water-Washable Cream

The following ingredients are formulated:

| Ingredients | Per Cent w/w |
|---|---|
| Compound 310 | 0.025 |
| Mineral Oil | 6.0 |
| Petrolatum | 15.0 |
| Polyethylene glycol 1000 monocetyl ether | 1.8 |
| Cetostearyl alcohol | 7.2 |
| Chlorocresol | 0.1 |
| Distilled water to produce 100 parts by weight | |

The IL-8 antagonist 310 is ball-milled with a little mineral oil to a particle size of less than 5 microns. The water is heated to boiling, the chlorocresol added and the solution then cooled to 65° C. Then the petrolatum, cetostearyl alcohol and polyethylene glycol ether are mixed together while heating to 65° C. The milled suspension is then added to the melt rinsing the container with mineral oil. The active ingredient oily phase thus prepared is added at 60° C. to the chlorocresol aqueous phase at 65° C. The mixture is stirred rapidly while cooling past the gelling point (40°–45° C.) and the stirring is continued at a speed sufficiently slow to permit the cream to set. The water-washable cream may be used in the treatment of dermatoses using either the open (without occlusion) or occlusive method of drug application.

EXAMPLE 3

| Topical Ointment | |
|---|---|
| Compound 310 | 1.00 gm. |
| Chloroxine | 1.00 gm. |
| Propylene Glycol | 7.00 gm. |
| Glyceryl monostearate with emulsifier | 5.00 gm. |
| White petrolatum q.s.a.d. | 100.00 gm. |

Heat the propylene glycol to 55° C. Add compound 310, and chloroxine and mix well. Add the remaining ingredients and mix until melted. Remove from heat and mix slowly until cooled to 45° C., then homogenize.

EXAMPLE 4

| Tablets | |
|---|---|
| Composition per tablet: | |
| compound 310 | 30 mg |
| Precipitated calcium carbonate | 50 mg |
| Corn Starch | 40 mg |
| Lactose | 73.4 mg |
| Hydroxypropylcellulose | 6 mg |
| Magnesium stearate | (0.05 mL) |
| Total | 200.0 mg |

Compound 310, precipitated calcium carbonate, corn starch, lactose and hydroxypropylcellulose are mixed together, water is added, and the mixture is kneaded, then dried in vacuum at 40° C. for 16 hours, ground in a mortar and passed through a 16-mesh sieve to give granules. To this is added magnesium stearate and the resultant mixture is made up into tablets each weighing 200 mg on a rotary tableting machine.

We claim:
1. A compound of formula

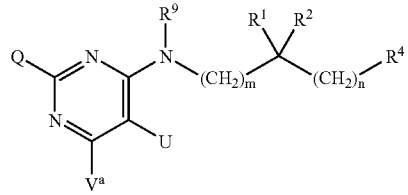

wherein
Q is chosen from hydroxyalkyl, unsubstituted and substituted aryl, unsubstituted and substituted heterocyclyl, $R^{12}OC(O)-(CH_2)_p-$, $R^{11}R^{12}NC(O)-$, $R^{11}C(O)NR^{12}-$, $R^{11}C(NH)NR^{12}-$, $R^{12}C(O)-$, $R^{11}OC(O)NR^{12}-$, $R^{11}NHC(O)NR^{12}-$ and HetB-Y-HetA-;

U is chosen from hydrogen, halogen, $(C_1-C_{20})$hydrocarbon and substituted $(C_1-C_{20})$alkyl;

$V^a$ is chosen from $-R^3$, $-OR^3$ and $-SR^3$;

HetA is aryl or heterocyclyl;

Y is $-CH_2-$, a direct bond or $-O-$;

HetB is aryl or heterocyclyl, with the proviso that when HetA is imidazole, Y is a direct bond and $V^a$ is hydrogen, $(C_1-C_6)$alkyl or $(C_1-C_6)$alkoxy, HetB cannot be benzofuran, indole, benzothiophene or substituted benzofuran, indole or benzothiophene;

$R^1$ is chosen from alkyl, cycloalkyl, aryl, heterocyclyl, $-(C_1-C_4)$alkylaryl, and $-(C_1-C_4)$-alkylheterocyclyl;

$R^2$ is H or $(C_1-C_4)$alkyl;

$R^3$ is chosen from $(C_1-C_{20})$hydrocarbon, substituted $(C_1-C_{20})$alkyl and $[(C_1-C_{20})$alkyl$]R^7$;

$R^4$ is $A^1$ or $A^2$;

$A^1$ is chosen from $-C(O)NR^5R^6$, $-C(O)OR^5$, and

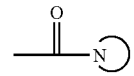

$A^2$ is chosen from $R^8C(O)NH-$, $R^5R^6N-$, and $R^5O-$, with the proviso that, when m and n are both zero, $R^4$ cannot be $A^2$;

is a 5-, 6- or 7-membered nitrogen heterocycle attached to the carbonyl of $A^1$ via nitrogen;

$R^5$ is chosen from aryl, heterocyclyl, -(heterocyclyl)-$R^{10}$, —$CH_2C(O)NH$alkyl, —[($C_1$–$C_{10}$)hydrocarbon]-$R^{10}$ and -[(monosubstituted ($C_1$–$C_{10}$)alkyl]-$R^{10}$, with the proviso that when $A^1$ is —$C(O)NR^5R^6$ and a nitrogen occurs in $R^5$, the nitrogen in $R^5$ must be more than two carbons removed from the nitrogen in —$C(O)NR^5R^6$;

$R^6$ is H or $C_1$–$C_6$-alkyl; or $R^1$ and $R^6$ taken together form a 5-, 6- or 7-membered nitrogen heterocycle;

$R^7$ is chosen from aryl, substituted aryl, aryloxy, substituted aryloxy, arylthio, substituted arylthio, heteroaryloxy, substituted heteroaryloxy, heteroarylthio, substituted heteroarylthio, heterocyclyl, and substituted heterocyclyl;

$R^8$ is chosen from alkyl, aryl, substituted alkyl, —($C_1$–$C_4$)alkylaryl, and —($C_1$–$C_4$)alkylheterocyclyl;

$R^9$ is chosen from H, $C_1$–$C_6$-alkyl and aryl;

$R^{10}$ is chosen from H, F, alkyl, fluoroalkyl, —O-alkyl, —O-(substituted)alkyl,oxaalkyl, —S-alkyl, —SO-alkyl, —$SO_2$-alkyl, —$CH_2O$-alkyl, —$CH_2S$-alkyl, —$CH_2SO$-alkyl, —$CH_2SO_2$-alkyl, —N($C_1$–$C_6$)alkyl-O—($C_1$–$C_6$)alkyl, aryl, and heterocyclyl;

$R^{11}$ is chosen from H, $C_1$–$C_6$-alkyl, cycloalkyl, aryl and substituted-$C_1$–$C_6$-alkyl;

$R^{12}$ is H or $C_1$–$C_6$-alkyl;

m is zero or one;

n is zero or one, and p is zero or 1–6.

2. A compound of formula

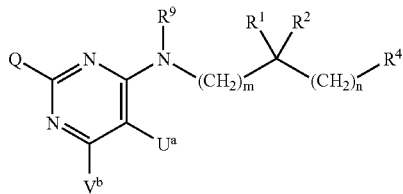

wherein

Q is chosen from hydroxyalkyl, unsubstituted and substituted aryl, unsubstituted and substituted heterocyclyl, $R^{12}OC(O)$—($CH_2$)$_p$—, $R^{11}R^{12}NC(O)$—, $R^{11}C(O)NR^{12}$—, $R^{11}C(NH)NR^{12}$—, $R^{12}C(O)$—, $R^{11}OC(O)NR^{12}$—, $R^{11}NHC(O)NR^{12}$— and HetB-Y-HetA-;

$U^a$ is chosen from halogen, ($C_1$–$C_{20}$)hydrocarbon and substituted ($C_1$–$C_{20}$)alkyl;

$V^b$ is chosen from hydrogen and halogen;

HetA is aryl or heterocyclyl;

Y is —$CH_2$—, a direct bond or —O—;

HetB is aryl or heterocyclyl, with the proviso that when HetA is imidazole, Y is a direct bond and $V^b$ is hydrogen, HetB cannot be benzofuran, indole, benzothiophene, or substituted benzofuran, indole or benzothiophene;

$R^1$ is chosen from alkyl, cycloalkyl, aryl, heterocyclyl, —($C_1$–$C_4$)alkylaryl, and —($C_1$–$C_4$)-alkylheterocyclyl;

$R^2$ is H or ($C_1$–$C_4$)alkyl;

$R^4$ is $A^1$ or $A^2$;

$A^1$ is chosen from —$C(O)NR^5R^6$, —$C(O)OR^5$, and

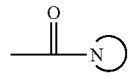

$A^2$ is chosen from $R^8C(O)NH$—, $R^5R^6N$—, and $R^5O$—, with the proviso that, when m and n are both zero, $R^4$ cannot be $A^2$;

is a 5-, 6- or 7-membered nitrogen heterocycle attached to the carbonyl of $A^1$ via nitrogen;

$R^5$ is chosen from aryl, heterocyclyl, -(heterocyclyl)-$R^{10}$, —$CH_2C(O)NH$alkyl, —($C_2$–$C_{10}$-hydrocarbon)-$R^{10}$ and -(monosubstituted $C_2$–$C_{10}$-alkyl)-$R^{10}$;

$R^6$ is H or $C_1$–$C_6$-alkyl; or $R^1$ and $R^6$ taken together form a 5-, 6- or 7-membered nitrogen heterocycle;

$R^8$ is chosen from alkyl, aryl, substituted alkyl, —($C_1$–$C_4$)alkylaryl, and —($C_1$–$C_4$)-alkylheterocyclyl;

$R^9$ is chosen from H, $C_1$–$C_6$-alkyl and aryl;

$R^{10}$ is chosen from H, F, alkyl, fluoroalkyl, —O-alkyl, —O-(substituted)alkyl, oxaalkyl, —S-alkyl, —SO-alkyl, —$SO_2$-alkyl, —$CH_2O$-alkyl, —$CH_2S$-alkyl, —$CH_2SO$-alkyl, —$CH_2SO_2$-alkyl, —N($C_1$–$C_6$)alkyl-O—($C_1$–$C_6$)alkyl, aryl, and heterocyclyl;

$R^{11}$ is chosen from H, $C_1$–$C_6$-alkyl, cycloalkyl, aryl and substituted-$C_1$–$C_6$-alkyl;

$R^{12}$ is H or $C_1$–$C_6$-alkyl;

m is zero or one;

n is zero or one; and p is zero or 1–6.

3. A compound of formula

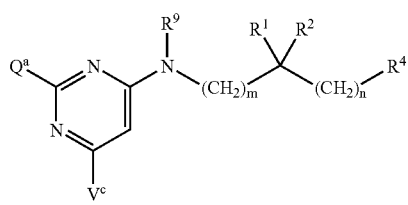

wherein $Q^a$ is chosen from hydroxydalkyl, unsubstituted and substituted aryl, unsubstituted heterocyclyl other than unsubstituted imidazole and unsubstituted triazole, substituted heterocyclyl, $R^{12}OC(O)$—($CH_2$)$_p$—, $R^{11}R^{12}NC(O)$—, $R^{11}C(O)NR^{12}$—, $R^{11}C(NH)NR^{12}$—, $R^{12}C(O)$—, $R^{11}OC(O)NR^{12}$—, $R^{11}NHC(O)NR^{12}$— and HetB-Y-HetA-;

$V^c$ is chosen from hydrogen, halogen and $R^{3a}$;

HetA is aryl or heterocyclyl;

Y is —$CH_2$—, a direct bond or —O—;

HetB is aryl or heterocyclyl, with the proviso that that when HetA is imidazole, Y is a direct bond and $V^c$ is hydrogen or ($C_1$–$C_6$)alkyl, HetB cannot be benzofuran, indole, benzothiophene, or substituted benzofuran, indole or benzothiophene;

R$^1$ is chosen from alkyl, cycloalkyl, aryl, heterocyclyl, —(C$_1$–C$_4$)alkylaryl, and —(C$_1$–C$_4$)-alkylheterocyclyl;

R$^2$ is H or (C$_1$–C$_4$)alkyl;

R$^{3a}$ is (C$_1$–C$_8$)alkyl;

R$^4$ is A$^1$ or A$^2$;

A$^1$ is chosen from —C(O)NR$^5$R$^6$, —C(O)OR$^5$, and

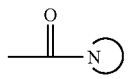

A$^2$ is chosen from R$^8$C(O)N—, R$^5$R$^6$N—, and R$^5$O—, with the proviso that, when m and n are both zero, R$^4$ cannot be A$^2$;

is a 5-, 6- or 7-membered nitrogen heterocycle attached to the carbonyl of A$^1$ via nitrogen;

R$^5$ is chosen from aryl, heterocyclyl, -(heterocyclyl)-R$^{10}$, —CH$_2$C(O)NHalkyl, —[(C$_1$–C$_{10}$)hydrocarbon]-R$^{10}$ and -[(monosubstituted (C$_1$–C$_{10}$)alkyl]-R$^{10}$, with the proviso that when A$^1$ is —C(O)NR$^5$R$^6$ and a nitrogen occurs in R$^5$, the nitrogen in R$^5$ must be more than two carbons removed from the nitrogen in —C(O)NR$^5$R$^6$;

R$^6$ is H or C$_1$–C$_6$-alkyl; or

R$^1$ and R$^6$ taken together form a 5-, 6- or 7-membered nitrogen heterocycle;

R$^8$ is chosen from alkyl, aryl, substituted alkyl, —(C$_1$–C$_4$)alkylaryl, and —(C$_1$–C$_4$)-alkylheterocyclyl;

R$^9$ is chosen from H, C$_1$–C$_6$-alkyl and aryl;

R$^{10}$ is chosen from H, F, alkyl, fluoroalkyl, —O-alkyl, —O-(substituted)alkyl, oxaalkyl, —S-alkyl, —SO-alkyl, —SO$_2$-alkyl, —CH$_2$O-alkyl, —CH$_2$S-alkyl, —CH$_2$SO-alkyl, —CH$_2$SO$_2$-alkyl, N(C$_1$–C$_6$)alkyl-O—(C$_1$–C$_6$)alkyl, aryl, and heterocyclyl;

R$^{11}$ is chosen from H, —(C$_1$–C$_6$)alkyl, cycloalkyl, aryl and substituted(C$_1$–C$_6$)alkyl;

R$^{12}$ is H or —(C$_1$–C$_6$)alkyl;

m is zero or one;

n is zero or one; and p is zero or 1–6.

4. A compound according to any of claims 1 to 3 wherein Q is HetB-Y-HetA-.

5. A compound according to claim 4 wherein HetA is chosen from the group consisting of phenyl, piperazine, imidazole, pyridine, furan, and substituted phenyl, piperazine, imidazole, pyridine and furan.

6. A compound according to claim 4 wherein HetB is chosen from the group consisting of aryl and heteroaryl.

7. A compound according to claim 4 wherein HetB is chosen from the group consisting of phenyl, furan, thiophene, benzodioxole, benzodioxane, benzofuran, dihydrobenzofuran, benzoxazole, benzimidazole, benzothiazole, benzothiophene and substituted phenyl, furan, thiophene, benzodioxole, benzodioxane, benzofuran, dihydrobenzofuran, benzoxazole, benzimidazole, benzothiazole and benzothiophene.

8. A compound according to claim 4 wherein:

V$^a$, V$^b$ or V$^c$ is chosen from hydrogen, R$^3$ and OR$^3$;

R$^3$ is chosen from (C$_1$ to C$_6$)hydrocarbon and substituted (C$_1$ to C$_6$)alkyl;

HetA is chosen from the group consisting of phenyl, imidazole, methylimidazole, pyridine, furan, hexahydrodiazepine, piperidine, methylpiperazine and piperazine; and HetB is chosen from the group consisting of phenyl, benzodioxane, benzodioxole, dihydrobenzofuran, benzofuran, benzothiazole, pyridine, furan, thiophene, benzothiophene, chroman, dihydrochroman and substituted phenyl, benzodioxole, pyridine and furan.

9. A compound according to any of claims 1 to 3 wherein:

Q or Q$^a$ is chosen from substituted benzimidazole, substituted pyridine, substituted phenyl, naphthylene, benzodioxole, benzooxadiazole, quinoline, substituted quinoline, benzofuran, substituted benzofuran, chroman, dihydrochroman, and tetrahydropyrazino[1,2-a]indole.

10. A compound according to claim 9 wherein:

V$^a$, V$^b$ or V$^c$ is chosen from hydrogen, R$^3$ and OR$^3$; and

R$^3$ is chosen from (C$_1$ to C$_6$)hydrocarbon and substituted (C$_1$ to C$_6$)alkyl.

11. A compound according to claim 9 wherein:

V$^a$ or V$^b$ is chosen from hydrogen and R$^3$; and

U or U$^a$ is halogen.

12. A compound according to claim 1 of formula

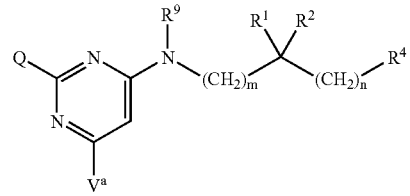

wherein

Q is chosen from hydroxyalkyl, aryl, heterocyclyl, substituted heterocyclyl, R$^{12}$OC(O)—(CH$_2$)$_p$—, R$^{11}$R$^{12}$NC(O)—, R$^{11}$C(O)NR$^{12}$—, R$^{11}$C(NH)NR$^{12}$—, R$^{12}$C(O)—, R$^{11}$OC(O)NR$^{12}$— and R$^{11}$NHC(O)NR$^{12}$;

V$^a$ is chosen from R$^3$, —OR$^3$, and —SR$^3$;

R$^1$ is chosen from alkyl, cycloalkyl, aryl, heterocyclyl, —(C$_1$–C$_4$)alkylaryl, and —(C$_1$–C$_4$)-alkylheterocyclyl;

R$^2$ is H or (C$_1$–C$_4$)alkyl;

R$^3$ is chosen from (C$_1$–C$_{20}$)hydrocarbon, substituted (C$_1$–C$_{20}$)alkyl, —[(C$_1$–C$_{20}$)alkyl]substituted aryl, —[(C$_1$–C$_{20}$)alkyl]substituted aryloxy, —[(C$_1$–C$_{20}$)alkyl]substituted arylthio, —[(C$_1$–C$_{20}$)alkyl] substituted heteroaryloxy, —[(C$_1$–C$_{20}$)alkyl] substituted heteroarylthio, and —[(C$_1$–C$_{20}$)alkyl]heterocyclyl;

R$^4$ is A$^1$ or A$^2$;

A$^1$ is chosen from —C(O)NR$^5$R$^6$, —C(O)OR$^5$, and

A$^2$ is chosen from R$^8$C(O)NH—, R$^5$R$^6$N—, and R$^5$O—, with the proviso that, when m and n are both zero, R$^4$ cannot be A$^2$;

is a 5-, 6- or 7-membered nitrogen heterocycle attached to the carbonyl of $A^1$ via nitrogen;

$R^5$ is chosen from aryl, heterocyclyl, -(heterocyclyl)-$R^{10}$, —$CH_2C(O)NH$alkyl, —$(C_2$–$C_{10}$-hydrocarbon)-$R^{10}$ and -[monosubstituted $(C_2$–$C^{10})$alkyl]-$R^{10}$;

$R^6$ is H or $C_1$–$C_6$-alkyl; or $R^1$ and $R^6$ taken together form a 5-, 6- or 7-membered nitrogen heterocycle;

$R^8$ is chosen from alkyl, aryl, substituted alkyl, —$(C_1$–$C_4)$ alkylaryl, and —$(C_1$–$C_4)$-alkylheterocyclyl;

$R^9$ is chosen from H, $C_1$–$C_6$-alkyl and aryl;

$R^{10}$ is chosen from H, alkyl, —O-alkyl, —S-alkyl, —SO-alkyl, —$SO_2$-alkyl, —$CH_2O$-alkyl, —$CH_2S$-alkyl, —$CH_2SO$-alkyl, —$CH_2SO_2$-alkyl, aryl, and heterocyclyl;

$R^{11}$ is chosen from H, $C_1$–$C_6$-alkyl, cycloalkyl, aryl and substituted($C_1$–$C_6$)alkyl;

$R^{12}$ is H or $C_1$–$C_6$-alkyl;

m is zero or one;

n is zero or one; and p is zero or 1–6.

13. A compound according to claim 12 wherein:

$A^1$ is chosen from —$C(O)NR^{5a}R^6$, —$C(O)OR^{5a}$, and

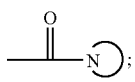

$A^2$ is chosen from $R^{8a}C(O)NH$—, $R^5R^6N$—, and $R^5O$—;

$R^{5a}$ is chosen from saturated heterocyclyl, -(heterocyclyl)-$R^{10}$, —$CH_2C(O)NH$alkyl, —$(C_2$–$C_{10}$-hydrocarbon)-$R^{10a}$, -[monosubstituted $(C_2$–$C_{10})$alkyl]-$R^{10a}$ and —$(C_4$–$C_8$-hydrocarbon)-$R^{13}$;

$R^{8a}$ is chosen from alkyl, —$(C_4)$alkylaryl, —$(C_1$–$C_4)$-alkylheterocyclyl and substituted alkyl other than —$(C_1$–$C_3)$-alkyl substituted with aryl; and $R^{10a}$ is chosen from —O-alkyl, —S-alkyl, —SO-alkyl, —$SO_2$-alkyl, —$CH_2O$-alkyl, —$CH_2S$-alkyl, —$CH_2SO$-alkyl, —$CH_2SO_2$-alkyl.

14. A compound according to claim 12 wherein:

Q is chosen from hydroxyalkyl, aryl, substituted heterocyclyl, $R^{12}OC(O)$—$(CH_2)_p$—, $R^{11}R^{12}NC(O)$—, $R^{11}C(O)NR^{12}$—, $R^{11}C(NH)NR^{12}$—, $R^{12}C(O)$—, $R^{11}OC(O)NR^{12}$—, $R^{11}NHC(O)NR^{12}$ and heterocyclyl other than 1-imidazolyl and 1-triazolyl.

15. A compound according to claim 12 wherein:

Q is chosen from hydroxyalkyl, aryl, substituted heterocyclyl, $R^{12}OC(O)$—$(CH_2)_p$—, $R^{11}R^{12}NC(O)$—, $R^{11}C(O)NR^{12}$—, $R^{11}C(NH)NR^{12}$—, $R^{12}C(O)$—, $R^{11}OC(O)NR^{12}$—, $R^{11}NHC(O)NR^{12}$ and heterocyclyl other than 1-imidazolyl and 1-triazolyl;

$A^1$ is chosen from —$C(O)NR^{5a}R^6$, —$C(O)OR^{5a}$, and

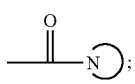

$A^2$ is chosen from $R^{8a}C(O)NH$—, $R^5R^6N$—, and $R^5O$—;

$R^{5a}$ is chosen from saturated heterocyclyl, -(heterocyclyl)-$R^{10}$, —$CH_2C(O)NH$alkyl, —$(C_2$–$C_{10}$-hydrocarbon)-$R^{10a}$, -(monosubstituted $C_2$–$C_{10}$-alkyl)-$R^{10a}$ and —$(C_4$–$C_8$-hydrocarbon)-$R^{13}$;

$R^{8a}$ is chosen from alkyl, —$(C_4)$alkylaryl, —$(C_1$–$C_4)$-alkylheterocyclyl and substituted alkyl other than —$(C_1$–$C_3)$-alkyl substituted with aryl; and $R^{10a}$ is chosen from —O-alkyl, —S-alkyl, —SO-alkyl, —$SO_2$-alkyl, —$CH_2O$-alkyl, —$CH_2S$-alkyl, —$CH_2SO$-alkyl, —$CH_2SO_2$-alkyl.

16. A compound according to any of claims 12 to 15 wherein Q is heteroaryl.

17. A compound according to claim 12 or 13 wherein Q is chosen from 1-imidazolyl, 4-substituted-1-imidazolyl, and 1-benzimidazolyl.

18. A compound according to claim 14 or 15 wherein Q is chosen from 4-substituted-1-imidazolyl, and 1-benzimidazolyl.

19. A compound according to any of claims 12 to 15 wherein $V^a$ is $R^3$ and $R^3$ is chosen from $(C_1$–$C_{20})$hydrocarbon, substituted $(C_1$–$C_{20})$alkyl and —$[(C_1$–$C_{20})$alkyl]substituted aryl.

20. A compound according to claim 19 wherein $R^3$ is $(C_4$–$C_{20})$hydrocarbon.

21. A compound according to any of claims 12 to 15 wherein $R^9$ is hydrogen or methyl.

m and n are zero;

$R^2$ is H; and $R^4$ is —$C(O)NHR^5$ or —$C(O)NHR^{5a}$.

22. A compound according to claim 21 wherein $R^5$ or $R^{5a}$ is —$(C_2$–$C_{10}$-hydrocarbon)-$R^{10}$ or -(heterocyclyl)-$R^{10}$.

23. A compound according to claim 21 wherein $R^5$ or $R^{5a}$ is —$(C_2$–$C_7$-hydrocarbon)-$R^{10}$ and $R^{10}$ is —S—$(C_1$–$C_6)$ alkyl or —O—$(C_1$–$C_6)$alkyl.

24. A compound according to claim 22 wherein $R^5$ or $R^{5a}$ is

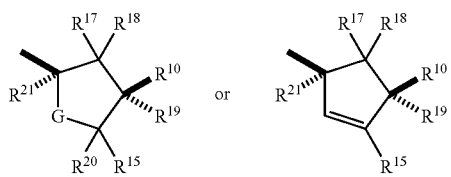

wherein

G is chosen from —$CH_2$—, and —$C(R^{22}R^{23})$—, and $R^{15}$, $R^{17}$, $R^{18}$, $R^{19}$, $R^{20}$, $R^{21}$, $R^{22}$, and $R^{23}$ are independently chosen from hydrogen and lower alkyl.

25. A compound according to claim 21 wherein $R^5$ or $R^{5a}$ is chosen from:

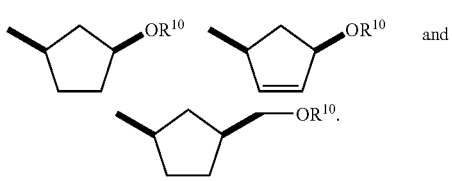

26. A compound according to claim 25 wherein $R^5$ or $R^{5a}$ is

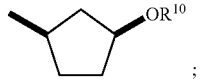

$V^a$ is $R^3$ and Q is heterocyclyl or substituted heterocyclyl.

27. A compound according to claim 12 wherein
Q is chosen from 1-imidazolyl, 4-methyl-1-imidazolyl, 4-trifluoromethyl-1-imidazolyl, 1-benzimidazolyl, 3-quinolinyl, 3-pyridinyl, and 5-(or 6-)methyl-1-benzimidazolyl;
$R^9$ is H or $CH_3$;
m and n are zero;
$R^1$ is chosen from n-propyl, isopropyl, n-butyl, isobutyl, isopentyl, cyclohexyl and cyclohexylmethyl;
$R^2$ is H;
$R^3$ is chosen from $(C_4-C_{14})$hydrocarbon, ω-phenoxy$(C_2-C_4)$alkyl, ω-phenylthio$(C_2-C_4)$alkyl, —[$(C_2-C_4)$alkyl]substituted phenyl, —[$(C_2-C_4)$alkyl]heteroaryl and —[$(C_2-C_4)$alkyl]substituted phenoxy;
$R^4$ is —C(O)NHR$^5$;
$R^5$ is —$(C_2-C_7$-hydrocarbon)-$R^{10}$; and
$R^{10}$ is —S—$(C_1-C_6)$alkyl or —O—$(C_1-C_6)$alkyl.

28. A compound according to claim 13 wherein
Q is chosen from 1-imidazolyl, 4-methyl-1-imidazolyl, 4-trifluoromethyl-1-imidazolyl, 1-benzimidazolyl, 3-quinolinyl, 3-pyridinyl, and 5-(or 6-)methyl-1-benzimidazolyl;
$R^9$ is H or $CH_3$;
m and n are zero;
$R^1$ is chosen from n-propyl, isopropyl, n-butyl, isobutyl, isopentyl, cyclohexyl and cyclohexylmethyl;
$R^2$ is H;
$R^3$ is chosen from $(C_4-C_{14})$hygrocarbon, ω-phenoxy$(C_2-C_4)$alkyl, ω-phenylthio$(C_2-C_4)$alkyl, —[$(C_2-C_4)$alkyl]substituted phenyl, —[$(C_2-C_4)$alkyl]heteroaryl and —[$(C_2-C_4)$alkyl]substituted phenoxy;
$R^4$ is —C(O)NHR$^{5a}$;
$R^{5a}$ is —$(C_2-C_7$-hydrocarbon)-$R^{10a}$; and
$R^{10a}$ is —S—$(C_1-C_6)$alkyl or —O—$(C_1-C_6)$alkyl.

29. A compound according to claim 14 wherein
Q is chosen from 4-methyl-1-imidazolyl, 4-trifluoromethyl-1-imidazolyl, 1-benzimidazolyl, 3-quinolinyl, 3-pyridinyl, and 5-(or 6-)methyl-1-benzimidazolyl;
$R^9$ is H or $CH_3$;
m and n are zero;
$R^1$ is chosen from n-propyl, isopropyl, n-butyl, isobutyl, isopentyl, cyclohexyl and cyclohexylmethyl;
$R^2$ is H;
$R^3$ is chosen from $(C_4-C_{14})$hydrocarbon, ω-phenoxy$(C_2-C_4)$alkyl, ω-phenylthio$(C_2-C_4)$alkyl, —[$(C_2-C_4)$alkyl]substituted phenyl, —[$(C_2-C_4)$alkyl] heteroaryl and —[$(C_2-C_4)$alkyl]substituted phenoxy;
$R^4$ is —C(O)NHR$^5$;
$R^5$ is —$(C_2-C_7$-hydrocarbon)-$R^{10}$; and
$R^{10}$ is —S—$(C_1-C_6)$alkyl or —O—$(C_1-C_6)$alkyl.

30. A compound according to claim 15 wherein
Q is chosen from 4-methyl-1-imidazolyl, 4-trifluoromethyl-1-imidazolyl, 1-benzimidazolyl, 3-quinolinyl, 3-pyridinyl, and 5-(or 6-)methyl-1-benzimidazolyl;
$R^9$ is H or $CH_3$;
m and n are zero $R^1$ is chosen from the group consisting of n-propyl, isopropyl, n-butyl, isobutyl, isopentyl, cyclohexyl and cyclohexylmethyl
$R^2$ is H;
$R^3$ is chosen from the group consisting of $(C_4-C_{14})$ hydrocarbon, ω-phenoxy$(C_2-C_4)$alkyl, ω-phenylthio$(C_2-C_4)$alkyl, —[$(C_2-C_4)$alkyl] substituted phenyl, —[$(C_2-C_4)$alkyl]heteroaryl and —[$(C_2-C_4)$alkyl]substituted phenoxy;
$R^4$ is —C(O)NHR$^{5a}$;
$R^{5a}$ is —$(C_2-C_7$-hydrocarbon)-$R^{10a}$; and
$R^{10a}$ is —S—$(C_1-C_6)$alkyl or —O—$(C_1-C_6)$alkyl.

31. A compound according to any of claims 27 to 30 wherein the stereogenic center to which $R^1$ and $R^2$ are attached is of the S absolute configuration.

32. A compound according to any of claims 27 to 30 wherein $R^5$ or $R^{5a}$ is

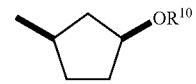

and $V^a$ is $R^3$.

33. A compound according to claim 12 of formula

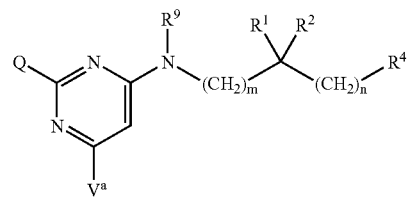

wherein
Q is chosen from 1-imidazolyl, 4-methyl-1-imidazolyl, and 4-trifluoromethyl-1-imidazolyl;
$V^a$ is $R^3$;
$R^9$ is H or $CH_3$;
m and n are zero;
$R^1$ is chosen from n-propyl, isopropyl, n-butyl, isobutyl, isopentyl, cyclohexyl and cyclohexylmethyl;
$R^2$ is H;
$R^3$ is chosen from $(C_4-C_{14})$hydrocarbon and substituted phenyl[$(C_2-C_4)$alkyl];
$R^4$ is —C(O)NHR$^5$;
$R^5$ is chosen from —$(C_2-C_7$-hydrocarbon)-$R^{10}$,

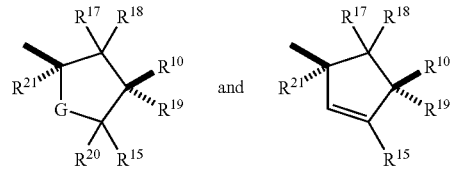

G is chosen from —$CH_2$— and —$C(R^{22}R^{23})$—, and —$C(R^{22}R^{23})SO_2$—; and $R^{15}$, $R^{17}$, $R^{18}$, $R^{19}$, $R^{20}$, $R^{21}$, $R^{22}$, and $R^{23}$ are independently chosen from hydrogen and lower alkyl; and
$R^{10}$ is —S—$(C_1-C_6)$alkyl or —O—$(C_1-C_6)$alkyl.

* * * * *